US011331328B2

(12) United States Patent
Zhou et al.

(10) Patent No.: US 11,331,328 B2
(45) Date of Patent: May 17, 2022

(54) COMPOSITIONS AND METHODS FOR INHIBITING ANTIAPOPTOTIC BCL-2 PROTEINS AS ANTI-AGING AGENTS

(71) Applicant: Board of Trustees of the University of Arkansas, Little Rock, AR (US)

(72) Inventors: Daohong Zhou, Little Rock, AR (US); Yingying Wang, Little Rock, AR (US); Jianhui Chang, Little Rock, AR (US); Lijian Shao, Little Rock, AR (US); Yi Luo, Little Rock, AR (US); Wei Feng, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 0 days.

(21) Appl. No.: 15/308,552

(22) PCT Filed: May 5, 2015

(86) PCT No.: PCT/US2015/029208
§ 371 (c)(1),
(2) Date: Nov. 2, 2016

(87) PCT Pub. No.: WO2015/171591
PCT Pub. Date: Nov. 12, 2015

(65) Prior Publication Data
US 2017/0056421 A1    Mar. 2, 2017

Related U.S. Application Data

(60) Provisional application No. 61/988,705, filed on May 5, 2014.

(51) Int. Cl.
*A61K 31/635* (2006.01)
*C07K 1/00* (2006.01)
*A61K 31/5377* (2006.01)

(52) U.S. Cl.
CPC ........ *A61K 31/635* (2013.01); *A61K 31/5377* (2013.01); *C07K 1/00* (2013.01)

(58) Field of Classification Search
CPC ... A61K 31/5377; A61K 31/635; A61P 43/00; C07K 1/00
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,223,409 A | 6/1993 | Ladner et al. |
| 5,264,618 A | 11/1993 | Felgner et al. |
| 5,403,484 A | 4/1995 | Ladner et al. |
| 5,491,069 A | 2/1996 | Dirmi et al. |
| 5,571,698 A | 11/1996 | Ladner et al. |
| 5,888,764 A | 3/1999 | Mountz et al. |
| 6,492,389 B1 | 12/2002 | Huang et al. |
| 6,566,495 B1 | 5/2003 | Fodor et al. |
| 6,572,876 B2 | 6/2003 | Waggle et al. |
| 7,939,313 B2 | 5/2011 | Heyduk et al. |
| 8,232,273 B2 | 7/2012 | Baell et al. |
| 10,071,087 B2 | 9/2018 | Zheng et al. |
| 2005/0084876 A1 | 4/2005 | Tschopp et al. |
| 2005/0208151 A1 | 9/2005 | Hurez et al. |
| 2006/0140959 A1 | 6/2006 | Fisher et al. |
| 2007/0072860 A1 | 3/2007 | Bruncko et al. |
| 2008/0171051 A1 | 7/2008 | Johnston et al. |
| 2009/0312373 A1 | 12/2009 | Lee et al. |
| 2010/0086941 A1 | 4/2010 | Adami et al. |
| 2010/0093613 A1 | 4/2010 | Kunkel |
| 2010/0310504 A1 | 12/2010 | Lowe et al. |
| 2011/0028387 A1 | 2/2011 | Garcia et al. |
| 2011/0053938 A1 | 3/2011 | Foley et al. |
| 2011/0086860 A1 | 4/2011 | Kimura et al. |
| 2012/0059004 A1 | 3/2012 | Elliott et al. |
| 2012/0156134 A1 | 6/2012 | Squires |
| 2012/0157455 A1 | 6/2012 | Foley et al. |
| 2013/0195884 A1 | 8/2013 | Boutros et al. |
| 2013/0237539 A1 | 9/2013 | Foley et al. |
| 2014/0005190 A1 | 1/2014 | Baell et al. |

(Continued)

FOREIGN PATENT DOCUMENTS

| | | |
|---|---|---|
| CN | 101774875 A | 7/2010 |
| CN | 101939008 A | 1/2011 |

(Continued)

OTHER PUBLICATIONS

Wang et al. Jan. 2010,Free Radic. Biol. Med. 48(2), pp. 348-356. (Year: 2010).*
Wang Cancer Research, 55, 1995, pp. 2284-2292. (Year: 1995).*
Chen et al. Mol. Cancer Ther. 10(12), Dec. 2011, pp. 2340-2349. (Year: 2011).*
Mohammed et al. Clinical Cancer Research 2007, 13(7), pp. 2226-2235 (Year: 2007).*
Robak, Journal of Leukemia, 2015, vol. 3, issue 3 pp. 1-3 (Year: 2015).*
He at al. International Journal of Oncology, 45, pp. 1099-1108, 2014 (Year: 2014).*
Tang et al., Journal of Medicinal Chemistry, 2007, 50(8), pp. 1723-1726 (Year: 2007).*

(Continued)

*Primary Examiner* — Kara R McMillian
(74) *Attorney, Agent, or Firm* — Polsinelli PC

(57) ABSTRACT

The present disclosure provides compositions and methods for selectively killing senescent cells, wherein the selective killing of senescent cells delays aging and treats age-related disorders.

3 Claims, 51 Drawing Sheets
(16 of 51 Drawing Sheet(s) Filed in Color)
Specification includes a Sequence Listing.

(56) References Cited

U.S. PATENT DOCUMENTS

| | | | |
|---|---|---|---|
| 2014/0024639 | A1 | 1/2014 | Adams et al. |
| 2014/0199234 | A1 | 7/2014 | Wang et al. |
| 2014/0356322 | A1 | 12/2014 | Crews et al. |
| 2015/0291562 | A1 | 10/2015 | Crew et al. |
| 2016/0095850 | A1 | 4/2016 | Cooper et al. |
| 2016/0176916 | A1 | 6/2016 | Bradner et al. |
| 2016/0339019 | A1 | 11/2016 | Laberge et al. |
| 2017/0246155 | A1 | 8/2017 | Zheng et al. |
| 2017/0348307 | A1 | 12/2017 | Laberge et al. |
| 2018/0002431 | A1 | 1/2018 | Zhou et al. |
| 2018/0021323 | A1 | 1/2018 | Zhou et al. |
| 2018/0369223 | A1 | 12/2018 | Zheng et al. |
| 2019/0054097 | A1 | 2/2019 | Zhou et al. |
| 2019/0135801 | A1 | 5/2019 | Zheng et al. |

FOREIGN PATENT DOCUMENTS

| | | |
|---|---|---|
| CN | 102125552 A | 7/2011 |
| CN | 102146054 A | 8/2011 |
| CN | 103601670 A | 2/2014 |
| CN | 105085620 A | 11/2015 |
| EP | 0532767 A1 | 3/1993 |
| EP | 2985285 A1 | 2/2016 |
| JP | 11349568 A | 12/1999 |
| WO | 2002026940 A1 | 4/2002 |
| WO | 2002097053 A2 | 12/2002 |
| WO | 2004106328 A1 | 12/2004 |
| WO | 2006023778 A2 | 3/2006 |
| WO | 2008119741 A2 | 10/2008 |
| WO | 2009114126 A1 | 9/2009 |
| WO | 2009129317 A1 | 10/2009 |
| WO | 2009155386 A1 | 12/2009 |
| WO | 2010080503 A1 | 7/2010 |
| WO | 2010120943 A1 | 10/2010 |
| WO | 2010138588 A2 | 12/2010 |
| WO | 2011009861 A1 | 1/2011 |
| WO | 2011130395 A1 | 10/2011 |
| WO | 2012030408 A1 | 3/2012 |
| WO | 2013083098 A2 | 6/2013 |
| WO | 2013106643 A2 | 7/2013 |
| WO | 2013178821 A1 | 12/2013 |
| WO | 2014089124 A1 | 6/2014 |
| WO | 2014108452 A1 | 7/2014 |
| WO | 2014174511 A1 | 10/2014 |
| WO | 2015116740 A1 | 8/2015 |
| WO | 2015171591 A1 | 11/2015 |
| WO | 2016014625 A1 | 1/2016 |
| WO | 2016118855 A1 | 7/2016 |
| WO | 2016118859 A1 | 7/2016 |
| WO | 2017012774 A1 | 1/2017 |
| WO | 2017101851 A1 | 6/2017 |
| WO | 2017184995 A1 | 10/2017 |
| WO | 2019221755 A1 | 11/2019 |

OTHER PUBLICATIONS

Arnold et al. Molecular Cancer, 2008, 7:20 pp. 1-10 (Year: 2008).*

Waring, P. et al., "Cell death induced by the Fas/Fas ligand pathway and its role in pathology," Immunology and Cell Biology, 1999, pp. 312-317, vol. 77.

Wood, T. et al., "Selective Inhibition of Histone Deacetylases Sensitizes Malignant Cells to Death Receptor Ligands," Mol. Cancer Ther., Jan. 2010, pp. 246-256, vol. 9, No. 1.

Adams, D. et al., "Synthesis, cellular evaluation, and mechanism of action of piperlongumine analogs," PNAS, Sep. 18, 2012, pp. 15115-15120, vol. 109, No. 38.

Banerjee, T. et al., "The crystal and molecular structure of N-(3,4,5-trimethoxycinnamoyl)-A3-piperidine-2-one, an amide alkaloid (piperlongumine), C17H19NO5," Can. J. Chem., 1986, pp. 876-880, vol. 64.

Bensoussan, C. et al., "Iron-catalyzed cross-coupling between C-bromo mannopyranoside derivatives and a vinyl Grignard reagent: toward the synthesis of the C31-C52 fragment of amphidinol 3," Tetrahedron, 2013, pp. 7759-7770, vol. 69, No. 36, Elsevier Ltd.

Bezerra, D. et al., "Overview of the therapeutic potential of piplartine (piperlongumine)," Eur. J. Pharma. Sci., 2013, pp. 453-463, vol. 48, Elsevier B.V.

Bokesch, H. et al., "A New Hypoxia Inducible Factor-2 Inhibitory Pyrrolinone Alkaloid from Roots and Stems of Piper sarmentosum," Chem. Pharm. Bull., 2011, pp. 1178-1179, vol. 59, No. 9, Pharmaceutical Society of Japan.

Campisi, J. et al., "Senescent Cells, Tumor Suppression, and Organismal Aging: Good Citizens, Bad Neighbors," Cell, Feb. 25, 2005, pp. 513-522, vol. 120, Elsevier Inc.

Campisi, J., "Cellular senescence: putting the paradoxes in perspective," Curr. Opin. Genet. Dev., 2011, pp. 107-112, vol. 21, Elsevier.

Chatterjee, A. et al., "Alkaloids of Piper Longum Linn-I: Structure and Synthesis of Piperlongumine and Piperlonguminine," Tetrahedron, 1967, pp. 1769-1781, vol. 23, No. 4, Pergamon Press, Northern Ireland.

Dodson, C. et al., "Cenocladamide, a dihydropyridone alkaloid from Piper cenocladum," Phytochemistry, 2000, pp. 51-54, vol. 53, Elsevier Science Ltd.

Duh, C. et al., "Cytotoxic Pyridone Alkaloids From the Leaves of Piper Aborescens," J. Nat. Prod., Nov.-Dec. 1990, pp. 1575-1577, vol. 53, No. 6.

Fontenele, J. et al., "Antiplatelet effects of piplartine, an alkamide isolated from Piper tuberculatum: possible involvement of cyclooxygenase blockade and antioxidant activity," J. Pharm. Pharmacol., 2009, pp. 511-515, vol. 61, No. 4.

Joshi, B. et al., "On the Structure of Piplartine and a Synthesis of Dihydropiplartine," Tetrahedron Lett., 1968, pp. 2395-2400, vol. 9, No. 20, Pergamon Press, Great Britain.

Kubo, M. et al., "Evaluation of Constituents of Piper retrofractum Fruits on Neurotrophic Activity," J. Nat. Prod., 2013, pp. 769-773, vol. 76, No. 4, The American Chemical Society and American Society of Pharmacognosy.

Kumar, J. et al., "Synthesis, anticancer, and antibacterial activities of piplartine derivatives on cell cycle regulation and growth inhibition," Journal of Asian Natural Products Research, Jun. 1, 2013, pp. 658-669, vol. 15, No. 6, Taylor & Francis Group.

Loo, D. et al., "Measurement of Cell Death," Methods Cell Biol., 1998, pp. 251-264, vol. 57, Chapter 14, Academic Press.

Rao, V. et al., "Synthesis and biological evaluation of new piplartine analogues as potent aldose reductase inhibitors (ARIs)," Eur. J. Med. Chem., 2012, pp. 344-361, vol. 57, Elsevier Masson SAS.

Rodier, F. et al., "Four faces of cellular senescence," J. Cell Biol., Feb. 14, 2011, pp. 547-556, vol. 192, The Rockefeller University Press.

Seo, Y. et al., "Synthesis and biological evaluation of piperlongumine derivatives as potent anti-inflammatory agents," Bioorg. Med. Chem. Lett., Dec. 15, 2014, pp. 5727-5730, vol. 24, No. 24, Elsevier Ltd.

Wu, Y. et al., "Design, synthesis and biological activity of piperlongumine derivatives as selective anticancer agents," Eur. J Med. Chem., 2014, pp. 545-551, vol. 82, Elsevier Masson SAS.

International Search Report and Written Opinion dated Aug. 7, 2018 from related International Patent Application No. PCT/US2018/033479; 9 pgs.

Extended European Search Report dated Oct. 5, 2017 from related European Patent Application No. 15789264.7; 7 pgs.

International Search Report and Written Opinion dated Jun. 29, 2015 from related International Patent Application No. PCT/US2015/013387; 34 pgs.

Nopora, A. et al., "Bcl-2 Controls Dendritic Cell Longevity In Vivo," J. Immunol., Sep. 2002, pp. 3006-3014, vol. 169, No. 6.

Office Action dated Oct. 23, 2017 from related U.S. Appl. No. 15/328,368; 8 pgs.

Warner, H. et al., "What Does Cell Death Have To Do With Aging?," JAGS, 1997, pp. 1140-1146, vol. 45, No. 9.

Office Action dated Feb. 27, 2018 from related U.S. Appl. No. 15/328,368; 6 pgs.

Shirley, S. et al., "Targeting c-FLIP in cancer," Cancer Lett., 2013, pp. 141-150, vol. 332, No. 2, Elsevier Ireland Ltd.

Siegelin, M. et al., "Genistein enhances proteasomal degradation of the short isoform of FLIP in malignant glioma cells and thereby

(56) References Cited

OTHER PUBLICATIONS augments TRAIL-mediated apoptosis," Neurosci. Lett., Apr. 3, 2009, pp. 92-97, vol. 453, No. 2, Elsevier Ireland Ltd.
Extended European Search Report dated Jan. 2, 2018 from related European Patent Application No. 15824181.0; 9 pgs.
International Search Report and Written Opinion dated Jul. 11, 2017 from related International Patent Application No. PCT/US2017/028875; 9 pgs.
Zengerle, M. et al., "Selective Small Molecule Induced Degradation of the BET Bromodomain Protein BRD4," ACS Chem. Biol., 2015, pp. 1770-1777, vol. 10, American Chemical Society.
Bucknall, M. et al., "Practical Quantitative Biomedical Applications of MALDI-TOF Mass Spectrometry," J. Am. Soc. Mass. Spectrom., 2002, pp. 1015-1027, vol. 13, Elsevier Science Inc.
Carell, T. et al., "A Solution-Phase Screening Procedure for the Isolation of Active Compounds from a Library of Molecules," Angew. Chem. Int. Ed. Engl., 1994, pp. 2059-2061, vol. 33, No. 20.
Chen, S. et al., "Celecoxib Promotes c-FLIP Degradation through Akt-Independent Inhibition of GSK3," Cancer Res., 2011, pp. 6270-6281, vol. 71, No. 19.
Chen, Q. et al., "Apo2L/TRAIL and Bcl-2-related proteins regulate type I interferon-induced apoptosis in multiple myeloma," Blood, Oct. 1, 2001, pp. 2183-2192, vol. 98, No. 7.
Cull, M. et al., "Screening for receptor ligands using large libraries of peptides linked to the C terminus of the lac repressor," PNAS, Mar. 1992, pp. 1865-1869, vol. 89.
Cwirla, S. et al., "Peptides on phage: A vast library of peptides for identifying ligands," PNAS, Aug. 1990, pp. 6378-6382, vol. 87.
Devlin, J. et al., "Random Peptide Libraries: A Source of Specific Protein Binding Molecules," Sci., Jul. 27, 1990, pp. 404-406, vol. 249, No. 4967, American Association for Advancement of Science.
Dewitt, S. et al., "'Diversomers': An approach to nonpeptide, nonoligomeric chemical diversity," PNAS, Aug. 1993, pp. 6909-6913, vol. 90.
Erb, E. et al., "Recursive deconvolution of combinatorial chemical libraries," PNAS, Nov. 1994, pp. 11422-11426, vol. 91.
Felici, F., "Selection of Antibody Ligands from a Large Library of Oligopeptides Expressed on a Multivalent Exposition Vector," J. Mol. Biol., 1991, pp. 301-310, vol. 222.
Fodor, S. et al., "Multiplexed biochemical assays with biological chips," Nature, 1993, pp. 555-556, vol. 364, No. 6437.
Gallop, M. et al., "Applications of Combinatorial Technologies to Drug Discovery. 1. Background and Peptide Combinatorial Libraries," J. Med. Chem., Apr. 1994, pp. 1233-1251, vol. 37, No. 9.
Gobom, J. et al., "Detection and Quantification of Neurotensin in Human Brain Tissue by Matrix-Asserted Laser Desorption/Ionization Time-of-Flight Mass Spectrometry," Anal. Chem., 2000, pp. 3320-3326, vol. 72.
Houghten, R. et al., "The Use of Synthetic Peptide Combinatorial Libraries for the Identification of Bioactive Peptides," Biotechniques, 1991, pp. 412-421, vol. 13, No. 3.
Lam, K. "Mini-review. Application of combinatorial library methods in cancer research and drug discovery," Anti-Cancer Drug Des., 1997, pp. 145-167, vol. 12, No. 3.
Lam, K. et al., "A new type of synthetic peptide library for identifying ligand-binding activity," Nature, Nov. 7, 1991, pp. 82-84, vol. 354.
Lee, S-J. et al., "Berberine sensitizes TRAIL-induced apoptosis through proteasome-mediated downregulation of c-FLIP and Mcl-1 proteins," Int. J. Oncol., 2011, pp. 485-492, vol. 38.
Mawji, I. et al., "A Chemical Screen Identifies Anisomycin as an Anoikis Sensitizer That Functions by Decreasing FLIP Protein Synthesis," Cancer Res., Sep. 1, 2007, pp. 8307-8315, vol. 67, No. 17.
Mirgorodskaya, E. et al., "Characterization of Protein Glycosylation by MALDI-TOFMS," Meth. Mol. Biol., 2000, pp. 273-292, vol. 146, Humana Press Inc.
Raja, S. et al., "The natural product honokiol preferentially inhibits cellular FLICE-inhibitory protein and augments death receptor-induced apoptosis," Mol. Cancer Ther., 2008, pp. 2212-2223, vol. 7, No. 7.
Rockett, J. et al., "DNA arrays: technology, options and toxicological applications," Xenobiotica, 2000, pp. 155-177, vol. 30, No. 2.
Safa, A. et al., "Targeting the Anti-Apoptotic Protein c-FLIP for Cancer Therapy," Cancers, 2011, pp. 1639-1671, vol. 3.
Sanders, Y. et al., "Histone Modifications in Senescence-Associated Resistance to Apoptosis by Oxidative Stress," Redox Biol., 2013, pp. 8-16, vol. 1, Elsevier B.V.
Schimmer, A. et al., "Identification of Small Molecules that Sensitize Resistant Tumor Cells to Tumor Necrosis Factor-Family Death Receptors," Cancer Res., 2006, pp. 2367-2375, vol. 66, No. 4.
Scott, J. et al., "Searching for Peptide Ligands with an Epitope Library," Sci., Jul. 27, 1990, pp. 386-390, vol. 249, No. 4967.
Zuckermann, R. et al., "Discovery of Nanomolar Ligands for 7-Transmembrane G-Protein-Coupled Receptors from a Diverse N-(Substituted)glycine Peptoid Library," J. Med. Chem., 1994, pp. 2678-2685, vol. 37.
Notice of Allowance dated May 8, 2018 from related U.S. Appl. No. 15/328,368; 5 pgs.
Baker, D et al., "Clearance of p16Ink4a-positive senescent cells delays ageing-associated disorders," Nature, 2011, pp. 232-236, vol. 479.
Baritaki, S. et al., "Chemotherapeutic drugs sensitize cancer cells to TRAIL-mediated apoptosis: up-regulation of DR5 and inhibition of Yin Yang 1," Mol. Cancer Ther., Apr. 2007, pp. 1387-1399, vol. 6, No. 4.
Barton, K. et al., "Selective HDAC Inhibition for the Disruption of Latent HIV-1 Infection," PLOS One, Aug. 2014, pp. 1-11, vol. 9, No. 8, e102684.
Beerman, I. et al., "Stem cells and the aging hematopoietic system," Curr. Opin. Immunol., 2010, pp. 500-506, vol. 22.
Burd, C. et al., "Monitoring tumorigenesis and senescence in vivo with a p16(INK4a)-luciferase model," Cell, 2013, pp. 340-351, vol. 152.
Campisi, J., "Aging, cellular senescence, and cancer," Annu. Rev. Physiol., 2013, pp. 685-705, vol. 75.
Caserta, T. et al., "Q-VD-OPh, a broad spectrum caspase inhibitor with potent antiapoptotic properties," Apoptosis, 2003, pp. 345-352, vol. 8.
Childs, B. et al., "Senescence and apoptosis: dueling or complementary cell fates?," EMBO Rep., 2014, pp. 1139-1153, vol. 15.
Citrin, D. et al., "Role of type II pneumocyte senescence in radiation-induced lung fibrosis," J. Natl. Can. Inst., 2013, pp. 1474-1484, vol. 105.
Coppe, J. et al., "The senescence-associated secretory phenotype: the dark side of tumor suppression," Annu. Rev. Pathol., 2010, pp. 99-118, vol. 5.
Cory, S. et al., "The Bcl2 family: regulators of the cellular life-or-death switch," Nat. Rev. Can., 2002, pp. 647-656, vol. 2.
Czabotar, P. et al., "Control of apoptosis by the BCL-2 protein family: implications for physiology and therapy," Nat. Rev. Mol. Cell Biol., 2014, pp. 49-63, vol. 15.
Debacq-Chainiaux, F. et al., "Protocols to detect senescence-associated beta-galactosidase (SA-betagal) activity, a biomarker of senescent cells in culture and in vivo," Nat. Protoc., 2009, pp. 1798-1806, vol. 4.
Demaria, M. et al., "An Essential Role for Senescent Cells in Optimal Wound Healing through Secretion of PDGF-AA," Dev. Cell, 2014, pp. 722-733, vol. 31.
Di Pietro, R. et al., "Ionnizing radition sensitizes erythroleukemic cells but not normal erythroblasts to tumor necrosis factor-related apoptosis-inducing ligand (TRAIL)-mediated cytotoxicity by selective up-regulation of TRAIL-R1," Blood, May 1, 2001, pp. 2596-2603, vol. 97, No. 9.
Dykstra, B. et al., "Clonal analysis reveals multiple functional defects of aged murine hematopoietic stem cells," J. Exp Med., 2011, pp. 2691-2703, vol. 208.
Fleenor, C. et al., "Ionizing radiation and hematopoietic malignancies: altering the adaptive landscape," Cell Cycle, 2010, pp. 3005-3011, vol. 9.

(56) References Cited

OTHER PUBLICATIONS

Geiger, H. et al., "Regulation of hematopoietic stem cell aging in vivo by a distinct genetic element," PNAS, 2005, pp. 5102-5107, vol. 102.
Geiger, H. et al., "The ageing haematopoietic stem cell compartment," Nat. Rev. Immunol., 2013, pp. 376-389, vol. 13.
Harfouche, G. et al., "Response of normal stem cells to ionizing radiation: a balance between homeostasis and genomic stability," Mutat. Res., 2010, pp. 167-174, vol. 704.
International Search Report and Written Opinion dated Sep. 18, 2015 from Patent Application No. PCT/US2015/029208; 13 pgs.
International Search Report and Written Opinion dated Oct. 23, 2015 from Patent Application No. PCT/US2015/041470; 9 pgs.
International Search Report and Written Opinion dated Apr. 1, 2016 from Patent Application No. PCT/US2016/014518; 9 pgs.
International Search Report and Written Opinion dated Apr. 1, 2016 from Patent Application No. PCT/US2016/014510; 12 pgs.
Janzen, V. et al., "Stem-cell ageing modified by the cyclin-dependent kinase inhibitor p16INK4a," Nature, 2006, pp. 421-426, vol. 443.
Jozefczuk, J. et al., "Preparation of Mouse Embryonic Fibroblast Cells Suitable for Culturing Human Embryonic and Induced Pluripotent Stem Cells," J. Vis. Exp., Jun. 2012, pp. 1-5, vol. 64, Issue e3854.
Laberge, R. et al., "Mitochondrial DNA damage induces apoptosis in senescent cells," Cell Death Dis., 2013, p. e2727, vol. 4.
Le, O. et al., "Ionizing radiation-induced long-term expression of senescence markers in mice is independent of p53 and immune status," Aging Cell, 2010, pp. 398-409, vol. 9.
Le Couteur, D. et al., "Aging biology and novel targets for drug discovery," J. Gerontol. A Biol. Sci. Med. Sci., 2012, pp. 168-174, vol. 67.
Lessene, G. et al., "Structure-guided design of a selective BCL-X(L) inhibitor," Nat. Chem. Biol., 2013, pp. 390-397, vol. 9.
Marcotte, R. et al., "Replicative senescence revisited," J. Gerontol. A Biol. Sci. Med. Sci., 2002, pp. B257-B269, vol. 57.
Meng, A. et al,. "Sphingomyelin synthase as a potential target for D609-induced apoptosis in U937 human monocytic leukemia cells," Exp. Cell Res., 2004, pp. 385-392, vol. 292.
Munoz-Espin, D. et al., "Cellular senescence: from physiology to pathology," Nat. Rev. Mol. Cell Biol., 2014, pp. 482-496, vol. 15.
Raj, L. et al., "Selective killing of cancer cells with a small molecule targeting stress response to ROS," HHS Public Access Author Manuscript, 2012, pp. 1-11, Published in final edited form as: Nature, pp. 231-234, vol. 475, No. 7355.
Ricci, M. et al., "Chemotherapeutic Approaches for Targeting Cell Death Pathways," The Oncologist, 2006, pp. 342-357, vol. 11.
Richardson, R., "Ionizing radiation and aging: rejuvenating an old idea," Aging, 2009, pp. 887-902, vol. 1.
Rudin, C. et al., "Phase II study of single-agent navitoclax (ABT-263) and biomarker correlates in patients with relapsed small cell lung cancer," Clin. Cancer Res., 2012, pp. 3163-3169, vol. 18.
Serrano, M. et al., "Oncogenic ras provokes premature cell senescence associated with accumulation of p53 and p16INK4a," Cell, 1997, pp. 593-602, vol. 88.
Serrano, M. et al., "Putting the stress on senescence," Curr. Opin. Cell Biol., 2001, pp. 748-753, vol. 13.
Shao, L. et al., "Total body irradiation causes long-term mouse BM injury via induction of HSC premature senescence in an Ink4a- and Arf-independent manner," Blood, 2014, pp. 3105-3115, vol. 123.
Shao, L. et al., "Hematopoietic stem cell injury induced by ionizing radiation," Antioxid. Redox Signal., 2014, pp. 1447-1462, vol. 20.
Sorrentino, J. et al., "p16INK4a reporter mice reveal age-promoting effects of environmental toxicants," J. Clin. Invest., 2014, pp. 169-173, vol. 124.
Souers, A. et al., "ABT-199, a potent and selective BCL-2 inhibitor, achieves antitumor activity while sparing platelets," Nat. Med., 2013, pp. 202-208, vol. 19.
Tchkonia, T. et al., "Cellular senescence and the senescent secretory phenotype: therapeutic opportunities," J. Clin. Invest., 2013, pp. 966-972, vol. 123.
Tse, C. et al., "ABT-263: a potent and orally bioavailable Bcl-2 family inhibitor," Can. Res., 2008, pp. 3421-3428, vol. 68.
Van Deursen, J., "The role of senescent cells in ageing," Nature, 2014, pp. 439-446, vol. 509.
Wang, Y. et al., "Inhibition of phosphatidylinostol 3-kinase uncouples H2O2-induced senescent phenotype and cell cycle arrest in normal human diploid fibroblasts," Exp. Cell Res., 2004, pp. 188-196, vol. 298, Elsevier Inc.
Wang, Y. et al., "Total body irradiation selectively induces murine hematopoietic stem cell senescence," Blood, Jan. 1, 2006, pp. 358-366, vol. 107, No. 1.
Wang, Y. et al., "Microrna Regulation of Ionizing Radiation-Induced Premature Senescence," Int. J. Radiation Oncology Biol. Phys., 2011, pp. 839-848, vol. 81, No. 3, Elsevier Inc.
Wang B. et al., "The Bcl-2/xL inhibitor ABT-263 increases the stability of Mcl-1 mRNA and protein in hepatocellular carcinoma cells," Molecular Cancer, 2014, pp. 1-11, vol. 13, No. 98.
Baar, M. et al., "Targeted Apoptosis of Senescent Cells Restores Tissue Homeostasis in Response to Chemotoxicity and Aging," HHS Public Access Author Manuscript, Mar. 23, 2018, pp. 1-37, published in final edited form as: Cell, Mar. 23, 2017, pp. 132-147, vol. 169, No. 1.
Baker, D. et al., "Naturally occurring p16Ink4a-positive cells shorten healthy lifespan," HHS Public Access Author Manuscript, Aug. 3, 2016, pp. 1-30, published in final edited form as: Nature, Feb. 11, 2016, pp. 184-189, vol. 530, No. 7589.
Blagosklonny, M., "Selective anti-cancer agents as anti-aging drugs," Cancer Biol. Ther., Dec. 2013, pp. 1092-1097, vol. 14, No. 12, Landes Bioscience.
Braun, H. et al., "Cellular Senescence Limits Regenerative Capacity and Allograft Survival," J. Am. Soc. Nephrol., Sep. 2012, pp. 1467-1473, vol. 23, No. 9.
Childs, B. et al., "Senescent cells: an emerging target for diseases of ageing," HHS Public Access Author Manuscript, May 9, 2018, pp. 1-41, published in final edited form as: Nat. Rev. Drug Discov., Oct. 2017, pp. 718-735, vol. 16, No. 10.
Lin, C. et al., "Endostatin and transglutaminase 2 are involved in fibrosis of the aging kidney," HHS Public Access Author Manuscript, Jun. 1, 2017, pp. 1-20, published in final edited form as: Kidney Int., Jun. 2016, pp. 1281-1292, vol. 89, No. 6.
Liu, J. et al., "Droxinostat, a Histone Deacetylase Inhibitor, Induces Apoptosis in Hepatocellular Carcinoma Cell Lines via Activation of the Mitochondrial Pathway and Downregulation of FLIP," Translational Oncology, Feb. 2016, pp. 70-78, vol. 9, No. 1, Elsevier Inc. on behalf of Neoplasia Press, Inc.
Matthews, C. et al., "Vascular Smooth Muscle Cells Undergo Telomere-Based Senescence in Human Atherosclerosis. Effects of Telomerase and Oxidative Stress," Cir. Res., Jul. 21, 2006, pp. 156-164, vol. 99.
Office Action dated Oct. 4, 2018 from related U.S. Appl. No. 15/545,480; 4 pgs.
Schafer, M. et al., "Targeting Senescent Cells in Fibrosis: Pathology, Paradox, and Practical Considerations," Curr. Rheumatol. Rep., Jan. 26, 2018, Article 3, vol. 20, Issue 1, SpringerLink, Abstract Only.
Son, D. et al., Piperlongumine inhibits atherosclerotic plaque formation and vascular smooth muscle cell proliferation by suppressing PDGF receptor signaling, Biochem. Biophys. Res. Commun., 2012, pp. 349-354, vol. 427.
Valentijn, F. et al., "Cellular senescence in the aging and diseased kidney," J. Cell Commun. Signal., 2018, pp. 69-82, vol. 12, Springer.
Van Willigenburg, H. et al., "Cellular senescence as a therapeutic target to improve renal transplantation outcome," Pharmacol. Res., Apr. 2018, pp. 322-330, vol. 130.
Yao, L. et al., "Piperlongumine alleviates lupus nephritis in MRL-Fas(lpr) mice by regulating the frequency of Th17 anti regulatory T cells," Immunol. Lett., Sep. 2014, pp. 76-80, vol. 161, No. 1, Abstract Only.
Aguilar, A., et al., "A Potent and Highly Efficacious Bcl-2/Bcl-xL Inhibitor," J. Med. Chem., 2013, pp. 3048-3067, vol. 56.
Bai, L., et al., "BM-1197: A Novel and Specific Bcl-2/Bcl-xL Inhibitor Inducing Complete and Long-Lasting Tumor Regression In Vivo," PLOS One, Jun. 2014, pp. 1-13, vol. 9, No. 6, e99404.

(56) References Cited

OTHER PUBLICATIONS

Bajwa, N., et al., "Inhibitors of the anti-apoptotic Bcl-2 proteins: a patent review," NIH Public Access Author Manuscript, Jan. 17, 2013, pp. 1-25, published in final edited form as: Expert Opin. Ther. Pat., Jan. 2012, pp. 37-55, vol. 22, No. 1.
Brenkman, A. et al., "Mdm2 Induces Mono-Ubiquitination of FOXO4," PLOS One, Jul. 2008, pp. 1-7, vol. 3, No. 7, e2819.
Bruncko, M., et al., "Studies Leading to Potent, Dual Inhibitors of Bcl-2 and Bcl-xL," J. Med. Chem., 2007, pp. 641-662, vol. 50, No. 4.
Bruncko, M., et al., "Structure-Guided Design of a Series of MCL-1 Inhibitors with High Affinity and Selectivity," J. Med. Chem., 2015, pp. 2180-2194, vol. 58, No. 5.
Chang, J. et al., "Clearance of senescent cells by ABT263 rejuvenates aged hematopoietic stem cells in mice," Nat. Med., Jan. 2016, pp. 78-83, vol. 22, No. 1.
Chen, L. et al., "p53 alpha-Helix mimetics antagonize p53/MDM2 interaction and activate p53," Mol. Cancer Ther., Jun. 2005, pp. 1019-1025, vol. 4, No. 6.
Chen, J. et al., "Structure-Based Discovery of BM-957 as a Potent Small-Molecule Inhibitor of Bcl-2 and Bcl-xL Capable of Achieving Complete Tumor Regression," NIH Public Access Author Manuscript, Oct. 11, 2013, pp. 1-33, published in final edited form as: J. Med. Chem., Oct. 11, 2012, pp. 8502-8514, vol. 55, No. 19.
Delbridge, A. et al., "Thirty years of BCL-2: translating cell death discoveries into novel cancer therapies," Nat. Rev. Cancer, Feb. 2016, pp. 99-109—vol. 16.
Galatin, P. et al., "A Nonpeptidic Sulfonamide Inhibits the p53-mdm2 Interaction and Activates p53-Dependent Transcription in mdm2-Overexpressing Cells," J. Med. Chem., 2004, pp. 4163-4165, vol. 47, No. 17.
Gustafson, J. et al., "Small-Molecule-Mediated Degradation of the Androgen Receptor through Hydrophobic Tagging," Angew. Chem. Int. Ed., Aug. 10, 2015, pp. 9659-9662, vol. 54, No. 33.
Lessene, G., et al., "BCL-2 family antagonists for cancer therapy," Nat. Rev. Drug Discov., Dec. 2008, pp. 989-1000, vol. 7.
Lu, Y. et al., "Discovery of a Nanomolar Inhibitor of the Human Murine Double Minute 2 (MDM2)-p53 Interaction through an Integrated, Virtual Database Screening Strategy," J. Med. Chem., 2006, pp. 3759-3762, vol. 49, No. 13.
Lu, J., et al., "Hijacking the E3 Ubiquitin Ligase Cereblon to Efficiently Target BRD4," Chem. Biol., Jun. 18, 2015, pp. 755-763, vol. 22.
Park, C-M. et al., "Discovery of an Orally Bioavailable Small Molecule Inhibitor of Prosurvival B-Cell Lymphoma 2 Proteins," J. Med. Chem., 2008, pp. 6902-6915, vol. 51, No. 21.
Pelz, N. et al., "Discovery of 2-Indole-acylsulfonamide Myeloid Cell Leukemia 1 (Mcl-1) Inhibitors Using Fragment-Based Methods," J. Med. Chem., 2016, pp. 2054-2066, vol. 59.
Sleebs, B. et al., "Quinazoline Sulfonamides as Dual Binders of the Proteins B-Cell Lymphoma 2 and B-Cell Lymphoma Extra Long with Potent Proapoptotic Cell-Based Activity," J. Med. Chem., 2011, pp. 1914-1926, vol. 54, No. 6.
Sleebs, B. et al., "Discovery of Potent and Selective Benzothiazole Hydrazone Inhibitors of Bcl-XL," J. Med. Chem., 2013, pp. 5514-5540, vol. 56, No. 13.
Stoll, R. et al., "Chalcone Derivatives Antagonize Interactions between the Human Oncoprotein MDM2 and p53," Biochem., 2001, pp. 336-344, vol. 40.
Tanaka, Y. et al., "Discovery of Potent Mcl-1/Bcl-xL Dual Inhibitors by Using a Hybridization Strategy Based on Structural Analysis of Target Proteins," J. Med. Chem., 2013, pp. 9635-9645, vol. 56, No. 23.
Tao, Z-F. et al., "Discovery of a Potent and Selective BCL-XL Inhibitor with in Vivo Activity," ACS Med. Chem. Lett., 2014, pp. 1088-1093, vol. 5.
Vogler, M. et al., "Bcl-2 inhibitors: small molecules with a big impact on cancer therapy," Cell Death Differ., 2009, pp. 360-367, vol. 16.
Vogler, M., Targeting BCL2-Proteins for the Treatment of Solid Tumours, Adv. Med., 2014, pp. 1-14, Article ID 943648, Hindawi Publishing Corporation.
Yin, H. et al., "Terphenyl-Based Helical Mimetics That Disurpt the p53/HDM2 Interaction," Angew. Chem. Int. Ed., Apr. 2005, pp. 2704-2707, vol. 44, No. 18, Wiley-VCH Verlag GmbH & Co. KGaA, Weinheim.
Zhou, H. et al., "Design of Bcl-2 and Bcl-xL Inhibitors with Subnanomolar Binding Affinities Based Upon a New Scaffold," NIH Public Access Author Manuscript, May 24, 2013, pp. 1-42, published in final edited form as: J. Med. Chem., May 24, 2012, pp. 4664-4682, vol. 55, No. 10.
Zhou, H. et al., "Structure-based Design of Potent Bcl-2/Bcl-xL Inhibitors with Strong in vivo Antitumor Activity," NIH Public Access Author Manuscript, Jul. 12, 2013, pp. 1-31, published in final edited form as: J. Med. Chem., Jul. 12, 2012, pp. 6149-6161, vol. 55, No. 13.
Zhu, Y. et al., "The Achilles' heel of senescent cells: from transcriptome to senolytic drugs," Aging Cell, Aug. 2015, pp. 644-658, vol. 14, No. 4.
Zhu, Y. et al., Identification of a novel senolytic agent, navitoclax, targeting the Bcl-2 family of anti-apoptotic factors, Aging Cell, Jun. 2016, pp. 428-435, vol. 15, No. 3.
Kirkland, J. et al., "Clinical strategies and animal models for developing senolytic agents," Exp. Gastroenterol., 2015, pp. 19-25, vol. 68, Elsevier Inc.
Office Action dated Apr. 17, 2019 from related U.S. Appl. No. 15/545,480; 15 pgs.
Tampe, D. et al., "Potential approaches to reverse or repair renal fibrosis," Nat. Rev. Nephrol., Apr. 2014, pp. 226-237, vol. 10.
International Search Report and Written Opinion dated Apr. 26, 2019 from related International Patent Application No. PCT/US2019/014545; 10 pgs.
Berg, C. et al., "Human mature red blood cells express caspase-3 and caspase-8, but are devoid of mitochondrial regulators of apoptosis," Cell Death and Differentiation, 2001, pp. 1197-1206, vol. 8.
Gottlieb, Y. et al., "Physiologically aged red blood cells undergo erythrophagocytosis in vivo but not in vitro," Haematologica, 2012, pp. 994-1002, vol. 97, No. 7.
Mason, K. et al., "Programmed Anuclear Cell Death Delimits Platelet Life Span," Cell, Mar. 2007, pp. 1173-1186, vol. 128.
Office Action dated Sep. 3, 2019 from related Chinese Patent Application No. 201580035221.5; 91 pgs.
Office Action dated Oct. 16, 2019 from related U.S. Appl. No. 15/545,480; 15 pgs.
Office Action dated Nov. 13, 2019 from related U.S. Appl. No. 16/057,021; 6 pgs.
Yadav, V. et al., "Remediation of Hemorrhagic Shock-Induced Intestinal Barrier Dysfunction by Treatment with Diphenyldihaloketones EF24 and CLEFMA," J. Pharmacol. Exp. Ther., Nov. 2014, pp. 413-422, vol. 351.
Office Action dated Feb. 25, 2020 from related U.S. Appl. No. 16/057,021; 5 pgs.
Office Action dated Mar. 2, 2020 from related U.S. Appl. No. 15/545,480; 10 pgs.
Notice of Allowance dated Apr. 30, 2020 from related U.S. Appl. No. 16/057,021; 5 pgs.
Extended European Search Report dated Jul. 6, 2020 from related European Patent Application No. 19216987.8; 10 pgs.
Office Action dated Aug. 11, 2020 from related U.S. Appl. No. 15/545,480; 11 pgs.
Office Action dated Sep. 1, 2020 from related Chinese Patent Application No. 201580035221.5; 10 pgs., with English translation.
Cohen, J. et al., "Astrocyte Senescence and Metabolic Changes in Response to HIV Antiretroviral Therapy Drugs," Front. Aging Neurosci., Aug. 2017, vol. 9, No. 281.
Desai, S. et al., "Early Immune Senescence in HIV Disease," Curr. HIV/AIDS Rep., 2010, pp. 4-10, vol. 7.
Office Action dated Dec. 28, 2020 from related U.S. Appl. No. 15/545,480; 16 pgs.
Omori, S. et al., "Generation of a p16 Reporter Mouse and Its Use to Characterize and Target p16high Cells In Vivo," Cell Metab., Nov. 3, 2020, pp. 814-828, vol. 32.

(56) References Cited

OTHER PUBLICATIONS

Yang, C. et al., "The Curcumin Analog EF24 Targets NF-kB and miRNA-21, and Has Potent Anticancer Activity In Vitro and In Vivo," PLOS One, Aug. 2013, pp. 1-12, vol. 8, No. 8, e71130.

Yu, C. et al., "HIV and drug abuse mediate astrocyte senescence in a beta-catenin-dependent manner leading to neuronal toxicity," Aging Cell, 2017, pp. 956-965, vol. 16.

Mercurio, L. et al., "Intracellular Insulin-like growth factor binding protein 2 (IGFBP2) contributes to the senescence of keratinocytes in psoriasis by stabilizing cytoplasmic p21," Aging, 2020, pp. 6823-6851, vol. 12, No. 8.

Notice of Allowance dated May 7, 2021 from related Chinese Patent Application No. 201580035221.5; 4 pgs.

Office Action dated Jan. 5, 2021 from related Chinese Patent Application No. 201580035221.5; 10 pgs.

Office Action dated Jun. 1, 2021 from related U.S. Appl. No. 15/545,480; 15 pgs.

Reid, J. et al., "Mouse pharmacokinetics and metabolism of the curcumin analog, 4-piperidinone,3,5-bis[)2-fluorophenyl)methylene]-acetate(3E,5E) (EF-24; NSC 716993)," Cancer Chemother. Pharmacol., 2014, pp. 1137-1146, vol. 73.

Scanbur Research Models & Services, 2019, 110 pgs., retrieve from: https://www.scanbur.com/Files/Images/Research/RMS-SCB-2019-WEB.pdf.

Swift, S. et al., "Acute Toxicity of Subcutaneously Administered Vitamin E Isomers Delta- and Gamma-Tocotrienol in Mice," Int. J. Toxicol., 2014, pp. 450-458, vol. 44, No. 6.

Communication under Rule 71(e) EPC (Notice of Allowance) dated Jul. 15, 2019 from related European Patent Application No. 15789264.7; 7 pgs.

Office Action dated Jun. 11, 2019 from related European Patent Application No. 15789264.7; 4 pgs.

Office Action dated Jun. 26, 2019 from related U.S. Appl. No. 16/057,021; 10 pgs.

* cited by examiner

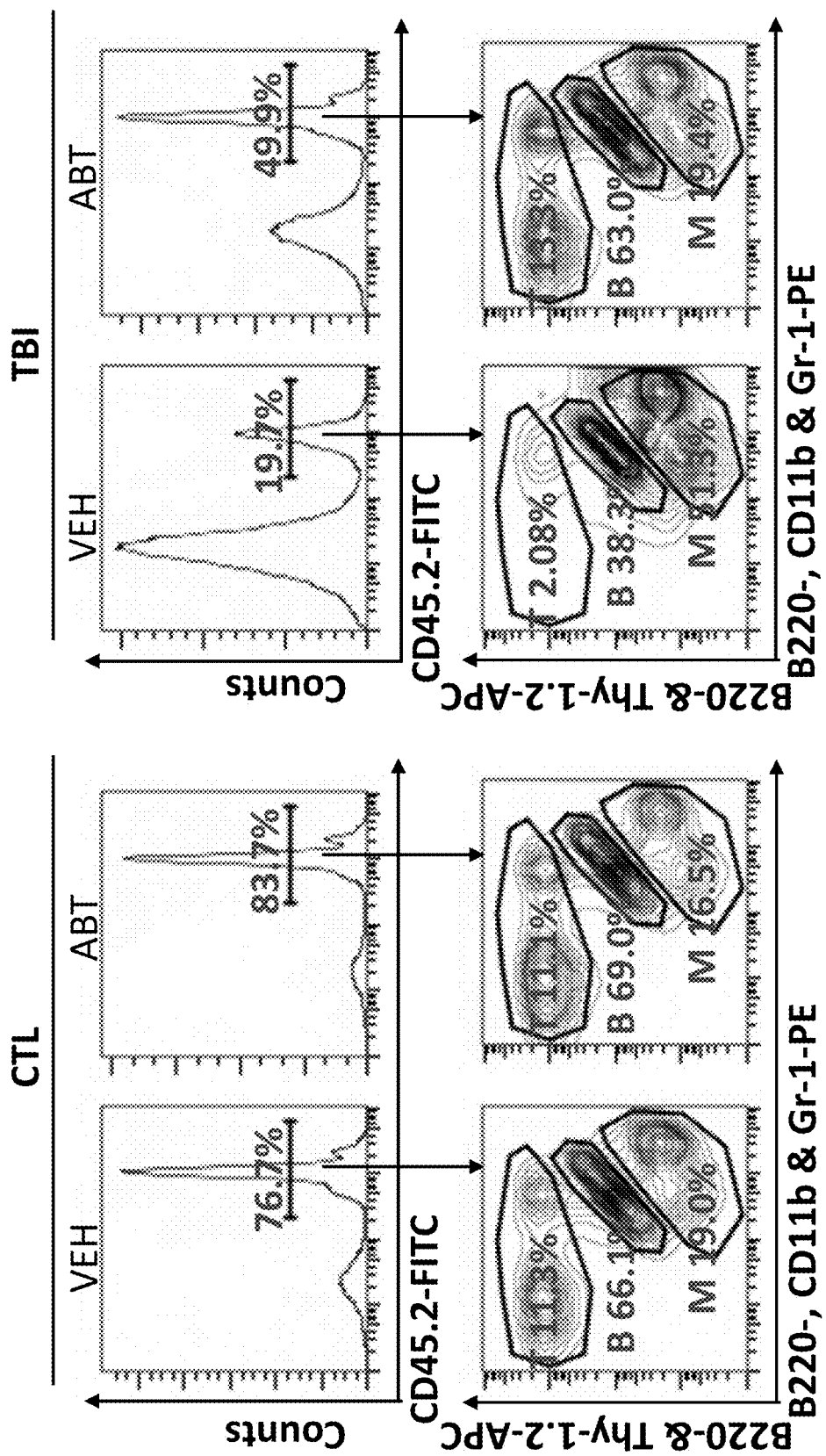

US 11,331,328 B2

COMPOSITIONS AND METHODS FOR INHIBITING ANTIAPOPTOTIC BCL-2 PROTEINS AS ANTI-AGING AGENTS

CROSS REFERENCE TO RELATED APPLICATIONS

This application claims the benefit of PCT Application PCT/US2015/029208, filed May 5, 2015, which claims the benefit of U.S. provisional application No. 61/988,705, filed May 5, 2014, each of the disclosures of which is hereby incorporated by reference in its entirety.

GOVERNMENTAL RIGHTS

This invention was made with government support under R01 CA122023 awarded by the National Institutes of Health. The government has certain rights in the invention.

FIELD OF THE INVENTION

The present invention relates Bcl-2 inhibitors and their method of use in the treatment and prevention of diseases and pathologies related to accumulation of senescent cells during aging, such as cancer, chronic obstructive pulmonary disease (COPD), osteoarthritis, atherosclerosis, neurodegenerative diseases, diabetes, and many others. The present invention also relates to pharmaceutical compositions containing these compounds as well as various uses thereof.

BACKGROUND OF THE INVENTION

Age is a leading risk factor for many human diseases, including most cancers, atherosclerosis, neurodegenerative diseases, diabetes, and many others. An increasing body of evidence demonstrates that aging is associated with an accumulation of senescent cells. When a cell becomes senescent, it loses its reproductive function, which may cause tissue degeneration. In addition, senescent cells produce increased levels of free radical and various inflammatory mediators that can induce tissue damage and cell transformation. Therefore, selective depletion of senescent cells may be a novel anti-aging strategy that may prevent cancer and various human diseases associated with aging and rejuvenate the body to live a healthier lifespan. This assumption is supported by a recent study showing that selective depletion of senescent cells in the BubR1 progeroid mouse model by a genetic approach resulted in the delay of various age-related pathologies and disorders. However, there is no drug that can selectively deplete senescent cells. Therefore, a method to selectively deplete senescent cells is needed.

SUMMARY OF THE INVENTION

In one aspect, the invention encompasses a method of selectively killing senescent cells in a cell sample. The method comprises detecting senescent cells in a cell sample, administering a composition comprising at least one inhibitor of one or more anti-apoptotic proteins in the Bcl-2 family to the cells, wherein the inhibitor selectively kills senescent cells, and measuring cell death of senescent cells.

In another aspect, the invention encompasses a method to delay at least one feature of aging in a subject. The method comprises administering a composition comprising a therapeutically effective amount of at least one inhibitor of one or more anti-apoptotic proteins in the Bcl-2 family to a subject.

In still another aspect, the invention encompasses treating an age-related disease or condition. The method comprises administering a composition comprising a therapeutically effective amount of at least one inhibitor of one or more anti-apoptotic proteins in the Bcl-2 family to a subject in need thereof.

In still yet another aspect, the invention encompasses a method of killing therapy-induced senescent cells. The method comprises administering a composition comprising a therapeutically effective amount of at least one inhibitor of one or more anti-apoptotic proteins in the Bcl-2 family to a subject that has received DNA-damaging therapy, and killing therapy induced-senescent cells in normal and tumor tissues following DNA-damaging therapy.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A, FIG. 1B, FIG. 1C, FIG. 1D) ABT263 dose-dependently kills human WI-38 fibroblasts (WI38) induced to senesce by ionizing radiation (IR-SC; FIG. 1B), replicative exhaustion (Rep-SC; FIG. 1C), or expression of oncogenic Ras (Ras-SC; FIG. 1D), but is not cytotoxic to non-senescent WI-38 cells (NC; FIG. 1A). (FIG. 1E, FIG. 1F) ABT263 kills IR-induced senescent WI-38 cells (IR-SC) in a time-dependent manner. Viable cells were quantified after cells were incubated with 1.25 µM ABT263 for the indicated number of hours (FIG. 1E) or 72 h after the cells were incubated with 1.25 µM ABT263 for the indicated durations (FIG. 1F). (FIG. 1G, FIG. 1H) ABT263 kills IR-induced senescent cells (IR-SC) but not non-senescent cells (NC) in a dose-dependent, but cell type- and species-independent manner. Viable cells were quantified after cells were treated with increasing concentrations of ABT263 for 72 h. (FIG. 1G) IMR-90, human IMR-90 fibroblasts; (FIG. 1H) REC, human renal epithelial cells (REC); (FIG. 1I) MEF, mouse embryonic fibroblasts. The data presented are means±SEM of viable cells as a percent of control without ABT263 treatment from 3 or more independent experiments. *, $p<0.05$; , $p<0.01$; and *, $p<0.001$, vs. without ABT263 for FIG. 1A, FIG. 1B, FIG. 1C, FIG. 1D, FIG. 1E, FIG. 1F; and; , $p<0.01$; *, $p<0.001$; and ***, $p<0.001$, vs. their respective NC treated with the same concentrations of ABT263 for FIG. 1G, FIG. 1H, FIG. 1I. One way ANOVA for FIG. 1A, FIG. 1B, FIG. 1C, FIG. 1D, FIG. 1E, FIG. 1F and two-way ANOVA for FIG. 1G, FIG. 1H, FIG. 1I.

(FIG. 2A, FIG. 2B) ABT263 induces apoptosis in IR-induced senescent WI38 cells in a caspase-dependent manner. (FIG. 2A) representative flow cytometric analyses of apoptosis in IR-induced senescent WI-38 cells treated with vehicle (VEH) or 1.25 µM ABT263 for 24 h in the presence or absence of the pan-caspase inhibitor Q-VD-Oph (QVD, 20 µM). II=viable cells ($PI^-$ and Annexin $V^-$); III=early apoptotic cells ($PI^-$ and Annexin $V^+$); and IV=late apoptotic cells ($PI^+$ and Annexin $V^+$). (FIG. 2B) percentages of viable, early apoptotic, and late apoptotic cells from FIG. 2A. Similar results were observed in two additional experiments. (FIG. 2C) Caspase inhibition by QVD abrogates ABT263-induced cell death in IR-induced senescent WI-38 cells. Viable cells were quantified after treatment as in FIG. 2A for 72 h. (FIG. 2D) ABT263 does not activate caspase 8 and receptor-interacting protein 1 (RIP1) in non-senescent WI-38 cells (NC) or IR-induced senescent WI-38 cells (IR-SC). Cells were treated with vehicle (VEH) or 1.25 µM ABT263 (ABT) for 24 h and lysates analyzed by western blotting. CTL is a positive control using lysates from Jurkat cells treated with 25 µM etopside for 6 h. Procasp-8, procaspase-8; cCasp-8, cleaved caspase-8; and cRIP1, cleaved RIP1. (FIG. 2E, FIG. 2F) ABT263 selectively activates caspase 3 in IR-induced senescent WI-38 cells (IR-SC) but not non-senescent WI-38 cells (NC). Cells were treated with vehicle (VEH) or 1.25 µM ABT263 (ABT) for 24 h. Representative western blots of procaspase-3 (Procasp-3), cleaved caspase-3 (cCasp-3), and β-actin are presented in FIG. 2E and densitometry quantification of procaspase 3 expression relative to β-actin is presented in FIG. 2F. CTL is a positive control using the cell lysates from Jurkat cells treated with 0.25 mg/ml cytochrome C for 1 h. (FIG. 2G) Exposure of WI-38 cells to IR increases senescence associated β-galactosidase (SA-β-gal) activity and sensitivity to ABT263 in a time-dependent manner. Open bars show percentages of SA-β-gal$^+$ cells at various times after exposure to 10 Gy IR. Black bars show percent viable cells after the irradiated cells were harvested at various times after irradiation and incubated with 1.25 µM ABT263 for 72 h. (FIG. 2H, FIG. 2I, FIG. 2J, FIG. 2K) Densitometry quantification of western analyses of Bcl-2 (FIG. 2H), Bcl-xl (FIG. 2I), Bak (FIG. 2J) and Bax (FIG. 2K) expression in WI-38 cells at various times after exposure to 10 Gy IR from analyses presented in FIG. 7A. (FIG. 2L, FIG. 2M) Inhibition of both Bcl-2 and Bcl-xl are required to selectively kill senescent cells. Viable WI-38 cells were determined after non-senescent (NC; FIG. 2L) and IR-induced senescent (IR-SC; FIG. 2M) cells were incubated with vehicle (VEH), 5 µM ABT199, 0.5 µM WEHI539, or ABT199 plus WEHI539 for 72 h. (FIG. 2N) Knockdown of both Bcl-2 and Bcl-xl are required to selectively kill senescent cells. Viable WI38 cells were determined 72 h after non-senescent (NC) and IR-induced senescent (IR-SC) cells were infected with lentiviruses carrying control shRNA (CTL), Bcl-2 shRNA, Bcl-xl shRNA, or Bcl-2 and Bcl-xl shRNA. The data are presented as means±SEM of 3 independent experiments except those in FIG. 2N in which n=5. *, $p<0.05$; , $p<0.01$; *, $p<0.001$; and ****, $p<0.0001$ vs their respective controls. One-way ANOVA for FIG. 2H, FIG. 2I, FIG. 2JK and two-way ANOVA for FIG. 2C, FIG. 2F, FIG. 2G, FIG. 2L, FIG. 2M, FIG. 2N.

(FIG. 3A) A diagram illustrating the experimental design. Briefly, groups of 2 mo old male p16-3MR mice were sham irradiated (CTL) or exposed to 6 Gy TBI. Sixteen wks after irradiation, they received 2 cycles of treatment with vehicle (VEH), ganciclovir (GCV, 25 mg/kg/d for 5 days per cycle, ip), or ABT263 (ABT, 50 mg/kg/d for 7 days per cycle, po) with an interval of 2 weeks between the treatment cycles. One day after treatment, whole body luminescence was quantified as described in Methods. The next day, mice were euthanized to harvest lungs for tissue luminescence quantification and analysis of p16, IL-1α, TNFα, CCL-5 and CXCL-10 mRNA levels by qRT-PCR. (FIG. 3B, FIG. 3C) Whole body luminescence imaging shows that ABT263 can clear senescent cells in TBI p16-3MR mice as effectively as ganciclovir. Representative luminescent images of control (CTL) and TBI p16-3MR mice (TBI) are shown in FIG. 3B. A normal wild-type C57BL/6 mouse (WT) was included as a negative control for the imaging. Whole body luminescence quantification is shown in FIG. 3C. (FIG. 3D, FIG. 3E, FIG. 3F) ABT263 can clear senescent cells in lungs from TBI p16-3MR mice as effectively as ganciclovir. Representative luminescent images of the lungs from control (CTL) and TBI p16-3MR mice (TBI) are shown in FIG. 3D. Lung luminescence quantification is shown in FIG. 3E. Expression of p16 mRNA in lungs is shown in FIG. 3F. (FIG. 3G, FIG. 3H, FIG. 3I, FIG. 3J) Analysis of IL-1α(FIG. 3G), TNFα (FIG. 3H), CCL-5 (FIG. 3I), and CXCL-10 (FIG. 3J) mRNA levels in the lungs demonstrates that ABT263 and ganciclovir are equally effective at inhibiting the TBI-induced SASP in p16-3MR mice. The data are presented as means±SEM. N=4-8 mice/group for FIG. 3C, 3-5 for FIG. 3E, FIG. 3F, and 4 for FIG. 3G, FIG. 3H, FIG. 3I, FIG. 3J. , $p<0.01$ and *, $p<0.001$, vs CTL. Two-way ANOVA.

FIG. 4A, FIG. 4B, FIG. 4C, FIG. 4D, FIG. 4E, FIG. 4F, FIG. 4G, FIG. 4H, FIG. 4I, FIG. 4J, FIG. 4K, FIG. 4L, FIG. 4M, FIG. 4N and FIG. 4O depict schematics, graphs and flow cytometry plots showing ABT263 can clear senescent HSCs in vivo to mitigate TBI-induced premature hematopoietic aging and LT-BM injury. (FIG. 4A) A diagram illustrating the experimental design. Briefly, groups of 2 mo old male C57BL/6 mice were sham irradiated (CTL) or exposed to 6 Gy TBI. Eight weeks after irradiation, they received 2 cycles of treatment with vehicle (VEH), ganciclovir (GCV, 25 mg/kg/d for 5 days per cycle, ip), or ABT263 (ABT, 50 mg/kg/d for 7 days per cycle, ip) with an interval of 2 wks between the treatment cycles. Five wks after treatment, mice were euthanized to harvest bone marrow cells for analysis of HSC senescence and function by day-35 CAFC assay and bone marrow transplantation (BMT). (FIG. 4B, FIG. 4C) Analysis of p16 mRNA levels (FIG. 4B) and SA-β-gal staining (FIG. 4C) in HSC demonstrates that treatment with ABT263 clears senescent HSCs induced by TBI. The data are presented as means±SEM (n=3 and 4 independent assays for p16 mRNA and SA-β-gal staining, respectively). a, $p<0.05$ vs CTL. n.d, not detectable. (FIG. 4D) ABT263 treatment improves the clonogenic function of HSCs from irradiated mice. The data are presented as means±SEM (n=3 independent assays). a, $p<0.01$ vs. CTL. (FIG. 4E, FIG. 4F, FIG. 4G, FIG. 4H, FIG. 4I, FIG. 4J, FIG. 4K, FIG. 4L, FIG. 4M, FIG. 4N, FIG. 4O) Competitive and serial BMT demonstrates that ABT263 treatment can mitigate TBI-induced premature hematopoietic aging and LT-BM injury by improving the ability of irradiated HSCs to self-renew and produce long-term and balanced multi-lineage engraftment in lethally irradiated recipients. (FIG. 4E) A diagram illustrating the competitive and serial BMT. (FIG. 4F, FIG. 4G) Representative flow cytometric analyses of total donor-derived white blood cell (CD45.2$^+$ cells), T cell (CD45.2$^+$Thy-1.2$^+$ cells), B cell (CD45.2$^+$B220$^+$ cells), and myeloid cell (M cells, CD45.2$^+$CD11b/Gr-1$^+$ cells) engraftment in a recipient's peripheral blood after primary BMT. (FIG. 4H, FIG. 4I, FIG. 4J, FIG. 4K, FIG. 4L, FIG. 4M, FIG. 4N, FIG. 4O) Engraftment of total donor-derived white blood cells (CD45.2$^+$ cells; FIG. 4H, FIG. 4L), T cells (CD45.2$^+$Thy-1.2$^+$ cells; FIG. 4I, FIG. 4M), B cells (CD45.2$^+$B220$^+$ cells; FIG. 4J, FIG. 4N), and myeloid cells (M cells, CD45.2$^+$CD11b/Gr-1$^+$ cells; FIG. 4K, FIG. 4O) in primary and secondary recipients' peripheral blood, respectively. The data are presented as means±SEM (6 recipients per group). a, p<0.05 vs. CTL and b, p<0.05 vs TBI+VEH. Two-way ANOVA.

(FIG. 5A) Representative phase contrast, BrdU staining, and SA-β-gal staining micrographs of non-senescent WI-38 cells (NC) and senescent WI-38 cells induced by IR (IR-SC), replicative exhaustion (Rep-SC), and expression of oncogenic Ras (Ras-SC) are shown. (FIG. 5B) IR-SC, Rep-SC, and Ras-SC express increased levels of p16 and p21 compared to NC. The data are presented as means±SEM of fold changes from three independent experiments. , p<0.01 and *, p<0.01 vs NC. Student's t test.

(FIG. 6A, FIG. 6B) MTT assay and (FIG. 6C, FIG. 6D) trypan blue exclusion test confirm that ABT263 can dose-dependently kill senescent WI-38 fibroblasts (WI38) induced by ionizing radiation (IR-SC; FIG. 6B and FIG. 6D), replicative exhaustion (Rep-SC), or expression of oncogenic Ras (Ras-SC), but is not cytotoxic to non-senescent WI-38 cells (NC; FIG. 6A and FIG. 6C). Viable cells were quantified after treating with increasing concentrations of ABT263 for 72 h. The data presented are means±SEM of viable cells as a percent of control without ABT263 treatment from 3 or more independent experiments, , p<0.01; and *, p<0.001, vs without ABT263. One-way ANOVA.

(FIG. 8A, FIG. 8B) ABT199 (a specific Bcl-2 inhibitor) is not cytotoxic to senescent WI-38 cells induced by ionizing radiation (IR-SC; FIG. 8B) or non-senescent WI-38 cells (NC; FIG. 8A). (FIG. 8C, FIG. 8D) WEHI539 (a specific Bcl-xl inhibitor) does not selectively kill IR-SC. Viable cells were quantified after treatment with increasing concentrations of ABT199 or WEHI593 for 72 h. The data presented are means±SE of viable cells as a percent of control without ABT199 or WEHI593 treatment from 3 independent experiments. ***, p<0.001, vs without ABT199 or WEHI593. One-way ANOVA.

(FIG. 9A) A diagram depicting the p16-3MR transgene. (FIG. 9B) A diagram illustrating the experimental design. Specifically, male p16-3MR mice were exposed to a sublethal dose (6 Gy) of TBI at 2 mos of age. Two, 4, and 6 mos after TBI, whole body luminescence was quantified as described in Methods. The mice were euthanized the day after the last imaging to harvest tissues for luminescence quantification and analysis of p16 mRNA levels by qRT-PCR. (FIG. 9C, FIG. 9D) Whole body luminescence imaging shows that TBI induces SC accumulation in p16-3MR mice in a time dependent manner. (FIG. 9C) Representative luminescent images of control (CTL) and TBI p16-3MR mice (TBI). (FIG. 9D) Whole body luminescence quantification. (FIG. 9F) Representative luminescent images of lungs, skeletal muscle, brain, liver and heart from control (CTL) and TBI p16-3MR mice. The numbers below the images are means±SEM of fold changes of luminescence in various tissues compared to that of CTL. (FIG. 9E) Analysis of p16 mRNA levels in the lungs, skeletal muscle, and brain confirms that TBI increases senescent cells in these tissues. The data are presented as means±SEM of fold changes from CTL (n=3 mice/group). *, p<0.05, vs CTL. One-way ANOVA for FIG. 9D and Student's t test for FIG. 9E.

(FIG. 10A, FIG. 10B) A diagram illustrating the strategy to isolate mouse bone marrow HSCs from control unirradiated mice (CTL) and sublethally total body irradiated (TBI) mice for analysis of HSC senescence and single HSC clonogenic activity. (FIG. 10C, FIG. 10D) HSCs from TBI mice express higher levels of p16 and p21 mRNA and SA-β-gal activity than cells from control unirradiated mice (CTL). The data are presented as means±SEM of fold changes from 3 independent experiments for FIG. 10C and means±SEM of percent of SA-β-gal$^+$ cells from 4 CTL mice and 3 TBI mice for FIG. 10D. , p<0.01 and *, p<0.001 vs CTL. (FIG. 10E) Clonogenic activity was determined after individual bone marrow HSCs were cultured at 1 cell/well in HSC expansion medium with vehicle (VEH) or ABT263 (ABT, 1.25 μM) for 7 d. The data presented in FIG. 10D are means±SEM of percent of single cells having the ability to form a large colony (>10,000 cells) from 2 independent experiments with pooled HSCs from 3-4 mice per group. **, p<0.01. Student's t test for FIG. 10C, FIG. 10D and two-way ANOVA for FIG. 10E.

(FIG. 11A, FIG. 11B) Representative flow cytometric analyses of HSCs and HPCs in bone marrow mononuclear cells (BMCs) from control (CTL) or TBI mice after treatment with vehicle (VEH; FIG. 11A) or ABT263 (ABT; FIG. 11B) as shown in FIG. 4A. (FIG. 11C, FIG. 11D) The frequencies of HPCs (FIG. 11C) and HSCs (FIG. 11D) in BMCs. (FIG. 11E, FIG. 11F) The numbers of HPCs (FIG. 11E) and HSCs (FIG. 11F) in the hind legs from each mouse. The data are presented as means±SEM (8-11 mice per group).

(FIG. 12A) Representative flow cytometric analyses of the cell cycle distribution of HSCs from control (CTL) or TBI mice after treatment with vehicle (VEH) or ABT263 (ABT). (FIG. 12B) The percentages of $G_0$ HSCs (Ki67$^-$ cells). (FIG. 12D) Representative flow cytometric analyses of γH2AX staining to detect DNA double strand breaks in HSCS from control (CTL) or TBI mice after treatment with vehicle (VEH) or ABT263 (ABT). (FIG. 12C) The mean fluorescence intensity (MFI) of HSC γH2AX staining. The data are presented as means±SEM (n=8-11 mice per group for FIG. 12A and 5-11 mice per group for FIG. 12B). FIG. 12A, p<0.05 vs CTL and FIG. 12B, p<0.05 vs TBI+VEH. Two-way ANOVA.

(FIG. 13A, FIG. 13B) Representative flow cytometric analyses of B cells (B220$^+$ cells), mature B cells (MB, B220$^+$IgM$^+$CD93$^-$ cells), immature B cells (IB, B220$^+$IgM$^+$CD93$^+$ cells), and Pre-Pro-B cells (PB, B220$^+$IgM$^-$CD93$^-$ cells) in bone marrow mononuclear cells (BMC) from control (CTL) or TBI mice after treatment with vehicle (VEH; FIG. 13A) or ABT263 (ABT; FIG. 13B) as shown in FIG. 4A. (FIG. 13C, FIG. 13D, FIG. 13E, FIG. 13F) The frequencies of B cells (FIG. 13C), mature B cells (MB, B220$^+$IgM$^+$CD93$^-$ cells; FIG. 13D), immature B cells (IB, B220$^+$IgM$^+$CD93$^+$ cells; FIG. 13E), and Pre-Pro-B cells (PB, B220$^+$IgM$^-$CD93$^-$ cells; FIG. 13F) in BMC are presented as means±SEM (4-6 mice per group). Two-way ANOVA.

DETAILED DESCRIPTION OF THE INVENTION

Figure 1A:
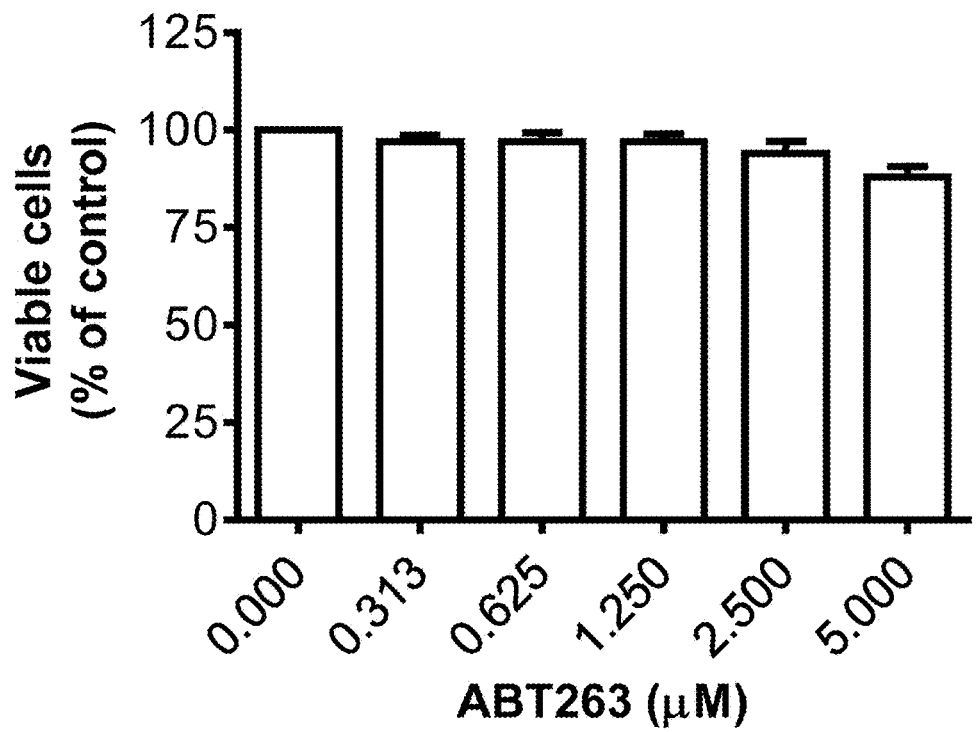
FIG. 1A, FIG. 1B, FIG. 1C, FIG. 1D, FIG. 1E, FIG. 1F, FIG. 1G, FIG. 1H and FIG. 1I depict graphs showing that ABT263 selectively kills senescent cells in a dose- and time-dependent, but cell type- and species-independent, manner in culture.
Figure 1B:
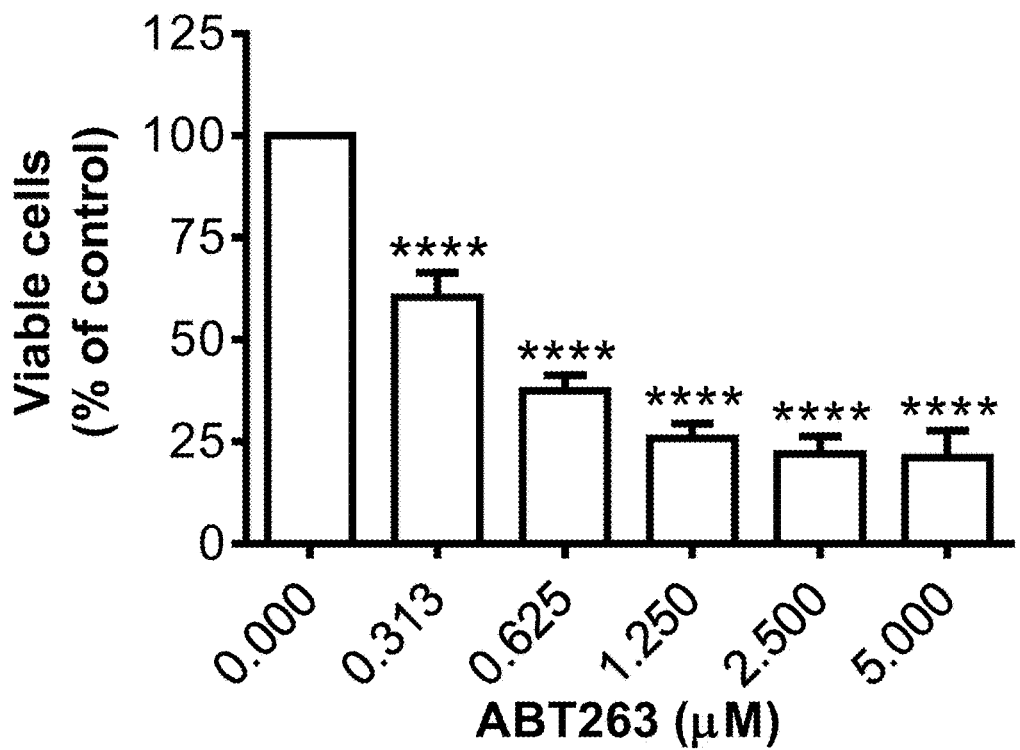
Figure 1C:
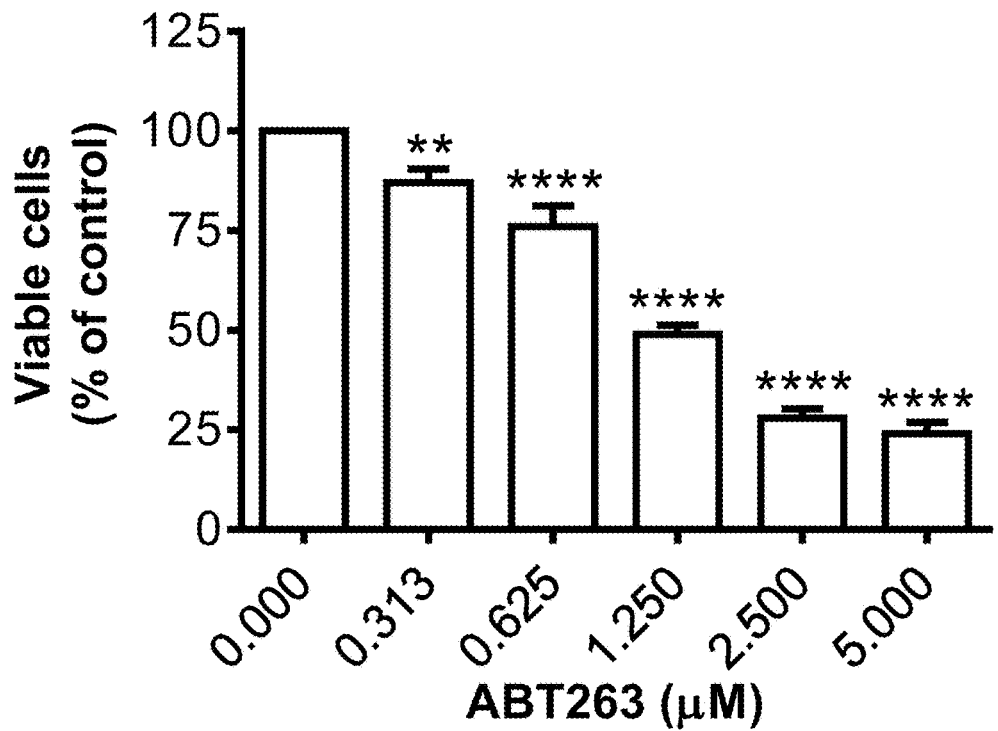
Figure 1D:
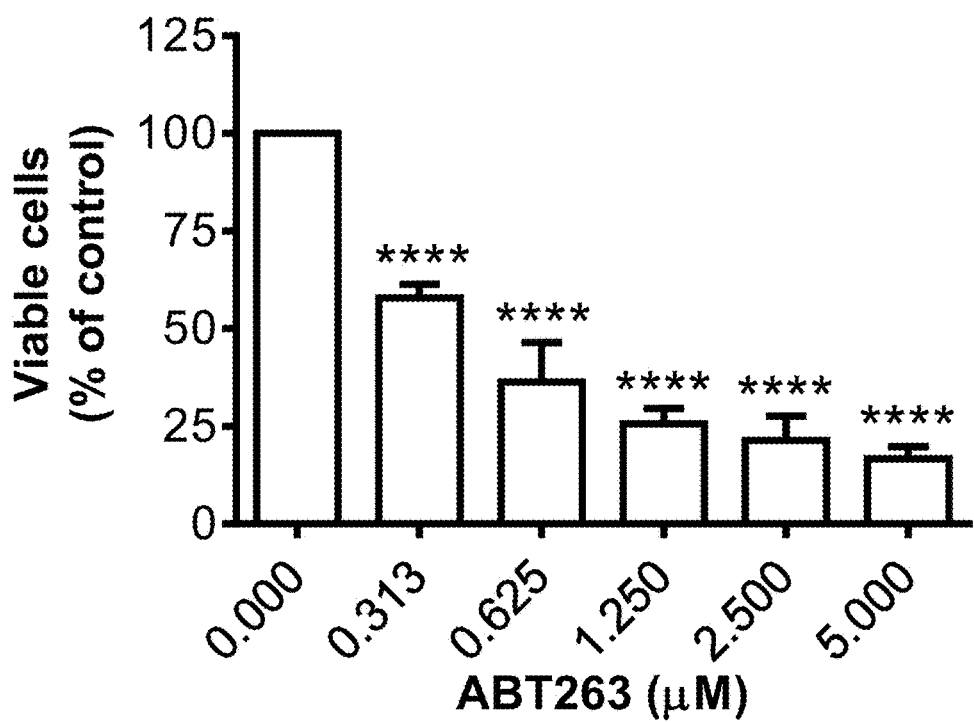

Aging is associated with an accumulation of senescent cells. Using human senescent fibroblasts, the inventors have discovered Bcl-2 family inhibitors that can selectively kill senescent cells while having minimal toxicity to normal cells. This finding suggests that inhibitors of anti-apoptotic proteins in the Bcl-2 family are novel anti-aging agents that have the potential to be used to delay aging-related disorders and extend a healthier lifespan by selectively eliminating senescent cells. As such, the invention encompasses a method of selectively killing senescent cells in a cell sample by administering a composition comprising at least one inhibitor of one or more anti-apoptotic proteins in the Bcl-2 family to the cells. Further, the invention encompasses a method to delay at least one feature of aging or treat an age-related disease or condition in a subject by administering a composition comprising at least one inhibitor of one or more anti-apoptotic proteins in the Bcl-2 family to a subject. Additionally, the invention encompasses a method of killing therapy-induced senescent cells in a subject that has received DNA-damaging therapy.

I. Compositions

In an aspect, a composition of the invention comprises at least one inhibitor of one or more anti-apoptotic proteins in the Bcl-2 family. In certain embodiments, a composition of the invention comprises at least one inhibitor of Bcl-2 and Bcl-xl. The composition may comprise a single inhibitor that inhibits both Bcl-2 and Bcl-xl. Alternatively, the composition may comprise two inhibitors, wherein one inhibitor inhibits Bcl-2 and a second inhibitor inhibits Bcl-xl. In each of the foregoing embodiment, the inhibitor may inhibit additional Bcl-2 family proteins in addition to Bcl-2 and/or Bcl-xl. Bcl-2 family proteins are described in more detail below.

A composition of the invention may optionally comprise one or more additional drug or therapeutically active agent in addition to the at least one inhibitor of one or more anti-apoptotic proteins in the Bcl-2 family. A composition of the invention may further comprise a pharmaceutically acceptable excipient, carrier or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants.

Other aspects of the invention are described in further detail below.

(a) Bcl-2 Inhibitor

As used herein, a "Bcl-2 inhibitor" includes at least one inhibitor of one or more anti-apoptotic proteins in the Bcl-2 family. Specifically, a Bcl-2 inhibitor of the invention selectively kills senescent cells. Methods to determine if a compound inhibits one or more anti-apoptotic proteins in the Bcl-2 family are known in the art. For example, nucleic acid expression, protein expression, or activity of Bcl-2 family proteins may be measured as described in detail below. Methods to determine if a compound selectively kills senescent cells are known in the art. For example, see Section II(b) and Section II(c).

Members of the B-cell lymphoma 2 (Bcl-2) family control the integrity of the outer mitochondrial membrane (OMM) and thus are critical in determining the susceptibility of cells to apoptosis induced by the intrinsic pathway. Bcl-2 family members can be divided into three subfamilies based on structural and functional features: an anti-apoptotic family, a multidomain pro-apoptotic family, and a BH3-only pro-apoptotic family. The anti-apoptotic subfamily suppresses apoptosis and promotes cell survival but not cell proliferation. As such, the anti-apoptotic proteins in the Bcl-2 family may also be referred to as pro-survival proteins. Non-limiting examples of anti-apoptotic Bcl-2 family proteins may include Bcl-2, Bcl-xl, Bcl-w, Mcl-1, Bfl1/A-1, and Bcl-B. The anti-apoptotic Bcl-2 family proteins are characterized by the presence of up to four relatively short sequence motifs, which are less than 20 amino acids in length, known as Bcl-2 homology 1 (BH1), BH2, BH3 and BH4 domains. They also have a C-terminal membrane-anchoring sequence and a similar three-dimensional structure. Inhibitors of one or more anti-apoptotic proteins in the Bcl-2 family may promote cell death by antagonizing the pro-survival function of the Bcl-2 protein family thereby inducing apoptosis. An inhibitor of the invention may inhibit one or more anti-apoptotic proteins in the Bcl-2 family. Accordingly, an inhibitor of the invention may inhibit one or more anti-apoptotic proteins selected from the group consisting of Bcl-2, Bcl-xl, Bcl-w, Mcl-1, Bfl1/A-1, and Bcl-B. In certain embodiments, an inhibitor of the invention is a Bcl-2, Bcl-xl and Bcl-w inhibitor. In a specific embodiment, an inhibitor of the invention is a Bcl-2 and Bcl-xl inhibitor. It is understood that an inhibitor of the invention may primarily inhibit Bcl-2 and/or Bcl-xl, but also have inhibitory effects on other members of the anti-apoptotic proteins in the Bcl-2 family.

An inhibitor of one or more anti-apoptotic proteins in the Bcl-2 family may be an inhibitor that inhibits nucleic acid expression, protein expression, or protein function of a Bcl-2 family protein. An inhibitor may selectively inhibit one, two, three, four, five, six or more members of the Bcl-2 family proteins. In an embodiment, an inhibitor may affect nucleic acid or protein expression of a Bcl-2 family protein. Non-limiting examples of inhibitors that decrease nucleic acid and protein expression may include histone deacetylase inhibitors such as sodium butyrate and depsipeptide, synthetic cytotoxic retinoid such as fenretinide, and cyclin-dependent kinase inhibitors such as flavopiridol. Alternatively, an inhibitor may be an antisense molecule. For example, oblimersen sodium (G3139) is a Bcl-2 antisense that targets BCL-2 mRNA. In another embodiment, an inhibitor may be a natural inhibitor of Bcl-2 family interactions. For example, progidiosin molecules (bypyrrole-containing natural products), such as GX15-070 (obatoclax) may inhibit Bcl-2 family proteins such as Bcl-2, Bcl-xl, Bcl-w and Mcl-1. Additionally, the natural inhibitor gossypol (AT-101) and its derivatives, apogossypolone, TW37 and TM-1206, may inhibit Bcl-2 family proteins such as Bcl-2, Bcl-xl, and Mcl-1. In still another embodiment, an inhibitor may be designed to bind the hydrophobic grove of anti-apoptotic Bcl-2 family proteins in place of BH3-only proteins (i.e., BH3-mimetics). As such, an inhibitor may be a small molecule inhibitor of one or more anti-apoptotic proteins in the Bcl-2 family. For example, isoxazolidine-based small molecules that interact with Bcl-2 and Bcl-xl, ABT-737 and ABT-263 (navitoclax) that bind Bcl-2, Bcl-xl, and Bcl-w. Non-limiting examples of other Bcl-2 family inhibitors may include $SAHB_A$, terphenyl, benzoylureas, A-385358, A-874009, A-1155463, A-1331852, apogossypolone, BM-1074, BM-1197, BXI-72, HA-14, antimycin A, ABT199, WEHI539, MIM-1, and $BH_3Is$. In a specific embodiment, an inhibitor is a molecule similar to ABT-263. In an exemplary embodiment, an inhibitor of one or more anti-apoptotic proteins in the Bcl-2 family is ABT-263.

In an embodiment, at least one inhibitor of one or more anti-apoptotic proteins in the Bcl-2 family is administered. For example, 1, 2, 3, 4, 5 or more inhibitors of one or more anti-apoptotic proteins in the Bcl-2 family may be administered. Each Bcl-2 inhibitor administered may target the same or different anti-apoptotic protein in the Bcl-2 family. In an embodiment, two inhibitors of one or more anti-apoptotic proteins in the Bcl-2 family may be administered. In another embodiment, one inhibitor of one or more anti-apoptotic proteins in the Bcl-2 family may be administered.

Dosages of the pharmaceutical compositions can vary between wide limits, depending upon the disease or disorder to be treated, the age and condition of the subject to be treated. In an embodiment where the inhibitor is contacted with a sample, the concentration of inhibitor may be from about 0.3125 µM to about 5 µM. Alternatively, the concentration of inhibitor may be from about 0.01 µM to about 10 µM. For example, the concentration of inhibitor may be about 0.01, about 0.05, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9 or about 10 µM. Additionally, the concentration of inhibitor may be greater than 10 µM. For example, the concentration of inhibitor may be about 10, about 15, about 20, about 25, about 30, about 35, about 40, about 45, about 50, about 55, about 60, about 65, about 70, about 75, about 80, about 85, about 90, about 95 or about 100 µM.

In an embodiment where the composition comprising at least one inhibitor of one or more anti-apoptotic proteins in the Bcl-2 family is administered to a subject, the dose of inhibitor may be from about 0.1 mg/kg to about 500 mg/kg. For example, the dose of inhibitor may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of inhibitor may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of inhibitor may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg. In a specific embodiment, the dose of the inhibitor may be about 50 mg/kg. The composition comprising at least one inhibitor of one or more anti-apoptotic proteins in the Bcl-2 family may be administered to a subject at various frequencies, intervals and durations by various routes (topical application, enteral, or parenteral administration).

i. Nucleic Acid Expression of One or More Anti-Apoptotic Proteins in the Bcl-2 Family In an embodiment, nucleic acid expression of the anti-apoptotic proteins in the Bcl-2 family may be measured to identify a compound that inhibits one or more anti-apoptotic proteins in the Bcl-2 family. For example, when Bcl-2 family protein nucleic acid expression is decreased in the presence of a compound relative to an untreated control, the compound downregulates a Bcl-2 family protein. In a specific embodiment, Bcl-2 family protein mRNA may be measured to identify a compound that modulates a Bcl-2 family protein.

Methods for assessing an amount of nucleic acid expression in cells are well known in the art, and all suitable methods for assessing an amount of nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of expression of a target nucleic acid comprises, in part, measuring the level of target nucleic acid mRNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to the sequence specific non-covalent binding interaction with a complementary nucleic acid. In a preferred embodiment, hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression may be determined using PCR. Methods of PCR are well and widely known in the art, and may include quantitative PCR, semi-quantitative PCR, multiplex PCR, or any combination thereof. Specifically, the amount of nucleic acid expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire mRNA transcript for a nucleic acid sequence, or measuring a portion of the mRNA transcript for a nucleic acid sequence. For instance, if a nucleic acid array is utilized to measure the amount of mRNA expression, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. Such a control nucleic acid should not specifically hybridize with an aiRNA nucleotide sequence of the invention. This allows comparisons between assays that are performed on different occasions.

ii. Protein Expression of One or More Anti-Apoptotic Proteins in the Bcl-2 Family In another embodiment, protein expression of one or more anti-apoptotic proteins in the Bcl-2 family may be measured to identify a compound that modulates one or more Bcl-2 family proteins. For example, when protein expression of one or more anti-apoptotic proteins in the Bcl-2 family is decreased in the presence of a compound relative to an untreated control, the compound downregulates protein expression of one or more anti-apoptotic proteins in the Bcl-2 family. In a specific embodiment, protein expression protein expression of one or more anti-apoptotic proteins in the Bcl-2 family may be measured using immunoblot.

Methods for assessing an amount of protein expression are well known in the art, and all suitable methods for assessing an amount of protein expression known to one of skill in the art are contemplated within the scope of the invention. Non-limiting examples of suitable methods to assess an amount of protein expression may include epitope binding agent-based methods and mass spectrometry based methods.

In some embodiments, the method to assess an amount of protein expression is mass spectrometry. By exploiting the intrinsic properties of mass and charge, mass spectrometry (MS) can resolve and confidently identify a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can use mass spectrometry to look for the level of protein encoded from a target nucleic acid of the invention.

In some embodiments, the method to assess an amount of protein expression is an epitope binding agent-based method. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to a target gene protein. Nucleic acids may include RNA, DNA, and naturally occurring or synthetically created derivative.

As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g. Antibodies: A Laboratory Manual, Cold Spring Harbor Laboratory, 1988; herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art (See, e.g. U.S. Pat. No. 7,939,313; herein incorporated by reference in its entirety).

In general, an epitope binding agent-based method of assessing an amount of protein expression comprises contacting a sample comprising a polypeptide with an epitope binding agent specific for the polypeptide under conditions effective to allow for formation of a complex between the epitope binding agent and the polypeptide. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen present. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, Ni2+, Flag tags, myc tags, heavy metals, and enzymes (including alkaline phosphatase, peroxidase, and luciferase). Methods of detecting an epitope binding agent-polypeptide complex based on the detection of a label or marker are well known in the art.

In some embodiments, an epitope binding agent-based method is an immunoassay. Immunoassays can be run in a number of different formats. Generally speaking, immunoassays can be divided into two categories: competitive immunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In some embodiments, the epitope binding agent-based method is an ELISA. In other embodiments, the epitope binding agent-based method is a radioimmunoassay. In still other embodiments, the epitope binding agent-based method is an immunoblot or Western blot. In alternative embodiments, the epitope binding agent-based method is an array. In another embodiment, the epitope binding agent-based method is flow cytometry. In different embodiments, the epitope binding agent-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

iii. Activity of One or More Anti-Apoptotic Proteins in the Bcl-2 Family

In an embodiment, activity of one or more anti-apoptotic proteins in the Bcl-2 family may be measured to identify a compound that modulates one or more anti-apoptotic proteins in the Bcl-2 family. For example, apoptosis may be measured as an indication of activity of one or more anti-apoptotic proteins in the Bcl-2 family. Apoptosis may be measured using methods standard in the art as described below in Section II(c). For example, when apoptosis of senescent cells is increased in the presence of a compound relative to an untreated control, the compound may downregulate one or more anti-apoptotic proteins in the Bcl-2 family.

In another embodiment, cell viability may be measured as an indication of activity of one or more anti-apoptotic proteins in the Bcl-2 family. Cell viability may be measured using methods standard in the art as described below in Section II(c). For example, when cell viability of senescent cells is decreased in the presence of a compound relative to an untreated control, the compound may downregulate one or more anti-apoptotic proteins in the Bcl-2 family.

In still another embodiment, caspase3 may be measured as an indication of activity of one or more anti-apoptotic proteins in the Bcl-2 family. In the presence of an inhibitor of one or more anti-apoptotic proteins in the Bcl-2 family, caspase3 may be activated. This may be measured as an increase in caspase3 or a decrease in procaspae3. Caspases may be measured using, for example, methods to detect protein expression as described above.

(b) Components of the Composition

The present disclosure also provides pharmaceutical compositions. The pharmaceutical composition comprises at least one inhibitor of one or more anti-apoptotic proteins in the Bcl-2 family, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as ethylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising at least one inhibitor of one or more Bcl-2 family proteins is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of at least one inhibitor of one or more Bcl-2 family proteins in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, at least one inhibitor of one or more Bcl-2 family proteins may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecadienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spinosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetonitrile, alcohols, dimethylformamide, tetrahydrofuran, or combinations thereof.

Liposomes carrying at least one inhibitor of one or more Bcl-2 family proteins (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. At least one inhibitor of one or more Bcl-2 family proteins may be encapsulated in a microemulsion by any method generally known in the art.

In yet another embodiment, at least one inhibitor of one or more Bcl-2 family proteins may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

The present disclosure encompasses a method of selectively killing one or more senescent cells in a sample, the method comprising contacting a composition comprising an effective amount of at least one inhibitor of one or more anti-apoptotic proteins in the Bcl-2 family with the sample. In another aspect, the present disclosure encompasses a method of selectively killing one or more senescent cells in a subject in need thereof, the method comprising administering to the subject a composition comprising a therapeutically effective amount of at least one inhibitor of one or more anti-apoptotic proteins in the Bcl-2 family.

By selectively killing one or more senescent cells is meant a composition of the invention does not appreciably kill non-senescent cells at the same concentration. Accordingly, the median lethal dose or LD50 of the inhibitor in non-senescent cells may be about 5 to about 50 times higher than the LD50 of the inhibitor in senescent cells. As used herein, the LD50 is the concentration of inhibitor required to kill half the cells in the cell sample. For example, the LD50 of the inhibitor in non-senescent cells may be greater than about 5, about 6, about 7, about 8, about 9 or about 10 times higher than the LD50 of the inhibitor in senescent cells. Alternatively, the LD50 of the inhibitor in non-senescent cells may be greater than about 10, about 15, about 20, about 25, about 30, about 35, about 40, about 45, or about 50 times higher than the LD50 of the inhibitor in senescent cells. Additionally, the LD50 of the inhibitor in non-senescent cells may be greater than 50 times higher than the LD50 of the inhibitor in senescent cells. In a specific embodiment, the LD50 of the inhibitor in non-senescent cells is greater than 10 times higher than the LD50 of the inhibitor in senescent cells. In another specific embodiment, the LD50 of the inhibitor in non-senescent cells is greater than 20 times higher than the LD50 of the inhibitor in senescent cells.

The progression from an actively dividing cell to a metabolically active, non-dividing cell is termed "senescence" or "cellular senescence." As used herein, the terms "senescence" and "cellular senescence" may be used interchangeably. The term "senescence" also refers to the state into which cells enter after multiple rounds of division and, as a result of cellular pathways, future cell division is prevented from occurring even though the cell remains metabolically active. Senescent cells may differ from their pre-senescent counterparts in one or more of the following ways: 1) they arrest growth and cannot be stimulated to reenter the cell cycle by physiological mitogens; 2) they become resistant to apoptotic cell death; and/or 3) they acquire altered differentiated functions.

In contrast to cancer cells which grow and divide uncontrollably, the ability of most differentiated eukaryotic cells to proliferate is finite. Stated another way, normal cells have an intrinsically determined limit to the number of cell divisions through which they can proceed. This phenomenon has been termed "replicative cellular senescence" and is an intrinsic anticancer mechanism that limits a cell's proliferative ability, thereby preventing neoplastic transformation. Another form of senescence is "premature cellular senescence." Premature cellular senescence, like replicative cellular senescence, is a terminal fate of mitotic cells, characterized by permanent cell cycle arrest. Unlike replicative cellular senescence, however, premature cellular senescence does not require telomere deterioration and can be induced by a variety of stressors including, but not limited to, ultraviolet light, reactive oxygen species, chemotherapeutics, environmental toxin, cigarette smoking, ionizing radiation, distortion of chromatin structure, excessive mitogenic signaling, and oncogenic mutations. Still another form of senescence is therapy-induced senescence (TIS) which refers to the phenomenon of a subset of tumor cells being forced into a senescent state by therapeutic agents. TIS is known to develop because of certain treatments, including radiotherapy and chemotherapy.

The number of senescent cells in various organs and tissues of a subject increases with age. The accumulation of senescent cells may drive the deterioration that underlies aging and age-related diseases. For example, the accumulation of senescent cells in aged tissue may contribute to age-associated tissue dysfunction, reduced regenerative capacity, and disease. In this context, senescence is considered deleterious because it contributes to decrements in tissue renewal and function. As a non-limiting example, an aged tissue may lack the ability to respond to stress when proliferation is required thereby resulting in the reduced fitness seen with aging. A key component of this model is that substantial numbers of senescent cells should be present in tissues with aging, without, or prior to, pathology.

(a) Senescent Cells

A senescent cell may be a cell that ceases to divide but remains metabolically active. The non-dividing cells may remain viable for many weeks, but fail to grow/replicate DNA despite the presence of ample space, nutrients and growth factors in the medium. Thus, the senescence growth arrest is essentially permanent because senescent cells cannot be stimulated to proliferate by known physiological stimuli. Further, a senescent cell of the invention may be resistant to certain apoptotic signals and may acquire widespread changes in gene expression. The resistance to apoptosis may explain the increase in senescent cells with age. Manipulation of pro- and anti-apoptotic proteins may cause cells that are destined to die by apoptosis to senesce and, conversely, cause cells that are destined to senesce to undergo apoptosis.

A senescent cell of the invention may be senescent due to replicative cellular senescence, premature cellular senescence or therapy-induced senescence. Senescent cells that are senescent due to replication may have undergone greater than 60 population doublings. Alternatively, senescent cells that are senescent due to replication may have undergone greater than 40, greater than 50, greater than 60, greater than 70 or greater than 80 population doublings. A senescent cell that is prematurely cellular senescent may be induced by, but limited to, ultraviolet light, reactive oxygen species, chemotherapeutics, environmental toxin, cigarette smoking, ionizing radiation, distortion of chromatin structure, excessive mitogenic signaling, and oncogenic mutations. In a specific embodiment, premature cellular senescence may be induced by ionizing radiation (IR). In another specific embodiment, premature cellular senescence may also be induced by ectopic transfection with Ras oncogene. A senescent cell that is therapy-induced senescent may have been exposed to DNA-damaging therapy.

A senescent cell of the invention may generally be a eukaryotic cell. Non-limiting examples of senescent cells may include, but are not limited to, mammary epithelial cells, keratinocytes, cardiac myocytes, chondrocytes, endothelial cells (large vessels), endothelial cells (microvascular), epithelial cells, fibroblasts, follicle dermal papilla cells, hepatocytes, melanocytes, osteoblasts, preadipocytes, primary cells of the immune system, skeletal muscle cells, smooth muscle cells, adipocytes, neurons, glial cells, contractile cells, exocrine secretory epithelial cells, extracellular matrix cells, hormone secreting cells, keratinizing epithelial cells, islet cells, lens cells, mesenchymal stem cells, pancreatic acinar cells, paneth cells of the small intestine, primary cells of hemopoietic linage, primary cells of the nervous system, sense organ and peripheral neuron supporting cells, wet stratified barrier epithelial cells and stem cells. In a specific embodiment, the stem cells are adult stem cells. Adult stem cells are stem cells which maintain and repair the tissue in which they are found and are generally referred to by their tissue of origin. Non-limiting examples of adult stem cells include muscle stem cells, hematopoietic stem cells, heart stem cells, neural stem cells, mesenchymal stem cells, intestinal stem cells, skin stem cells, adipose-derived stem cells, endothelial stem cells, and dental pulp stem cells. In a specific embodiment, a senescent cell of the invention is a fibroblast. In another specific embodiment, a senescent cell may be a hematopoietic stem cell.

Further, a senescent cell of the invention may be found in renewable tissues, including the vasculature, hematopoietic system, epithelial organs and the stroma. A senescent cell of the invention may also be found at sites of aging or chronic age-related pathology, such as osteoarthritis and atherosclerosis. Further, a senescent cell of the invention may be associated with benign dysplastic or preneoplastic lesions and benign prostatic hyperplasia. In an embodiment, a senescent cell of the invention may be found in normal and tumor tissues following DNA-damaging therapy. In a specific embodiment, a senescent cell may be found at a site of aging or age-related pathology.

An age-related pathology may include any disease or condition which is fully or partially mediated by the induction or maintenance of a non-proliferating or senescent state in a cell or a population of cells in a subject. Non-limiting examples include age-related tissue or organ decline which may lack visible indication of pathology, or overt pathology such as a degenerative disease or a function-decreasing disorder. For example, Alzheimer's disease, Parkinson's disease, cataracts, macular degeneration, glaucoma, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, and cancer treatment-related disability such as atrophy and fibrosis in various tissues, brain and heart injury, and therapy-related myelodysplastic syndromes. Additionally, an age-related pathology may include an accelerated aging disease such as progeroid syndromes (i.e. Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, restrictive dermopathy), ataxia telangiectasia, Fanconi anemia, Friedreich's ataxia, dyskeratosis congenital, aplastic anemia, IPF, and others. A method of identifying an age-related disease or condition as described herein may include detecting the presence of senescent cells.

(b) Detecting Senescent Cells

In an aspect, a method of the invention may comprise detecting senescent cells. Senescent cells may be detected in vivo or in vitro. Suitable markers for detecting senescent cells in vitro and in vivo are known in the art. For example, methods to detect senescent cells may include, but are not limited to, detecting lack of DNA replication by incorporation of 5-bromodeoxyuridine (BrdU) or $^3$H-thymidine, immunostaining for proteins such as proliferating cell nuclear antigen (PCNA) and Ki-67, histochemical staining for senescence-associated β-galactosidase (SA-β-gal), detecting expression of p16, p19, Pai1, Igfbp2, IL-6, Mmp13, Nrg1, differentiated embryo-chondrocyte expressed-1 (DEC1), p15 (a CDK1) and decoy death receptor-2 (DCR2), detecting cytological markers such as senescence-associated heterochromatin foci (SAHFs) and senescence-associated DNA-damage foci (SDFs). SAHFs may be detected by the preferential binding of DNA dyes, such as 4',6-diamidino-2-phenylindole (DAPI), and the presence of certain heterochromatin-associated histone modifications (for example, H3 Lys9 methylation) and proteins (for example, heterochromatin protein-1 (HP1)). Additionally, senescent cells may be detected as described in U.S. Pat. No. 5,491,069 and US Patent Application No. 2010/0086941. In certain embodiments, senescent cells are detected by histochemical staining for SA-β-gal.

In certain embodiments, one or more senescent cells are detected in a sample. A sample may be a cell sample, a tissue sample, or a biopsy from a subject. Generally speaking, a sample may be dependent on the age-related pathology. For instance, a sample may be tissue biopsy material. As such, a tissue sample may be from esophagus, stomach, liver, gallbladder, pancreas, adrenal glands, bladder, gallbladder, large intestine, small intestine, kidneys, liver, pancreas, colon, stomach, thymus, spleen, brain, spinal cord, nerves, adipose tissue, heart, lungs, eyes, corneal, skin or islet tissue or organs. In a specific embodiment, a tissue sample may be from lung, skeletal muscle, and brain. In another specific embodiment, a tissue sample may be from liver and heart. Alternatively, a sample may be a cell sample. As such, a cell sample may be oocytes and/or spermatozoa, mesenchymal stem cells, adipocytes, central nervous system neurons and glial cells, contractile cells, exocrine secretory epithelial cells, extracellular matrix cells, hormone secreting cells, keratinizing epithelial cells, islet cells, kidney cells, lens cells, pancreatic acinar cells, paneth cells of small intestine, primary cells of hemopoietic lineage, primary cells of the nervous system, sense organ and peripheral neuron supporting cells or wet stratified barrier epithelial cells. Detection of senescent cells may be used to assess the replicative history of tissues, thereby providing a method for evaluation of the physiological, in contrast to the chronological age of the tissue.

The number of senescent cells may increase with age. The number of senescent cells in a tissue or sample may be from less than 1% to greater than 15%. In an embodiment, the number of senescent cells in a tissue or sample may be less than 1%, less than 2%, less than 3%, less than 4%, or less than 5%. In another embodiment, the number of senescent cells in a tissue or sample may be about 5%, about 6%, about 7%, about 8%, about 9%, or about 10%. In still another embodiment, the number of senescent cells in a tissue or sample may be greater than 10%, greater than 11%, greater than 12%, greater than 13%, greater than 14%, or greater than 15%.

(c) Measuring Cell Death

In an aspect, a method of the invention may comprise cell death of senescent cells. Methods of measuring cell death are known in the art. For example, cell death may be measured by Giemsa staining, trypan blue exclusion, acridine orange/ethidium bromide (AO/EB) double staining for fluorescence microscopy and flow cytometry, propidium iodide (PI) staining, annexin V assay, TUNEL assay, DNA ladder, LDH activity, and MTT assay. In a preferred embodiment, cell death is due to induction of apoptosis. Cell death due to induction of apoptosis may be measured by observation of morphological characteristics including cell shrinkage, cytoplasmic condensation, chromatin segregation and condensation, membrane blebbing, and the formation of membrane-bound apoptotic bodies. Cell death due to induction of apoptosis may be measured by observation of biochemical hallmarks including internucleosomal DNA cleavage into oligonucleosome-length fragments. Traditional cell-based methods of measuring cell death due to induction of apoptosis include light and electron microscopy, vital dyes, and nuclear stains. Biochemical methods include DNA laddering, lactate dehydrogenase enzyme release, and MTT/XTT enzyme activity. Additionally, terminal deoxynucleotidyl transferase-mediated dUTP-biotin nick end labeling of DNA fragments (TUNEL) and in situ end labeling (ISEL) techniques are used, which when used in conjunction with standard flow cytometric staining methods yield informative data relating cell death to various cellular parameters, including cell cycle and cell phenotype. See Loo and Rillema, Methods Cell Biol. 1998; 57:251-64, which is incorporated herein by reference, for a review of these methods. In an exemplary embodiment, cell death due to apoptosis may be measured by the reduction of procaspase-3. Caspase-3 has been implicated as an "effector" caspase associated with the initiation of the "death cascade" and is therefore an important marker of the cell's entry point into the apoptotic signaling pathway. Caspase-3 is activated by the upstream caspase-8 and caspase-9, and since it serves as a convergence point for different signaling pathways, it is well suited as a read-out in an apoptosis assay.

The results of these methods may be used to determine the percentage of viable cells. In a preferred embodiment, cell death may be measured as a reduction in viable cells. Since a composition of the invention selectively kills senescent cells, a reduction in viable cells is indicative of a reduction in senescent cells. As described in Section II(b), the number of senescent cells in a sample may be from less than 1% to greater than 15%. As such, a reduction in viable cells following administration of an inhibitor of the invention may be greater than 15% to less than 1%. For example, the reduction in viable cells may be less than 1%, less than 2%, less than 3%, less than 4%, or less than 5%. Alternatively, the reduction in viable cells may be about 5%, about 6%, about 7%, about 8%, about 9%, or about 10%. Additionally, the reduction in viable cells may be greater than 10%, greater than 11%, greater than 12%, greater than 13%, greater than 14%, or greater than 15%.

(d) Administration

In certain aspects, a therapeutically effective amount of a composition of the invention may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. For example, if the disease or condition is COPD or IPF, the composition may be administered via inhalation. Alternatively, is the disease or condition is osteoarthritis, the composition may be administered via intra-articular invention. It is within the skill of one in the art, to determine the route of administration based on the disease or condition to be treated. In a specific embodiment, a composition of the invention is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response (e.g., cell death of senescent cells, an anti-aging response, an improvement in symptoms associated with a degenerative disease, or an improvement in symptoms associated with a function-decreasing disorder). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the age-related disease or condition, the degenerative disease, the function-decreasing disorder, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

(e) Subject

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the subject is a human.

The human subject may be of any age. However, since senescent cells are normally associated with aging, a human subject may be an older human subject. In some embodiments, the human subject may be about 30, 40, 45, 50, 55, 60, 65, 70, 75, 80, 85, 90, 95 years of age or older. In some preferred embodiments, the human subject is 30 years of age or older. In other preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

Additionally, a subject in need thereof may be a subject suffering from an age-related disease or condition as described below.

(f) Aging and Age-Related Diseases

It has been demonstrated that senescent cells drive age-related pathologies and that selective elimination of these cells can prevent or delay age-related deterioration. Thus, senescent cells may be therapeutic targets in the treatment of aging and age-related disease. As such, removal of senescent cells may delay tissue dysfunction and extend health span. Clearance of senescent cells is expected to improve tissue milieu, thereby improving the function of the remaining non-senescent cells.

The present disclosure provides a method for delaying at least one feature of aging in a subject, the method comprising administering a composition comprising a therapeutically effective amount of at least one inhibitor of one or more anti-apoptotic proteins in the Bcl-2 family to a subject. As used herein, "a feature of aging" may include, but is not limited to, systemic decline of the immune system, muscle atrophy and decreased muscle strength, decreased skin elasticity, delayed wound healing, retinal atrophy, reduced lens transparency, reduced hearing, osteoporosis, sarcopenia, hair graying, skin wrinkling, poor vision, frailty, and cognitive impairment.

In an aspect, a composition of the invention selectively kills senescent cells. In this way, targeting senescent cells during the course of aging may be a preventative strategy. Accordingly, administration of a composition comprising a therapeutically effective amount of at least one inhibitor of one or more anti-apoptotic proteins in the Bcl-2 family to a subject may prevent comorbidity and delay mortality in an older subject. Further, selective killing of senescent cells may boost the immune system, extend the health span, and improve the quality of life in a subject. Additionally, selective killing of senescent cells may delay sarcopenia. Sarcopenia is the degenerative loss of skeletal muscle mass, quality, and strength associated with aging. As such, a delay in sarcopenia may reduce frailty, reduce risk of falling, reduce fractures, and reduce functional disability in a subject. Furthermore, selective killing of senescent cells may delay aging of the skin. Aged skin has increased wrinkles, decreased immune barrier function and increased susceptibility to skin cancer and trauma. As such, selective killing of senescent cells may delay skin wrinkling, delay the onset of decreased immune barrier function and decrease susceptibility to skin cancer and trauma in a subject. Selective killing of senescent cells may also delay the onset of retinal atrophy and reduced lens transparency as measured by vision tests.

Methods of measuring aging are known in the art. For example, aging may be measured in the bone by incident non-vertebral fractures, incident hip fractures, incident total fractures, incident vertebral fractures, incident repeat fractures, functional recovery after fracture, bone mineral density decrease at the lumbar spine and hip, rate of knee buckling, NSAID use, number of joints with pain, and osteoarthritis. Aging may also be measured in the muscle by functional decline, rate of falls, reaction time and grip strength, muscle mass decrease at upper and lower extremities, and dual tasking 10-meter gait speed. Further, aging may be measured in the cardiovascular system by systolic and diastolic blood pressure change, incident hypertension, major cardiovascular events such as myocardial infarction, stroke, congestive heart disease, and cardiovascular mortality. Additionally, aging may be measured in the brain by cognitive decline, incident depression, and incident dementia. Also, aging may be measured in the immune system by rate of infection, rate of upper respiratory infections, rate of flu-like illness, incident severe infections that lead to hospital admission, incident cancer, rate of implant infections, and rate of gastrointestinal infections. Other indications of aging may include, but not limited to, decline in oral health, tooth loss, rate of GI symptoms, change in fasting glucose and/or insulin levels, body composition, decline in kidney function, quality of life, incident disability regarding activities of daily living, and incident nursing home admission. Methods of measuring skin aging are known in the art and may include trans-epidermal water loss (TEWL), skin hydration, skin elasticity, area ratio analysis of crow's feet, sensitivity, radiance, roughness, spots, laxity, skin tone homogeneity, softness, and relief (variations in depth).

The present disclosure also provides a method of treating an age-related disease or condition, the method comprising administering a composition comprising a therapeutically effective amount of at least one inhibitor of one or more anti-apoptotic proteins in the Bcl-2 family to a subject in need thereof. As used herein, "age-related disease or condition" may include, but is not limited to, a degenerative disease or a function-decreasing disorder such as Alzheimer's disease, Parkinson's disease, cataracts, macular degeneration, glaucoma, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, cancer treatment-related disability such as atrophy and fibrosis in various tissues, brain and heart injury, and therapy-related myelodysplastic syndromes, and diseases associated with accelerated aging and/or defects in DNA damage repair and telomere maintenance such as progeroid syndromes (i.e. Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, restrictive dermopathy), ataxia telangiectasia, Fanconi anemia, Friedreich's ataxia, dyskeratosis congenital, aplastic anemia, IPF, and others. Methods of diagnosing and identifying an age-related disease or condition are known in the art.

The present disclosure also provides a method of killing therapy-induced senescent cells. The method comprises administering a composition comprising a therapeutically effective amount of at least one inhibitor of one or more anti-apoptotic proteins in the Bcl-2 family to a subject that has received DNA-damaging therapy and killing therapy induced-senescent cells in normal and tumor tissues following DNA-damaging therapy.

Non-limiting examples of DNA-damaging therapy may include γ-irradiation, alkylating agents such as nitrogen mustards (chlorambucil, cyclophosphamide, ifosfamide, melphalan), nitrosoureas (streptozocin, carmustine, lomustine), alkyl sulfonates (busulfan), triazines (dacarbazine, temozolomide) and ethylenimines (thiotepa, altretamine), platinum drugs such as cisplatin, carboplatin, oxalaplatin, antimetabolites such as 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, thioguanine, anthracyclines such as daunorubicin, doxorubicin, epirubicin, idarubicin, anti-tumor antibiotics such as actinomycin-D, bleomycin, mitomycin-C, mitoxantrone, topoisomerase inhibitors such as topoisomerase I inhibitors (topotecan, irinotecan) and topoisomerase II inhibitors (etoposide, teniposide, mitoxantrone), mitotic inhibitors such as taxanes (paclitaxel, docetaxel), epothilones (ixabepilone), vinca alkaloids (vinblastine, vincristine, vinorelbine) and estramustine.

Based on the observation that ionizing radiation and various chemotherapeutic agents elicit a marked senescence response in vivo, therapy-induced senescent cells may be a cause of long-term ramifications after DNA-damaging therapy, such as cancer therapy. As such, the systemic accumulation of therapy-induced senescent cells may drive accelerated physical decline in cancer survivors. Accelerated physical decline may also be referred to as accelerated aging. Accordingly, once a tumor is removed by systemic radiation or chemotherapy, senescence may be triggered in a variety of other organs, leading to long-term ramifications for the patient. Long-term ramifications may include reduced quality of life predisposing the subject to disabilities and comorbidities. For example, a subject that has received DNA-damaging therapy may experience a disproportionate decline in physical function, such as inability to walk up stairs or to reach up to put things onto shelves and/or increased functional disabilities such as difficulty, eating, dressing and maintaining adequate hygiene. Additionally, late effects of ionizing radiation may include long-term bone marrow injury and/or lung fibrosis. Long-term bone marrow injury can promote hypoplastic anemia and/or myelodysplastic syndrome or leukemia. Further, the inventors demonstrated that following ionizing radiation, senescent cells in lung, muscle and brain are greatly increased. These long-term ramifications provide a link between accelerated aging and cancer treatment. A method to measure accelerated aging may be as described in methods of measuring aging as above. Accordingly, administration of a composition comprising an inhibitor of the invention to a subject may prevent accelerated aging in a subject who has received DNA damaging therapy.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 5A:
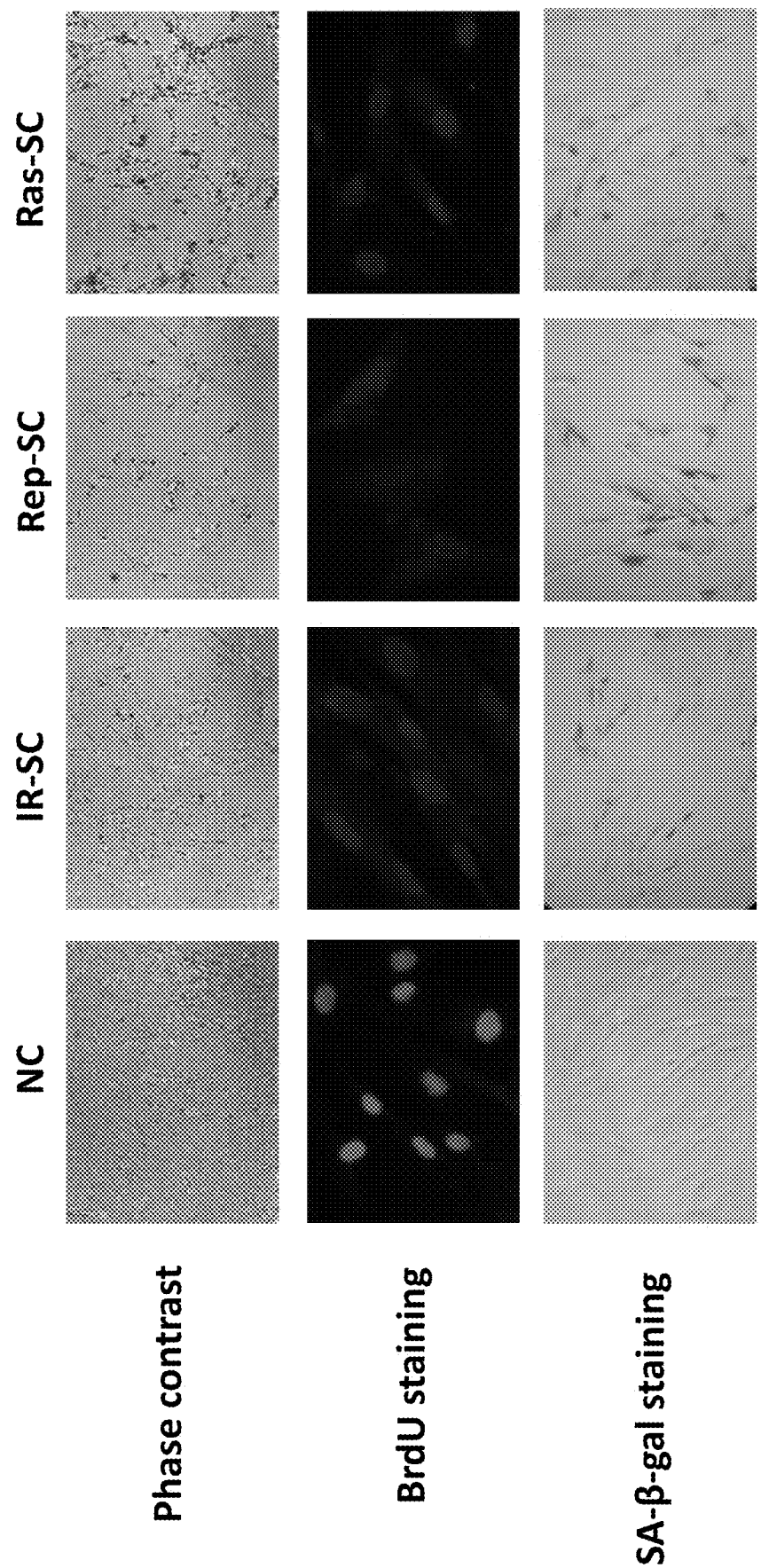
FIG. 5A and FIG. 5B depict images and a graph showing the analysis of WI38 cell senescence.
Figure 5B:
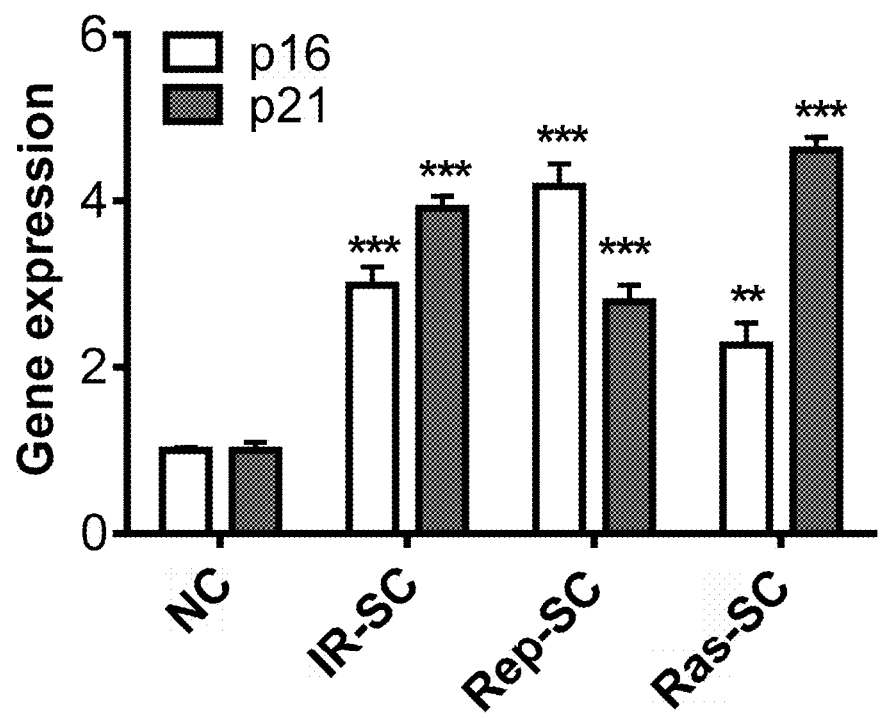
Figure 6A:
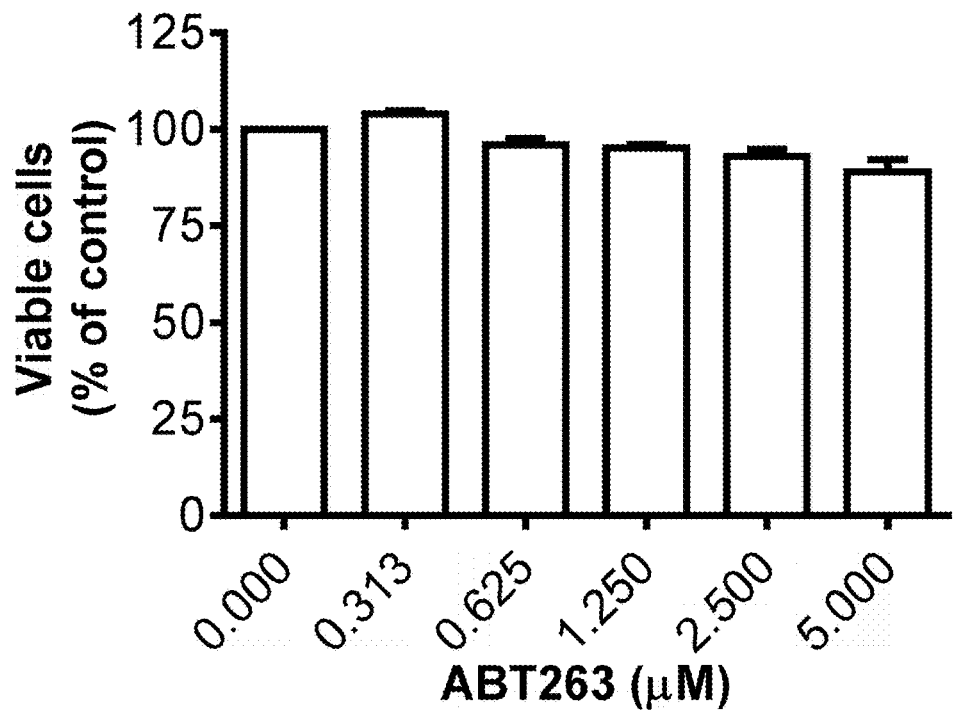
FIG. 6A, FIG. 6B, FIG. 6C and FIG. 6D depict graphs showing ABT263 selectively kills senescent cells in a dose-dependent manner in culture.
Figure 6B:
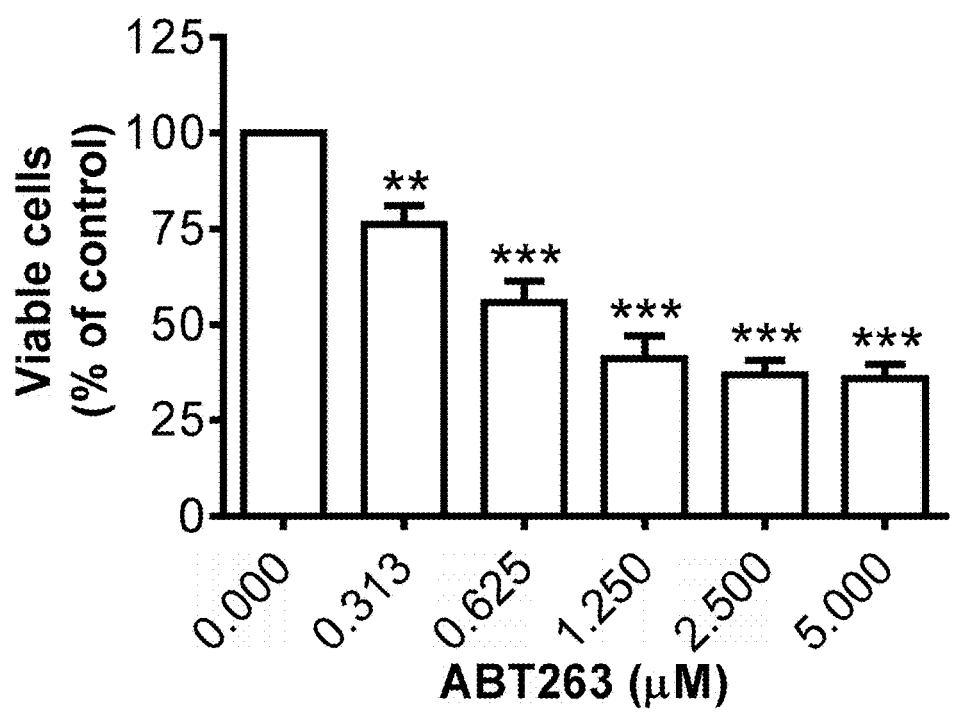
Figure 6C:
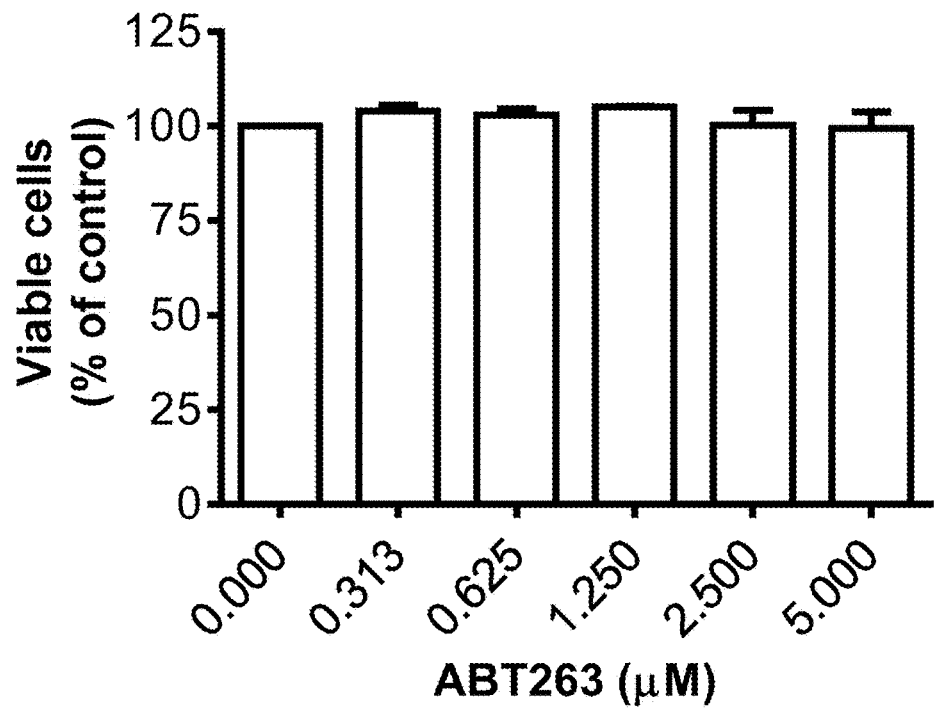
Figure 6D:
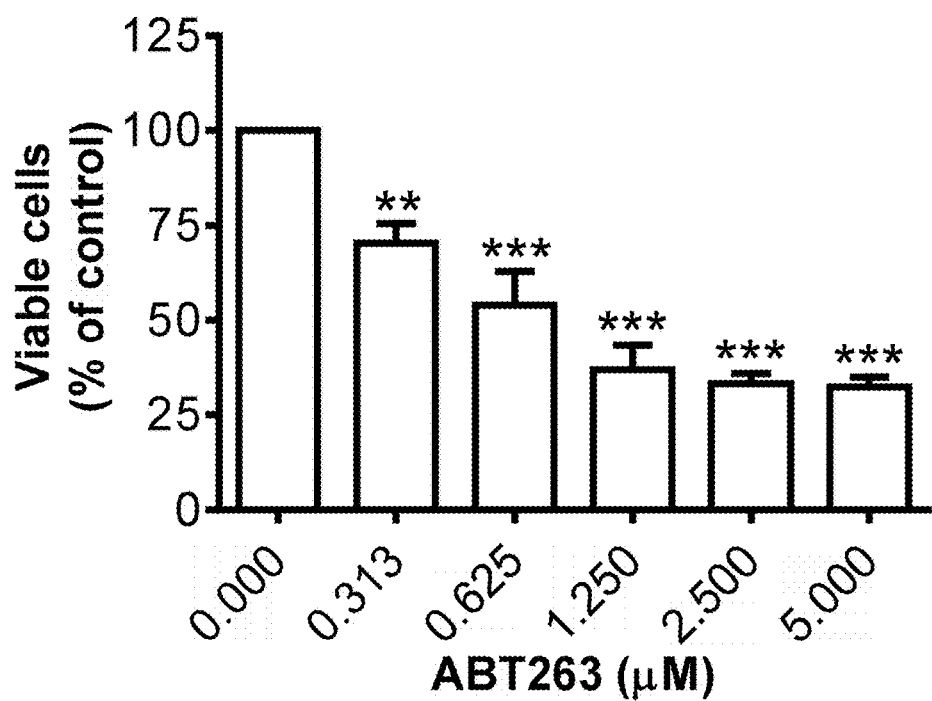

ABT263 Selectively Kills Senescent Cells in a Dose- and Time-Dependent, but Cell Type- and Species-Independent, Manner in Culture Normal human cells can undergo senescence after extensive cell division or exposure to genotoxic or oncogenic stresses such as ionizing radiation (IR) or expression of mutant Ras[8-10]. Cells induced to senesce by any of these means share several characteristics (FIG. 5). Cellular senescence is an important tumor-suppressive mechanism because it permanently arrests the proliferation of damaged and genetically deranged cells and promotes their removal by the immune system[8-10]. However, if SC production exceeds the immune clearance capacity or the immune system cannot efficiently remove SCs, SCs can accumulate in tissues; indeed, this occurs in mice and humans during aging and after exposure to IR[2,6]. SCs can disrupt tissue structures and functions and accelerate stem and progenitor cell exhaustion directly and indirectly by secreting inflammatory cytokines and many other factors, termed the senescence-associated secretory phenotype (SASP)[2, 5, 6]. Selective elimination of p16$^{Ink4a}$ (p16)-positive SCs in BubR1 hypomorphic progeroid mice through an INK-ATTAC transgene, which is activated by the drug AP20187, delayed the onset of several age-related pathologies[7]. Furthermore, late-life depletion of SCs in these mice attenuated the progression of age-related disorders[7]. These findings suggest that SCs play a causative role in certain age-related diseases. Thus, pharmacological clearance of SCs with a drug that does not depend on a transgene is an important goal for extending healthspan in humans. Such senolytic drugs might also be novel radiation mitigators because SCs are implicated in the pathogenesis of certain late effects of IR, such as long-term BM (LT-BM) injury and lung fibrosis[11, 12].

Figure 1E:
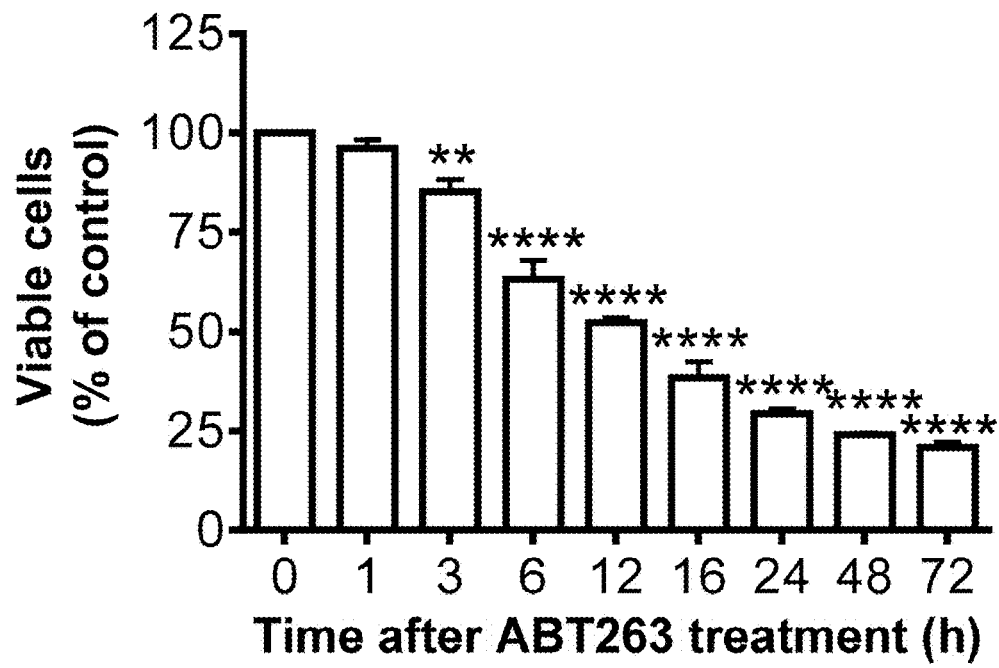
Figure 1F:
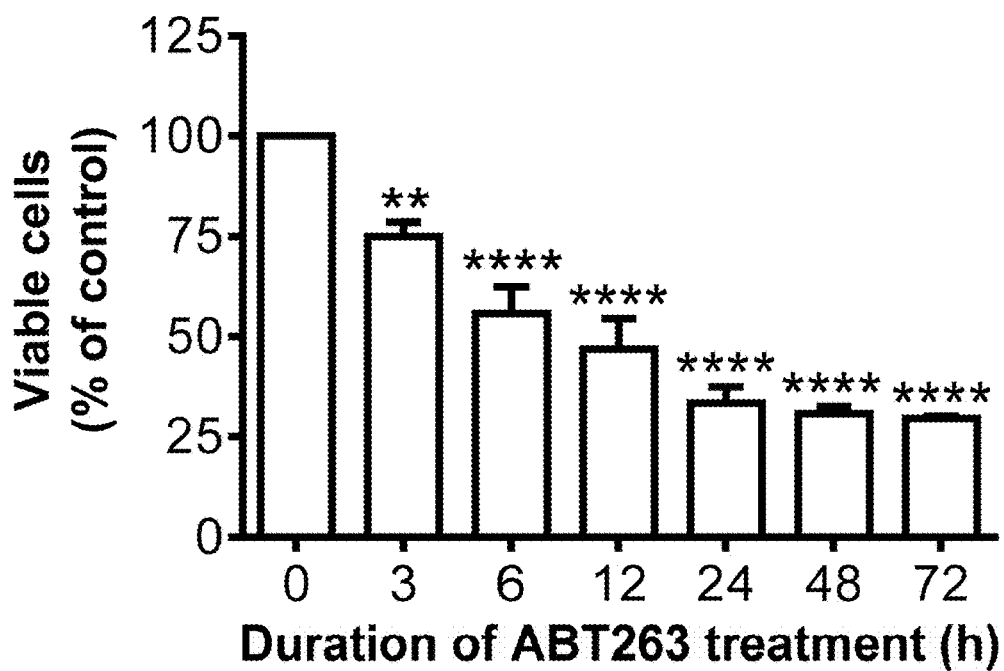
Figure 1G:
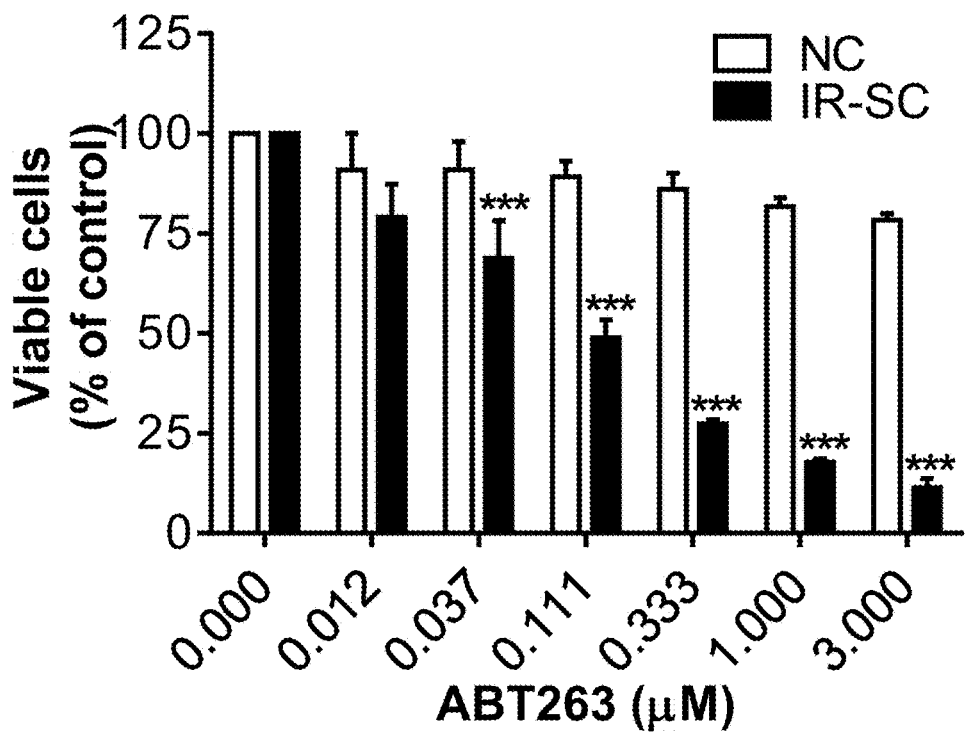
Figure 1H:
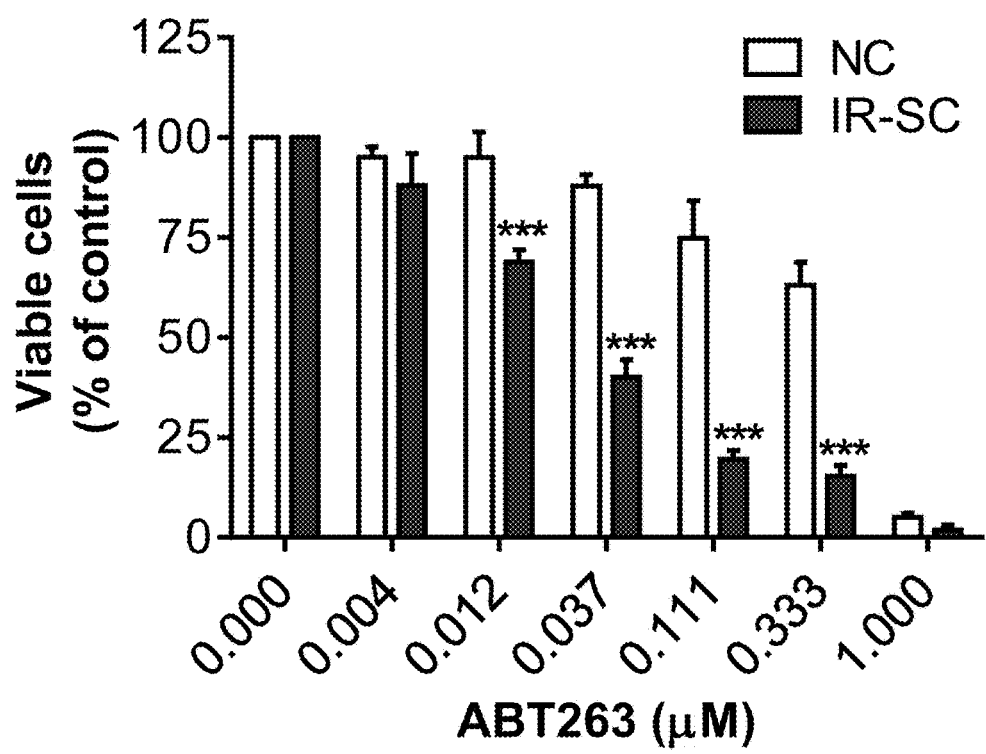
Figure 1I:
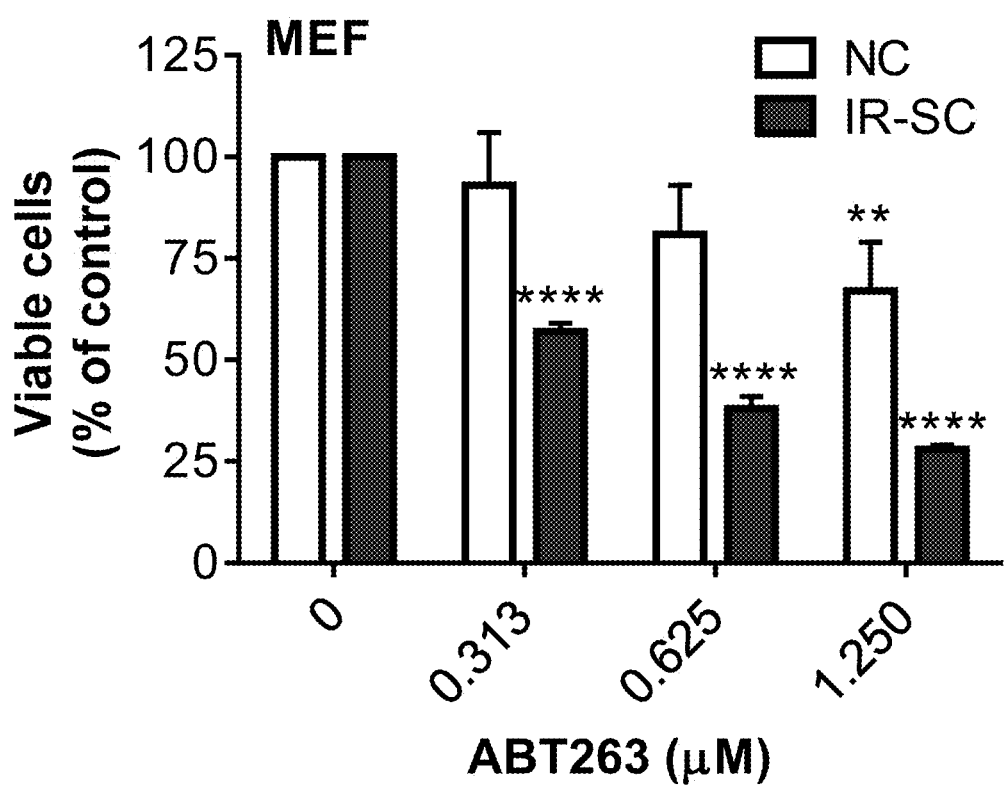

Despite large-scale efforts to identify small molecules that selectively kill SCs, senolytic drugs have not yet been discovered, even by our own groups, after screening thousands of compounds. We therefore took a targeted approach of individually titrating the cytotoxicity of a handful of small molecules targeting pathways that are predicted to be important for senescence maintenance. We assessed the survival of normal human WI-38 fibroblasts that were either non-senescent (N) or induced to senesce (S) by IR after incubation with the molecules (Table 1). With this approach, we identified ABT263 as a potent senolytic drug. WI-38 cells were resistant to ABT263 ($LD_{50}$=12.6 µM), whereas IR-induced SCs were highly sensitive ($LD_{50}$=0.61 µM) (FIG. 1A-D; FIG. 6). We observed similar results when senescence was induced by replicative exhaustion or oncogenic Ras expression (FIG. 1A-D and Table 2). Thus, ABT263 should have an excellent therapeutic window against SCs regardless of how they are induced. The cytotoxicity of ABT263 on SCs was rapid, requiring only ~24 h to kill the majority (70-80%) of SCs (FIG. 1E-F). In addition, ABT263 was cytotoxic against SCs in a cell type- and species-independent manner, because distinct senescent human and mouse cells were all more sensitive to ABT263 than their non-senescent counterparts (FIG. 1G-I).

TABLE 1

$LD_{50}$ value for various compounds against non-senescent WI-38 cells (NC) and IR-induced senescent WI-38 cells (SC)

| Compound name | Mechanisms of action | $LD_{50}$ (µM) for non-senescent cells (NC) | $LD_{50}$ (µM) for senescent cells (SC) | $LD_{50}$ Ratio (NC/SC) |
|---|---|---|---|---|
| ABT263 | bcl-2, bcl-xl, bcl-w inhibitor | 12.60 | 0.61 | 20.6 |
| ABT199 | bcl-2 inhibitor | >10.00 | >10.00 | 1.0 |
| WEHI539 | bcl-xl inhibitor | 2.80 | 3.88 | 0.7 |
| MIM1 | Mcl-1 inhibitor | >50.00 | >50.00 | 1.0 |
| 2-Deoxy-D-glucose | Glycolysis inhibitor | 4800.00 | 8890.00 | 0.5 |
| 3-bromopyruvate | glycolysis and TCA inhibitor | 280.00 | 370.00 | 0.8 |
| Auranofin | TrxR inhibitor | 5.13 | 5.34 | 1.0 |
| Buthionine sulfoximine | γ-GSC inhibitor | 2340.19 | 2391.51 | 1.0 |
| Decyl-triphenylphosphonium | ROS inducer | 1.41 | 0.98 | 1.4 |
| Arsenic trioxide | ROS inducer | 15.65 | 18.26 | 0.9 |
| Dehydroepiandrosterone | PPP inhibitor | 296.20 | 509.51 | 0.6 |
| Rapamycin | mTOR inhibitor | >0.04 | >0.04 | 1.0 |
| Metformin | AMPK activator | >20,000 | >20,000 | 1.0 |
| Psychosine | Lysosome toxin | 46.32 | 52.25 | 0.9 |
| Balifomycin A1 | (V)-ATPase inhibitor | 29.71 | 22.11 | 1.3 |
| Despramine | ASM inhibitor | 50.03 | 51.13 | 1.0 |
| Terfenadine | ASM inhibitor | 6.13 | 6.87 | 0.9 |
| Nutlin3 | Mdm2 inhibitor | 5.62 | 82.16 | 0.1 |
| KU55933 | ATM inhibitor | 5.10 | 30.73 | 0.2 |
| NU7026 | DNA-PK inhibitor | 47.02 | 64.03 | 0.7 |
| SB202190 | p38 MAPK inhibitor | >800.00 | >800.00 | 1.0 |
| Parthenolide | NF-κB inhibitor | 11.46 | 12.57 | 0.9 |
| BMS345541 | IKKβ inhibitor | 6.87 | 10.79 | 0.6 |
| JQ1 | BRDT/c-Myc inhibitor | 0.12 | 1.93 | 0.1 |
| MG132 | Proteasome inhibitor | 0.24 | 1.92 | 0.1 |
| IPI-504 | HSP 90 inhibitor | 0.14 | 0.93 | 0.2 |
| Echinomycin | HIF1α inhibitor | 0.42 | 2.86 | 0.2 |
| CPI-613 | PDH and α-ketoglutarate dehydrogenase inhibitor | 222.92 | 205.20 | 1.1 |
| Plumbagin | Anti-cancer agent ROS producer | 12.63 | 8.70 | 1.5 |
| Bortzomib | 26S proteasome inhibitor | 0.016 | 0.024 | 0.7 |
| Wogonin | Anti-cancer agent, ROS producer | >200.00 | >200.00 | 1.0 |

TABLE 1-continued

LD$_{50}$ value for various compounds against non-senescent WI-38
cells (NC) and IR-induced senescent WI-38 cells (SC)

| Compound name | Mechanisms of action | LD$_{50}$ (μM) for non-senescent cells (NC) | LD$_{50}$ (μM) for senescent cells (SC) | LD$_{50}$ Ratio (NC/SC) |
|---|---|---|---|---|
| Phenethyl isothiocyanate (PEITC) | ROS producer, Akt inactivator, JNK activator | <10.00 | >10.00 | <1.0 |
| Spermine | ROS producer | >40.00 | >40.00 | 1.0 |
| YM-155 | Survivin inhibitor | 78.43 | 50.02 | 1.6 |
| Hydrogen peroxide | ROS | 134.80 | 230.70 | 0.58 |
| Trichostatin A(TSA) | HDAC inhibitor | 0.72 | 0.39 | 1.87 |
| Vorinostat(SAHA) | HDAC inhibitor | 0.85 | 2.21 | 0.38 |

AMPK: AMP-activated protein kinase; ASM: Acid sphingomyelinase; ATM: Ataxia telangiectasia mutated; BRDT: Bromodomain testis-specific protein; DNA-PK: DNA-dependent protein kinase; γ-GSC: γ-glutamylcysteine synthetase; HDAC: Histone deacetylase; HIF1α: hypoxia inducible factor 1α; HSP 90: Heat-shock protein 90; IKKβ: IκB kinase β; JNK: Jun N-terminal kinase; MAPK: Mitogen-activated protein kinase; PDH: Pyruvate dehydrogenase; PPP: Pentose Phosphate Pathway; TCA: Citric acid cycle; TrxR: Thioredoxin reductase.

TABLE 2

LD$_{50}$ value of ABT263 against non-senescent
and senescent WI38 cells

| Cell types | LD$_{50}$ (μM) | LD$_{50}$ Ratio (NC/SC) |
|---|---|---|
| NC | 12.60 | — |
| IR-SC | 0.61 | 20.66 |
| Rep-SC | 1.45 | 8.69 |
| Ras-SC | 0.62 | 20.32 |

Example 2

ABT263 Kills Senescent Cells by Apoptosis

Figure 2A:
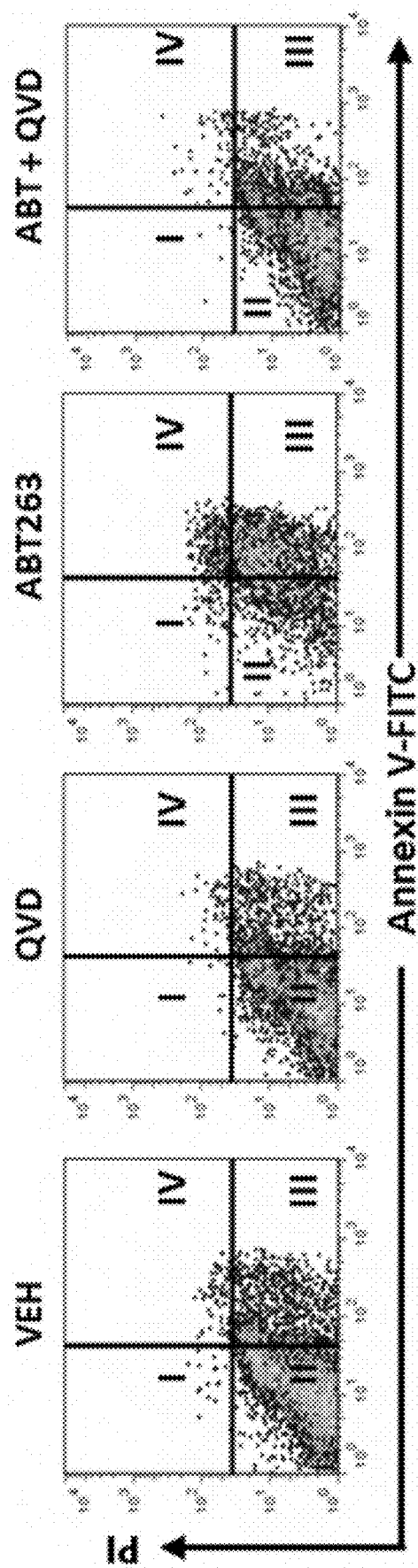
FIG. 2A, FIG. 2B, FIG. 2C, FIG. 2D, FIG. 2E, FIG. 2F, FIG. 2G, FIG. 2H, FIG. 2I, FIG. 2J, FIG. 2K, FIG. 2L, FIG. 2M and FIG. 2N depict graphs, flow cytometry plots and Western blots showing that ABT263 kills senescent cells by apoptosis.
Figure 2B:
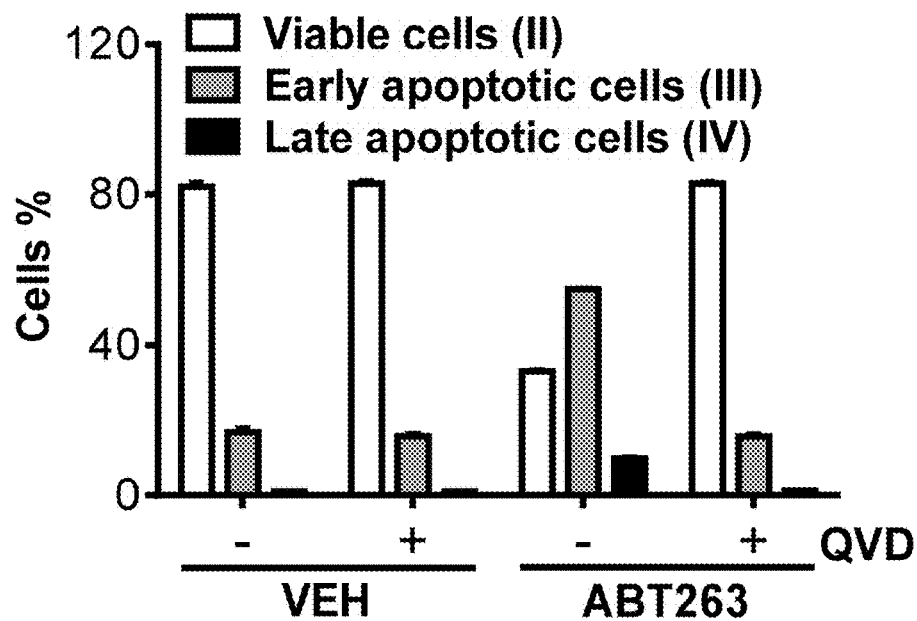
Figure 2C:
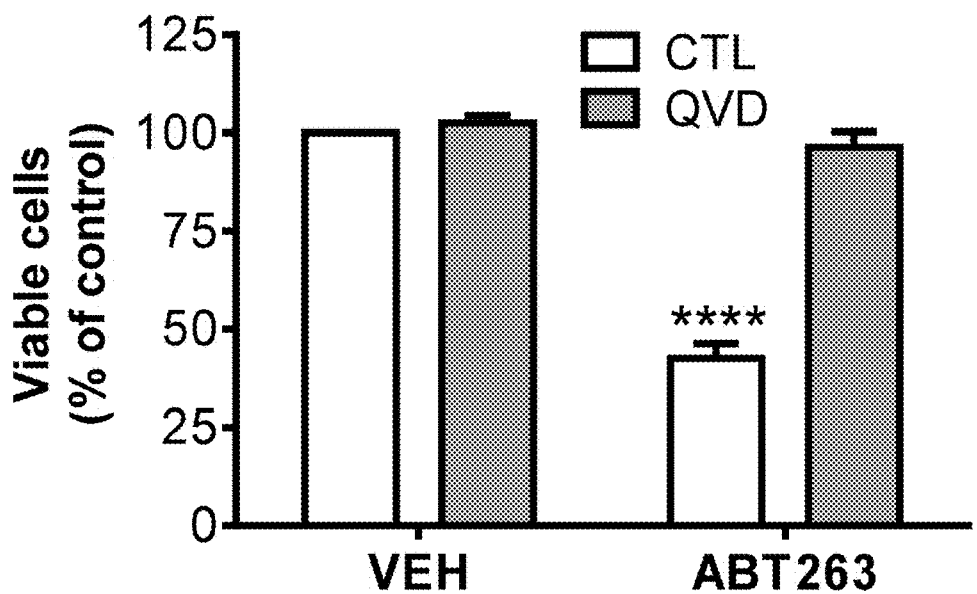
Figure 2D:
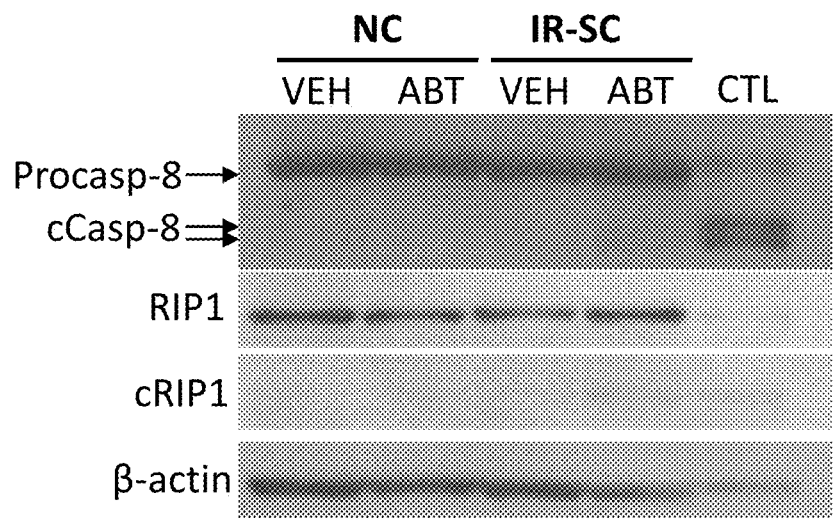
Figure 2E:
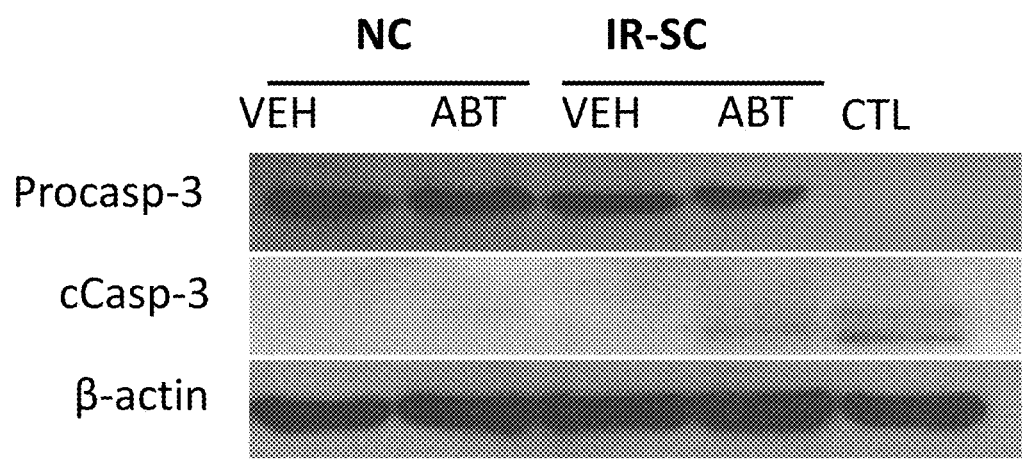
Figure 2F:
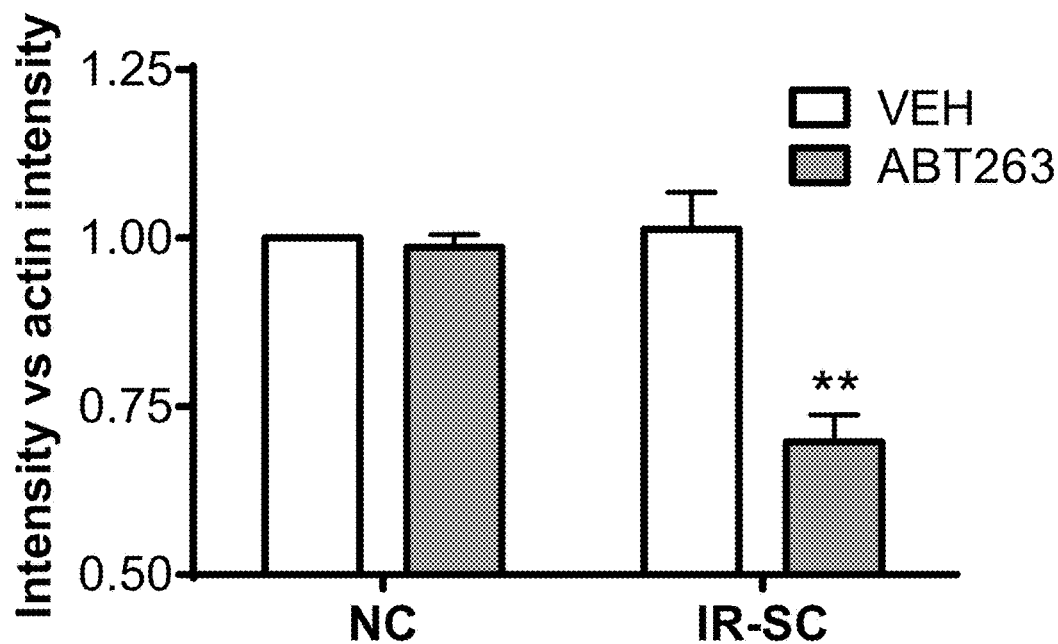

ABT263 is a potent inducer of apoptosis in many tumor cells[13]. To determine the mechanism of ABT263 action against SCs, we analyzed apoptosis in IR-induced WI-38 SCs after vehicle or ABT263 treatment with or without the pan-caspase inhibitor Q-VD-OPh (QVD)[14]. ABT263 selectively killed SCs by inducing apoptosis, which was abrogated by QVD (FIG. 2A-C). ABT263 likely killed SCs through the intrinsic apoptotic pathway[15, 16] because SCs activated caspase 3, but not caspase 8, after incubation with ABT263 (FIG. 2D-F).

Figure 2G:
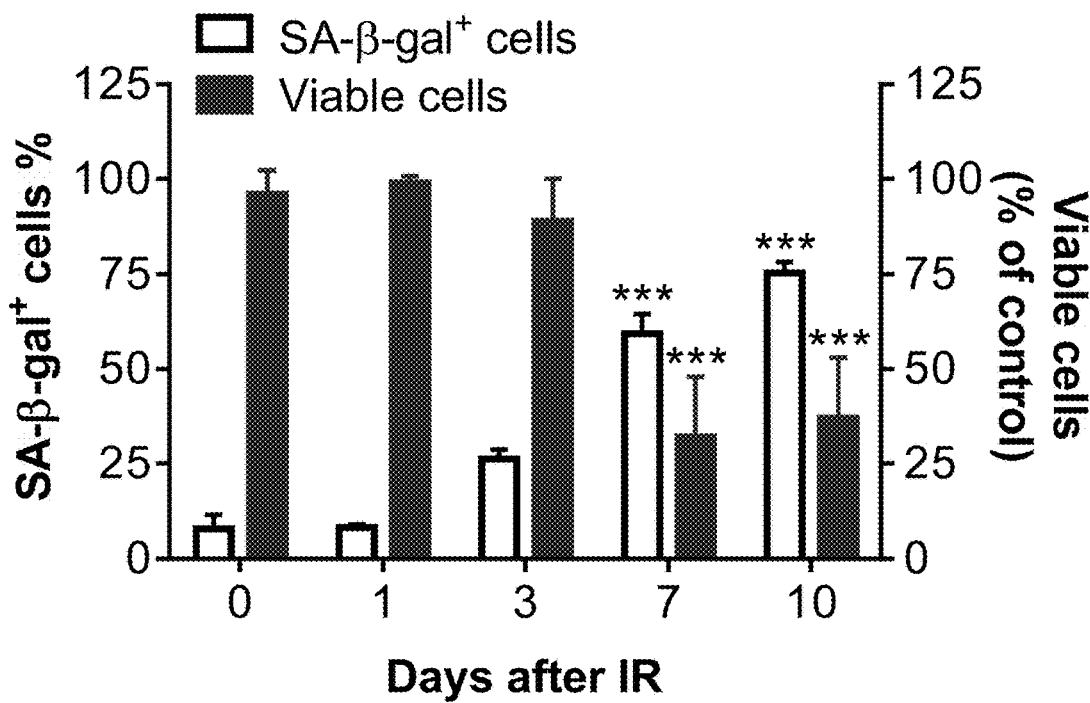
Figure 2H:
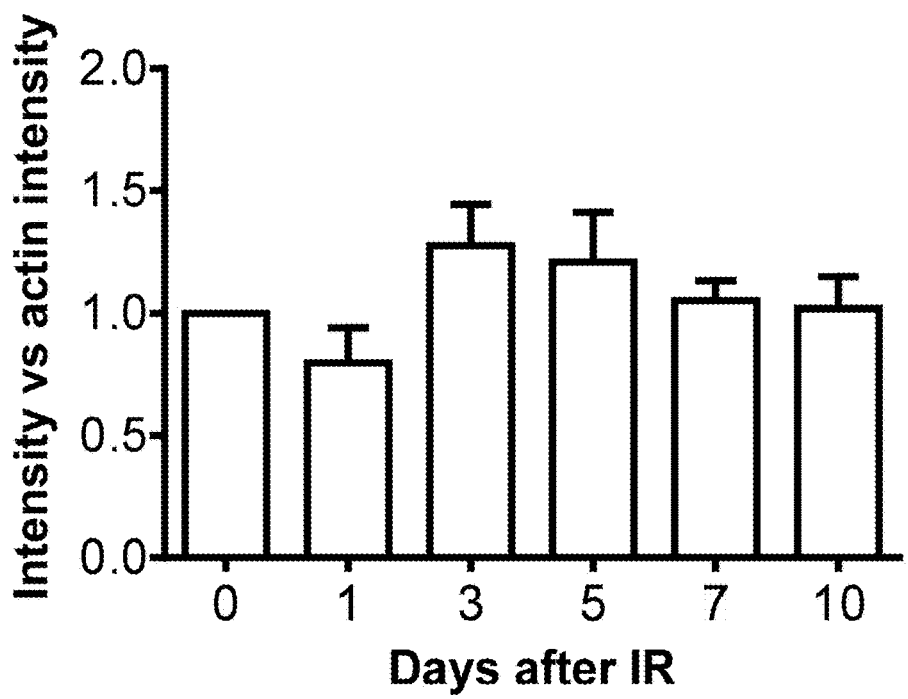
Figure 2I:
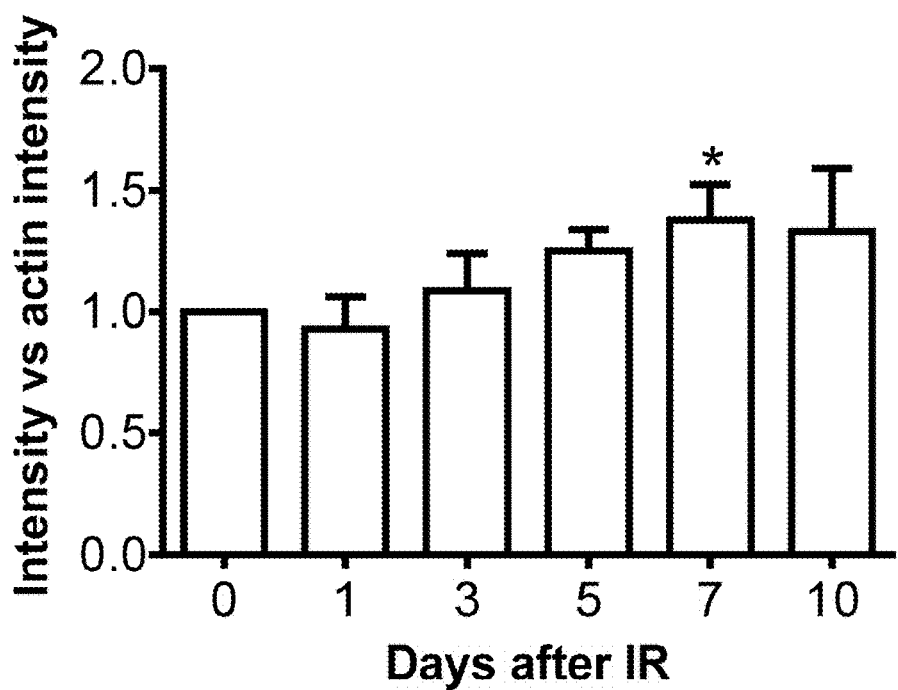
Figure 2J:
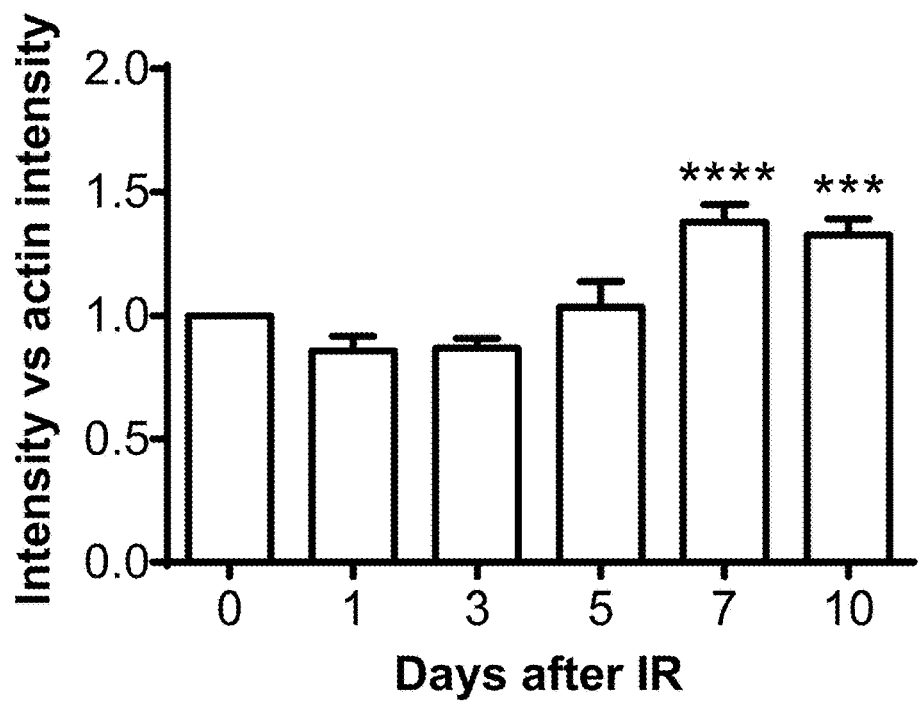
Figure 2K:
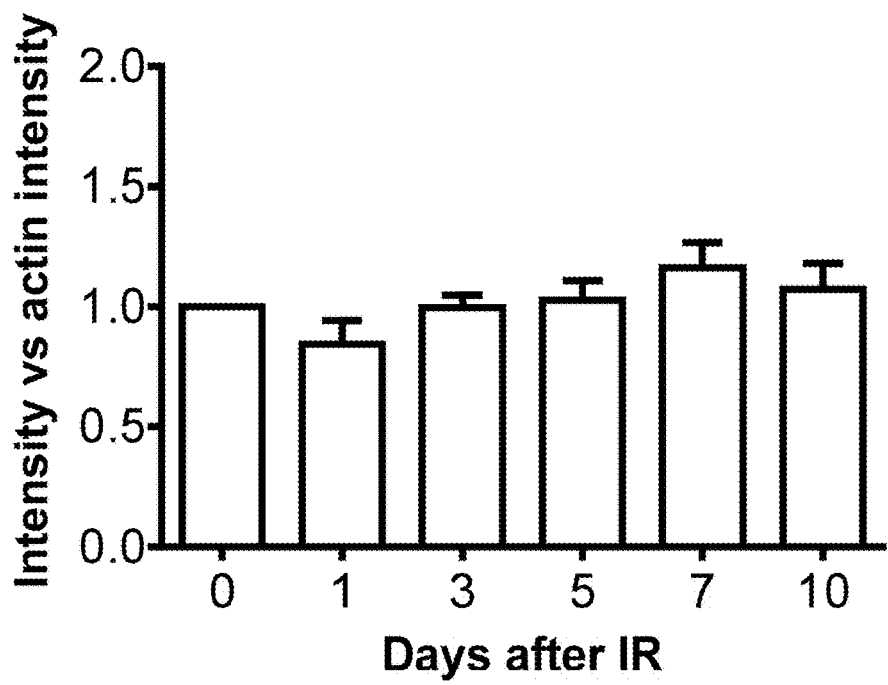
Figure 2L:
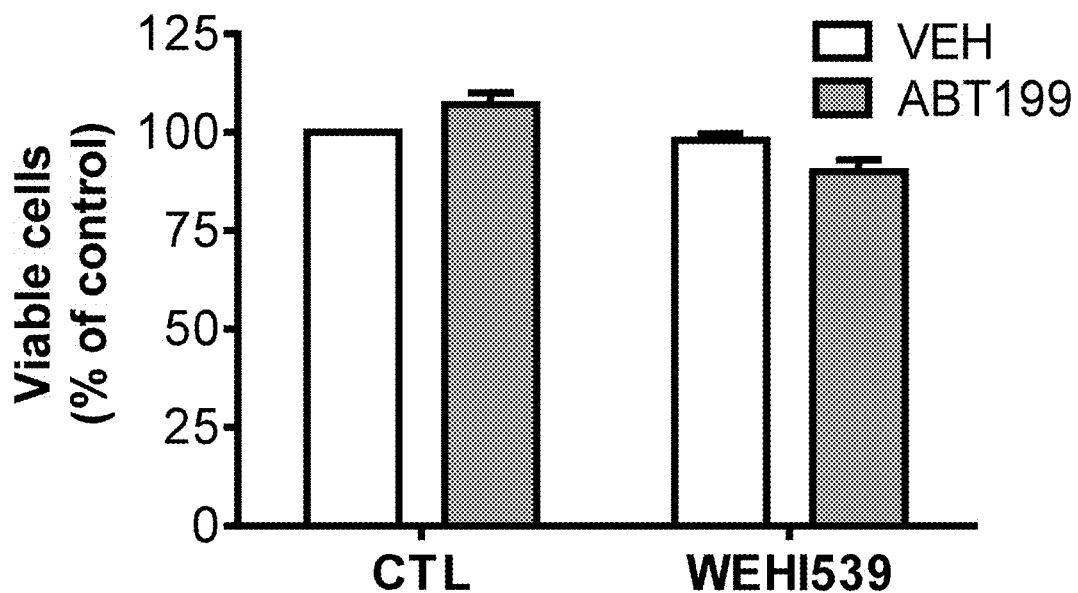
Figure 2M:
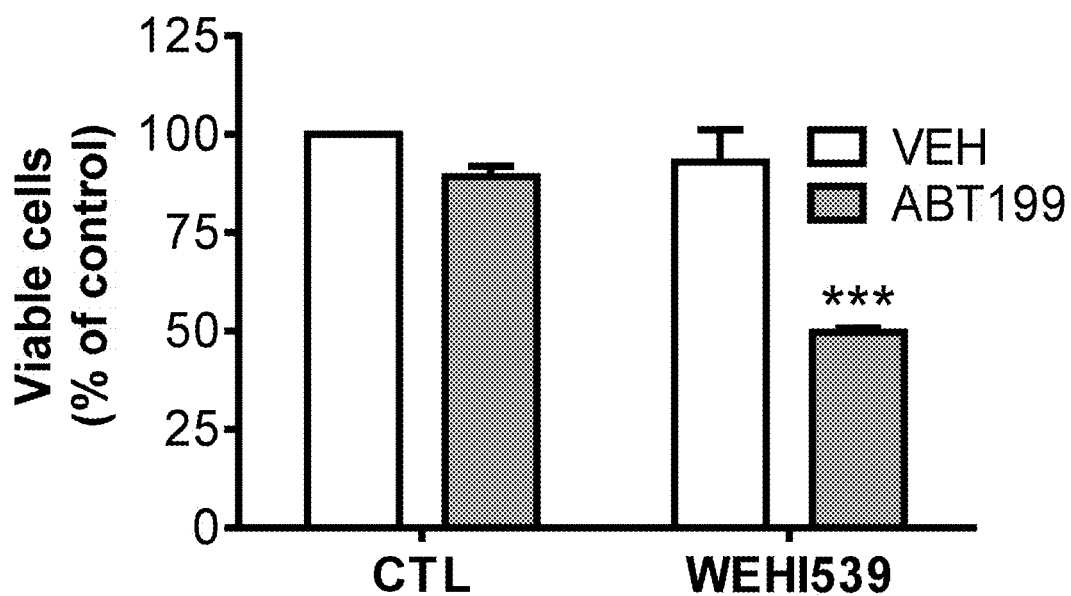
Figure 2N:
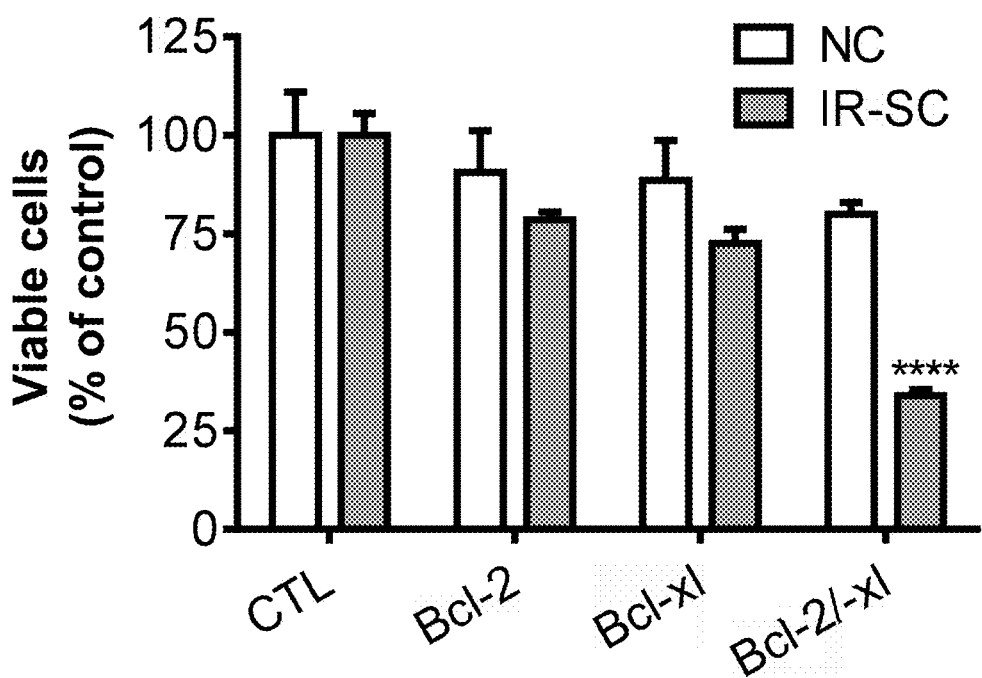
Figure 7A:
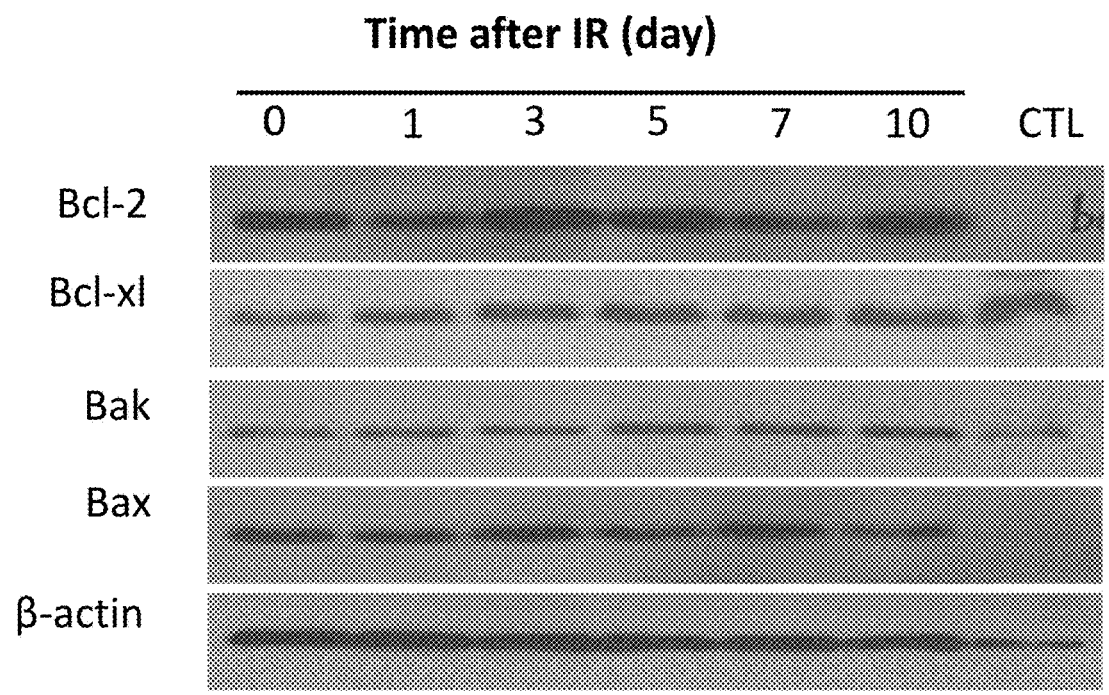
FIG. 7A and FIG. 7B depict Western blot analysis of anti- and pro-apoptotic proteins in WI-38 cells after IR. A representative Western blot image of Bcl-2, Bcl-xl, Bak, and Bax in WI-38 cells at various times after exposure to 10 Gy IR is shown in (FIG. 7A) and that of Bad, Bid, Noxa, and Bim in (FIG. 7B). β-actin is used as a loading control. CTL represents a positive control using cell lysates from Hela (FIG. 7A) and K562 (FIG. 7B) cells treated with 2 μM MG132 for 24 h.
Figure 7B:
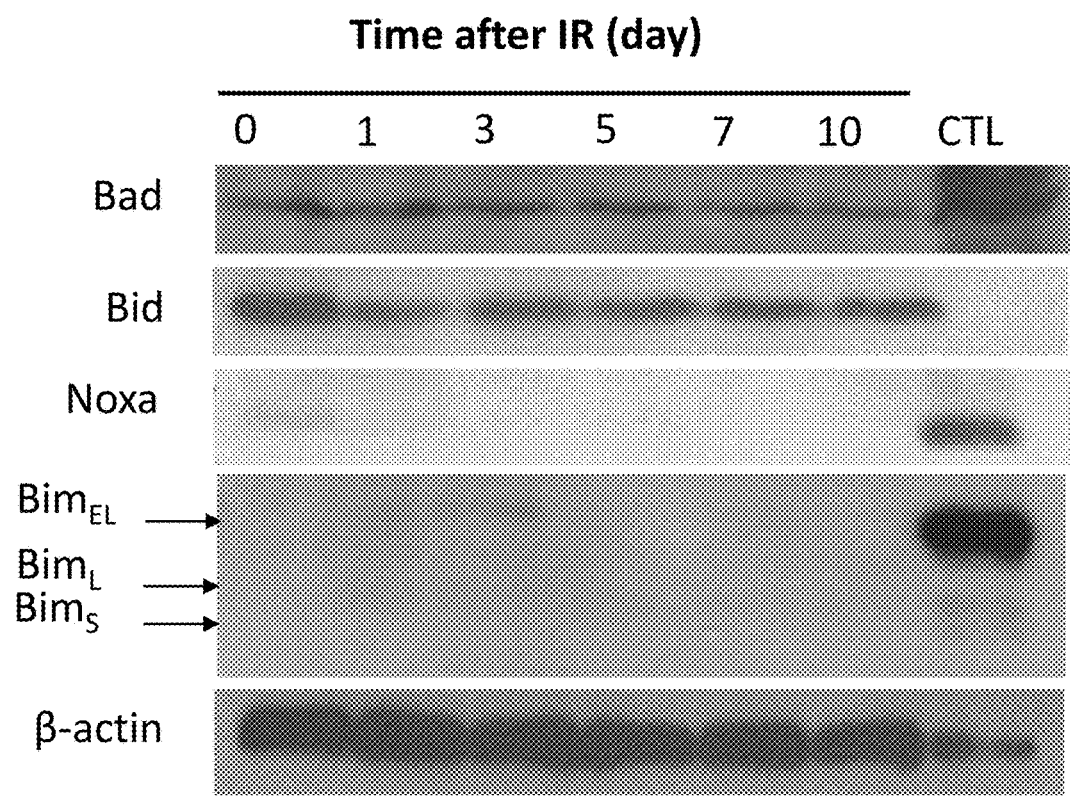
Figure 8A:
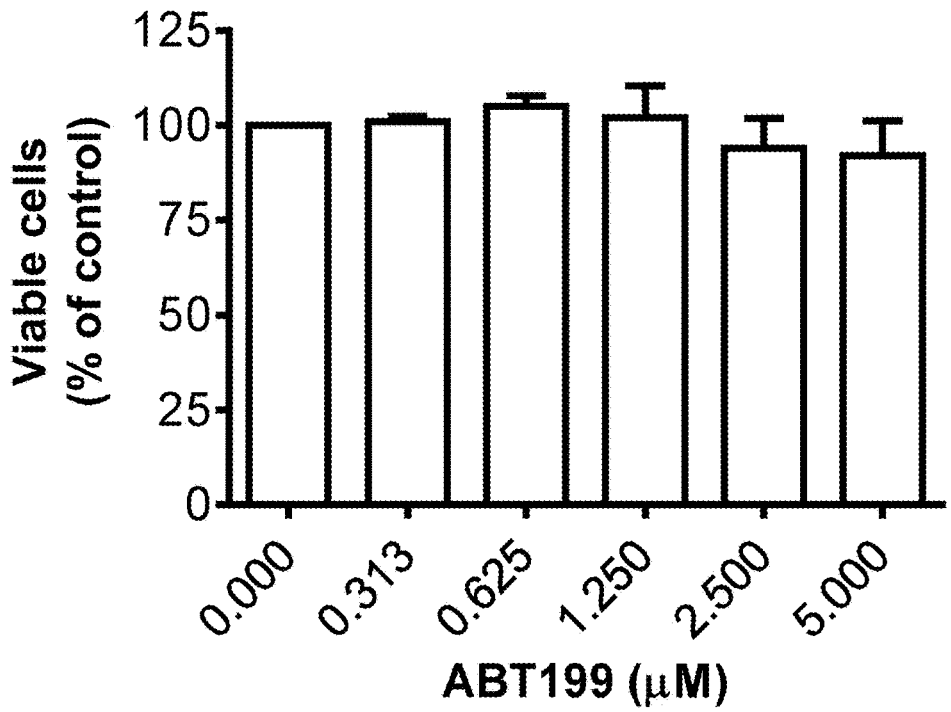
FIG. 8A, FIG. 8B, FIG. 8C and FIG. 8D depict graphs showing inhibition of Bcl-2 or Bcl-xl alone does not selectively kill senescent WI-38 cells.
Figure 8B:
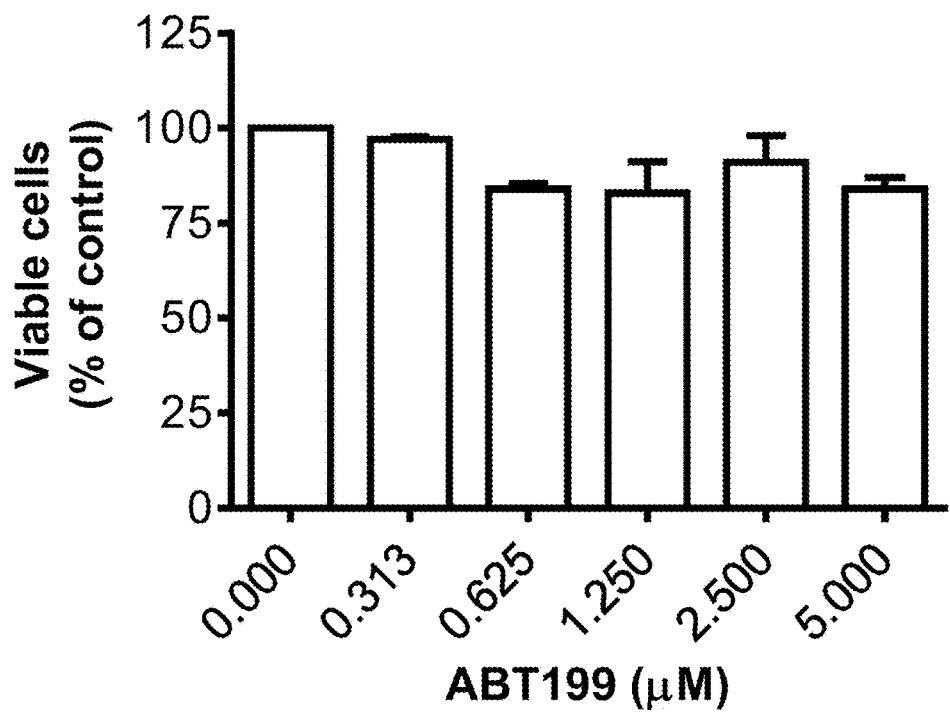
Figure 8C:
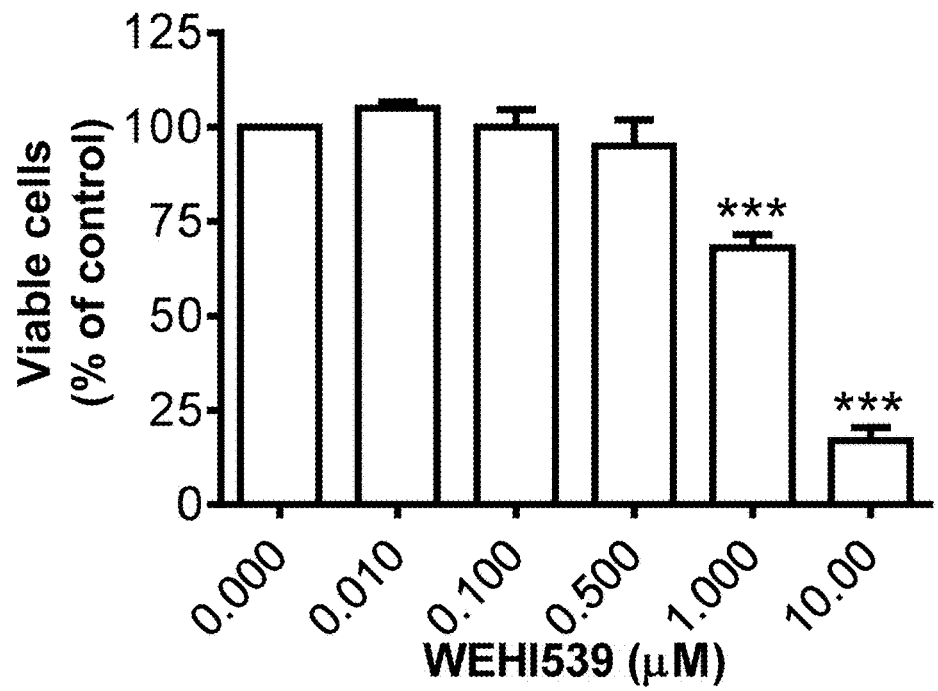
Figure 8D:
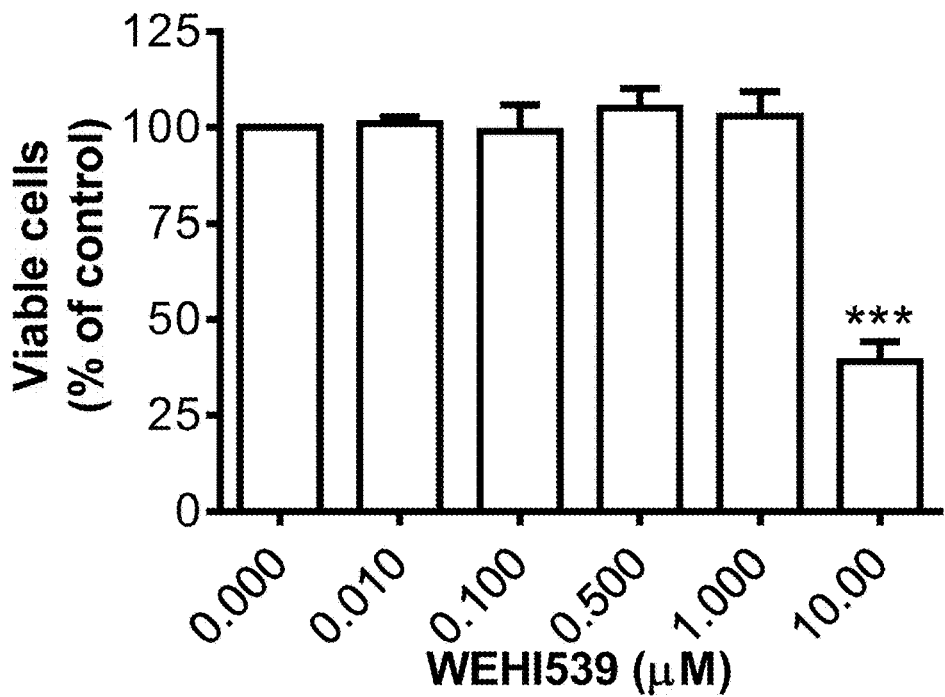

We asked whether SCs are more sensitive to ABT263 than non-senescent cells due to differential expression of anti- or pro-apoptotic proteins as suggested by previous studies[16, 17]. WI-38 cells acquired sensitivity to ABT263 as they expressed increased levels of senescence associated β-galactosidase (SA-β-gal) activity 7 d after IR exposure (FIG. 2G). ABT263 sensitivity correlated with increased expression of Bcl-xl and Bak, but not Bcl-2, Bax, Bad, Bid, Bim and Noxa, (FIG. 2H-K; FIG. 7). Inhibition of Bcl-2 or Bcl-xl alone, using ABT199[18] and WEHI539[19] respectively, did not selectively kill SCs; however, the combination of ABT199 and WEHI539 was selective (FIG. 2L-M; FIG. 8). This finding suggests that Bcl-2 and Bcl-xl are redundant in protecting SCs from death, and that simultaneous inhibition of Bcl-2 and Bcl-xl is required to selectively induce SC apoptosis. Consistent with this idea, downregulation of Bcl-2 or Bcl-xl using shRNAs had minimal effects on SC survival, but downregulation of both proteins reduced SC viability (FIG. 2N).

Example 3

Figure 9A:
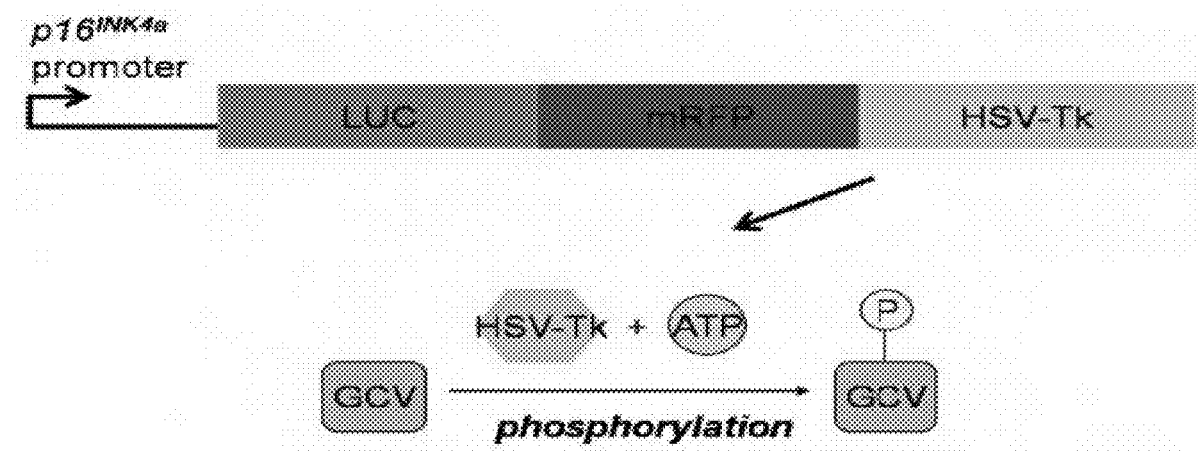
FIG. 9A, FIG. 9B, FIG. 9C, FIG. 9D, FIG. 9E and FIG. 9F depict schematics, images and graphs showing TBI induces SC accumulation in p16-3MR mice in a time dependent manner.
Figure 9B:
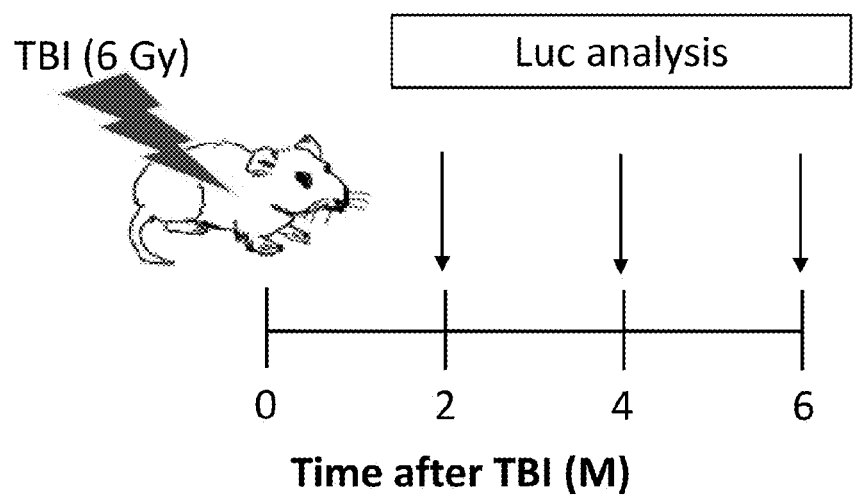
Figure 9C:
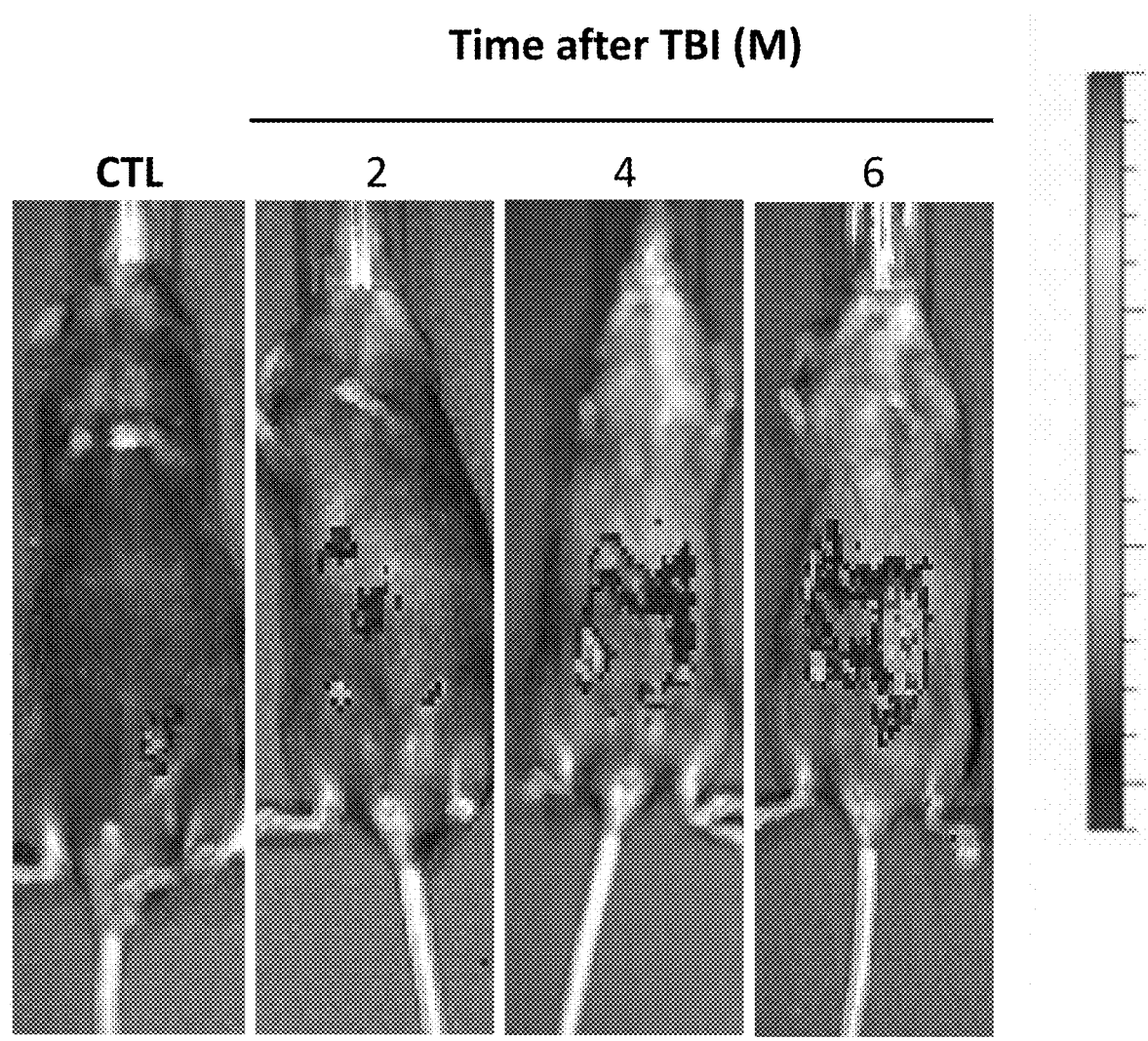
Figure 9D:
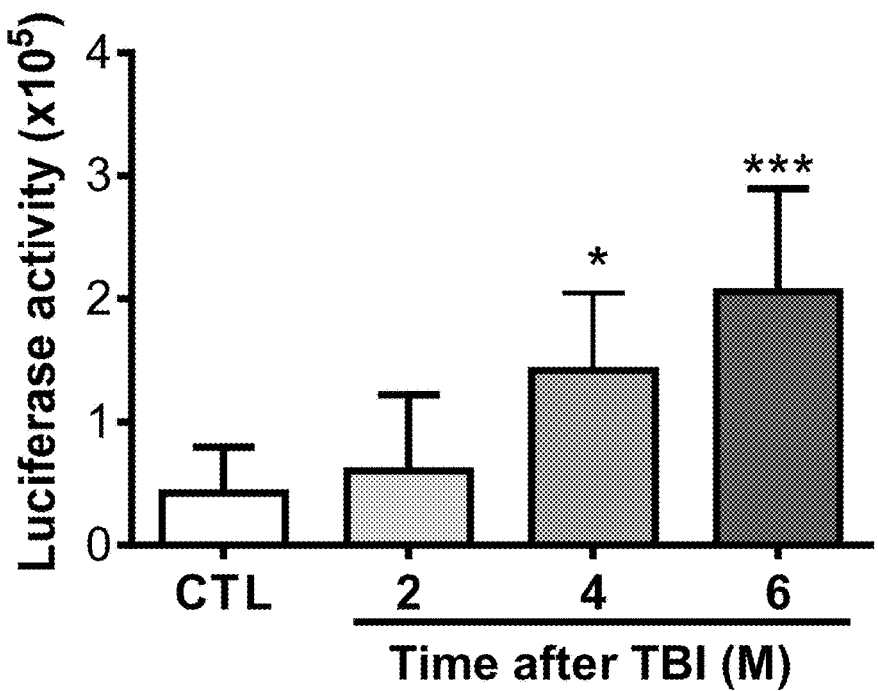
Figure 9E:
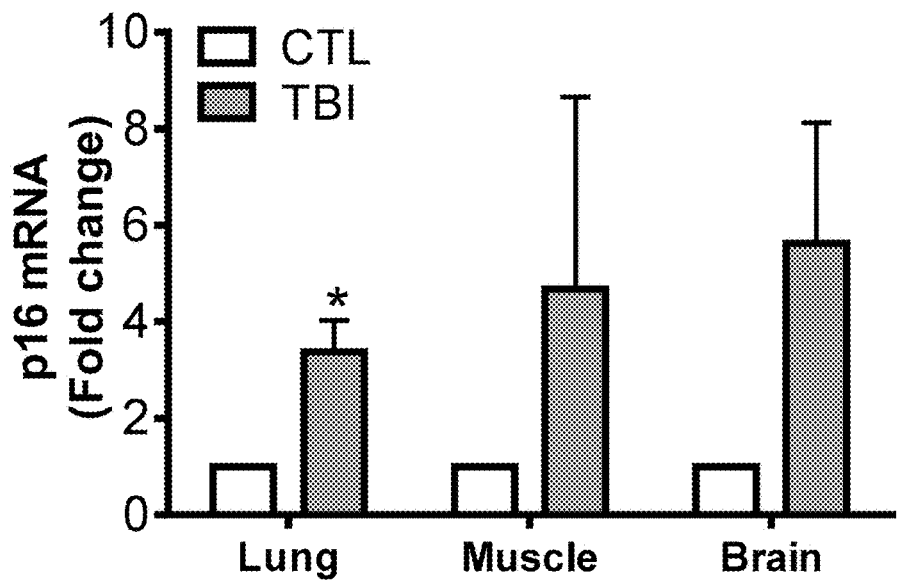
Figure 9F:
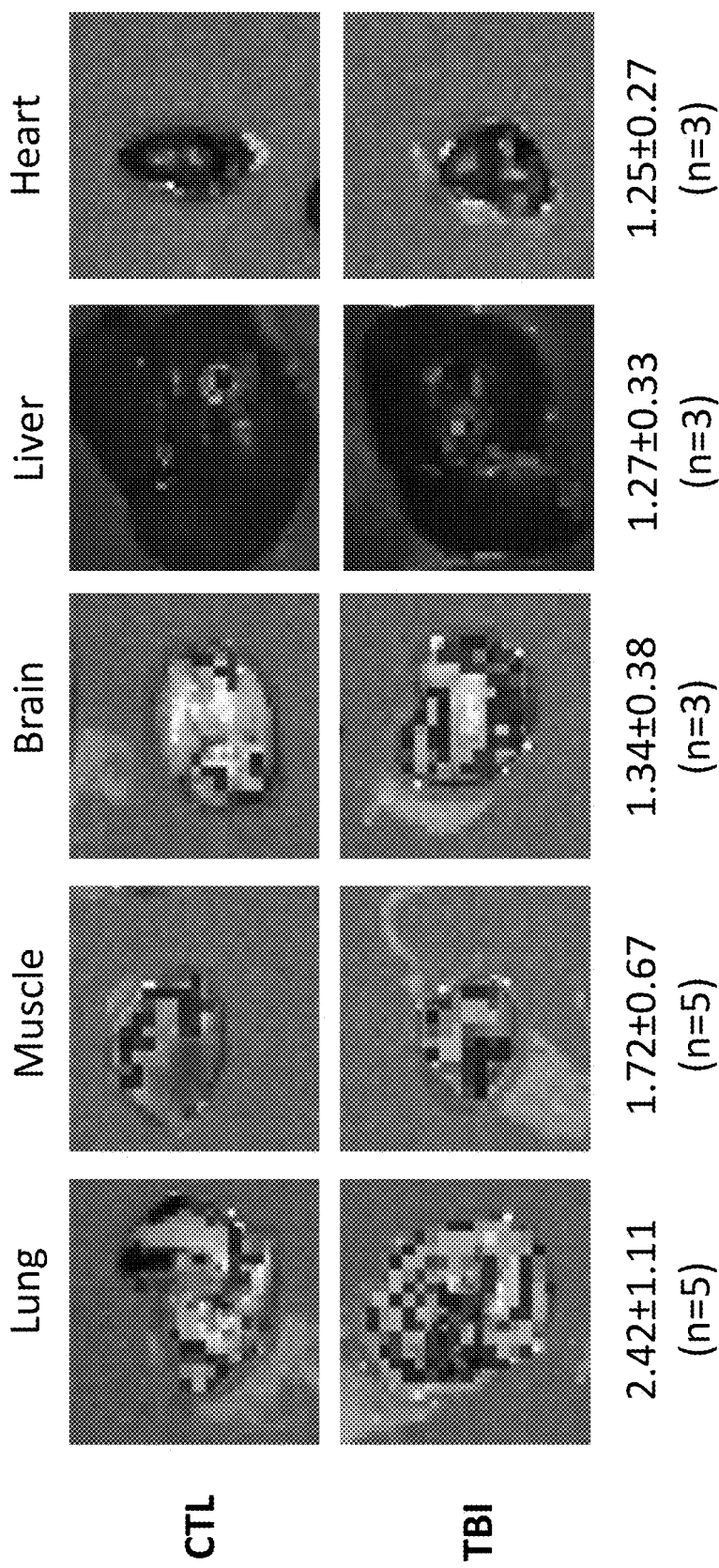
Figure 10A:
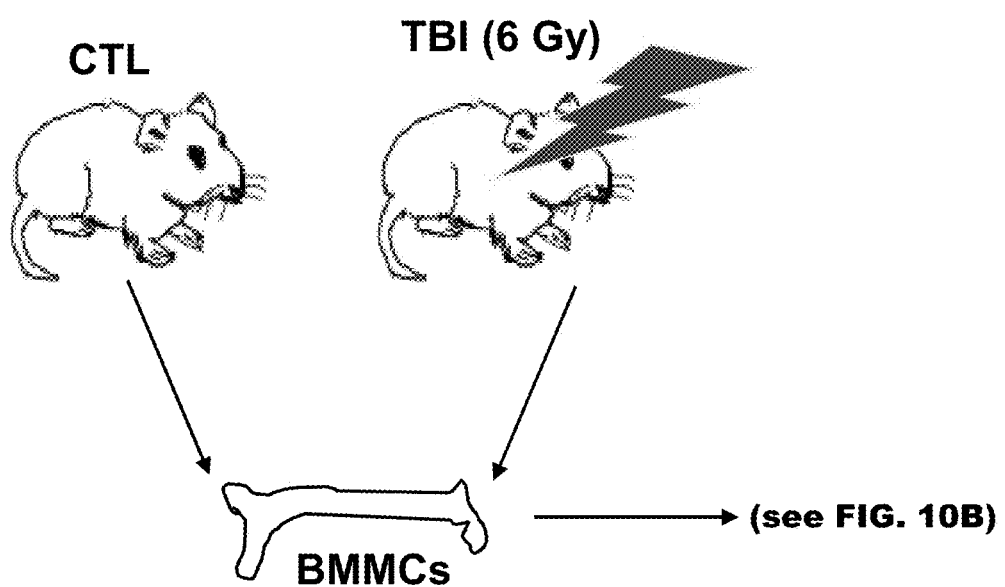
FIG. 10A, FIG. 10B, FIG. 10C, FIG. 10D and FIG. 10E depict a schematic, flow cytometry analysis and graphs showing ABT263 selectively depletes senescent HSCs induced by TBI in vitro.
Figure 10B:
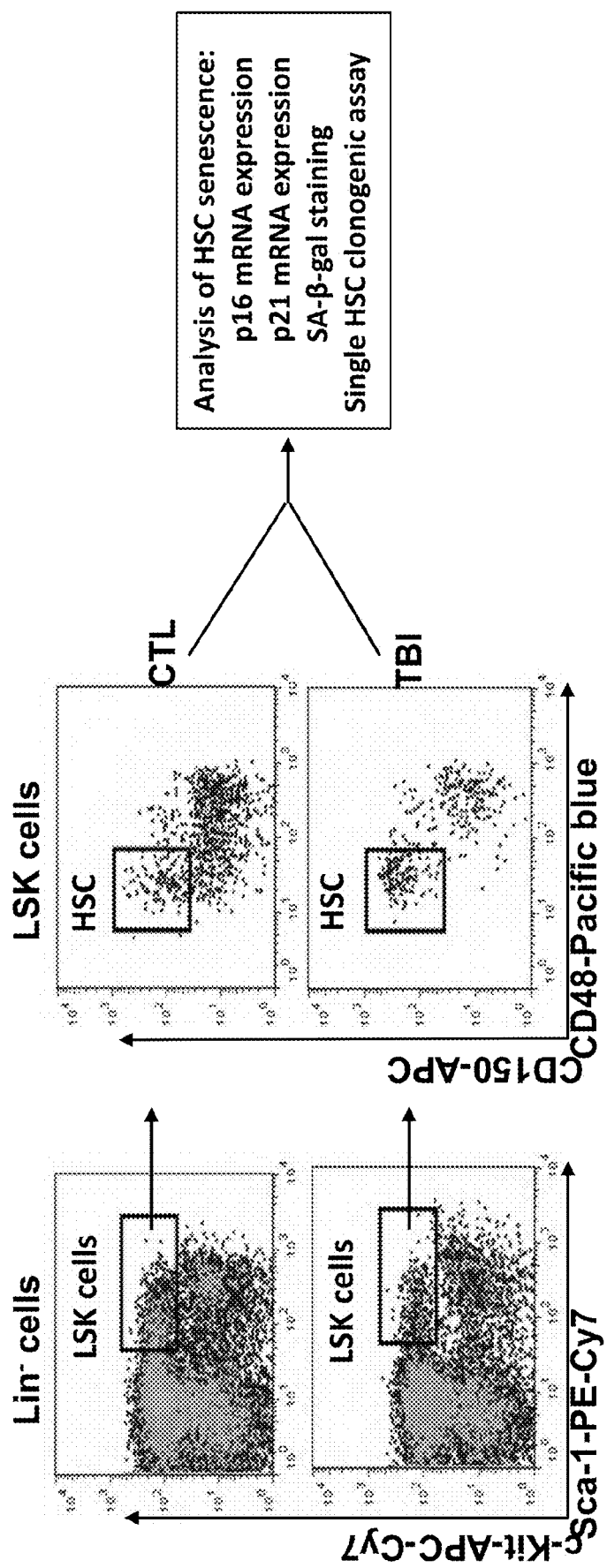
Figure 10C:
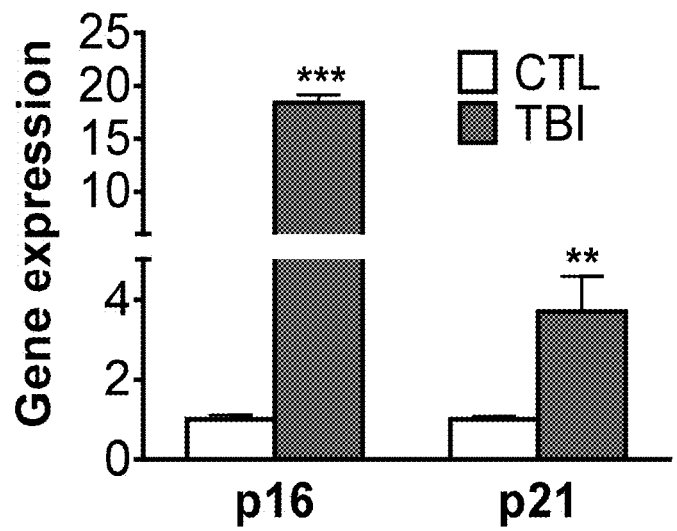
Figure 10D:
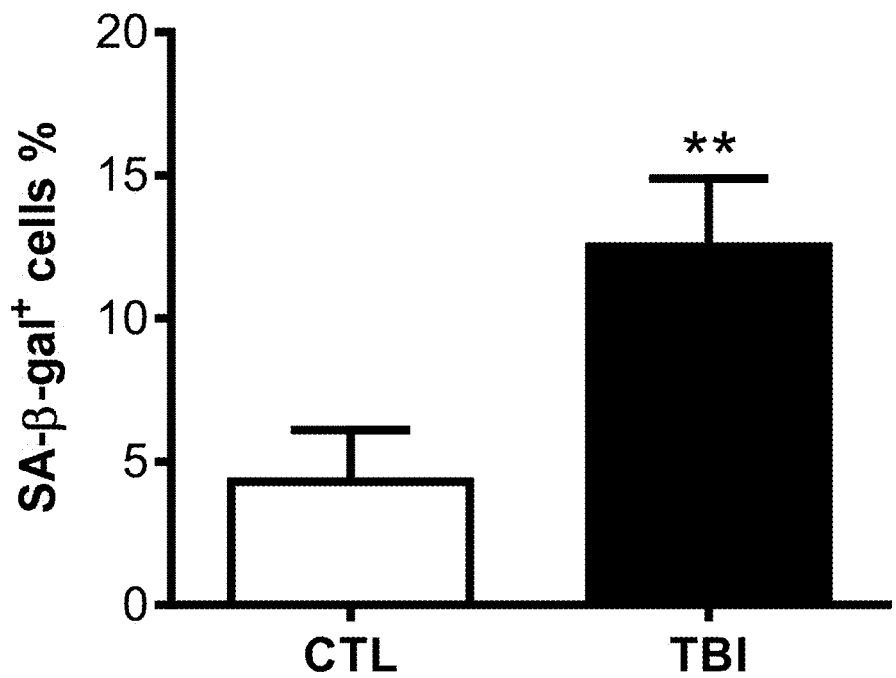
Figure 10E:
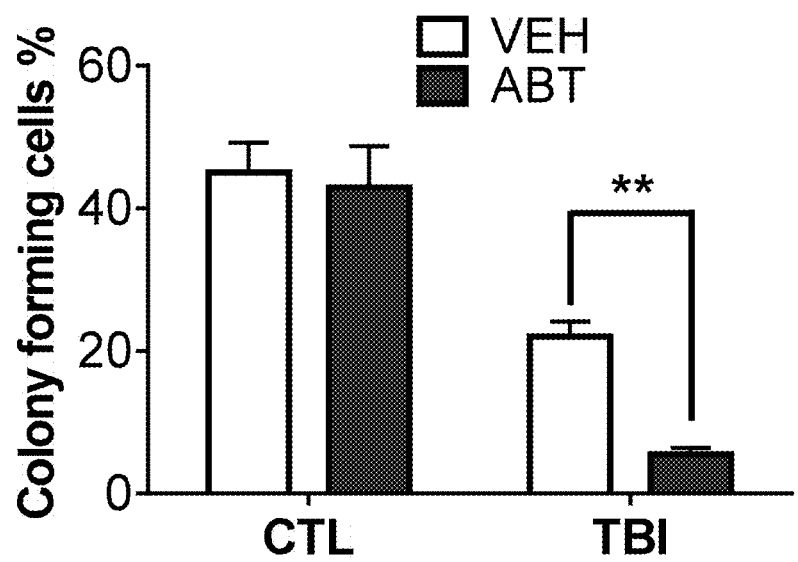
Figure 11A:
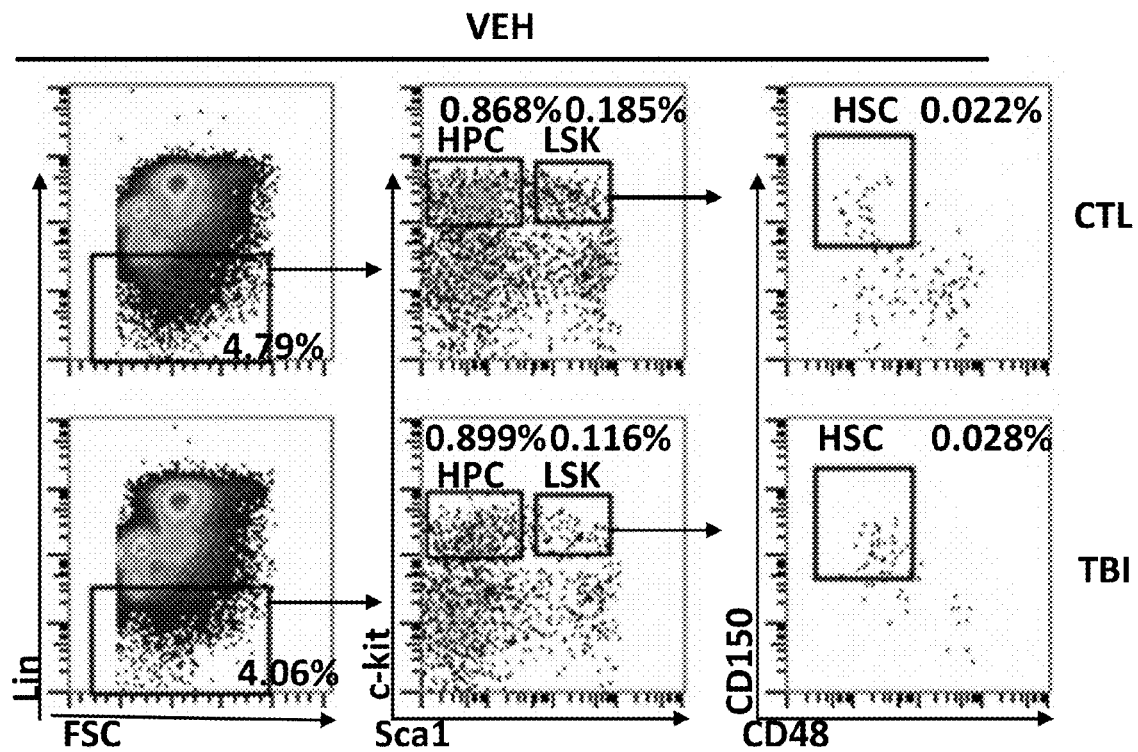
FIG. 11A, FIG. 11B, FIG. 11C, FIG. 11D, FIG. 11E and FIG. 11F depict flow cytometry analyses and graphs showing clearance of senescent HSC by ABT263 does not reduce bone marrow HSCs and HPCs in mice.
Figure 11B:
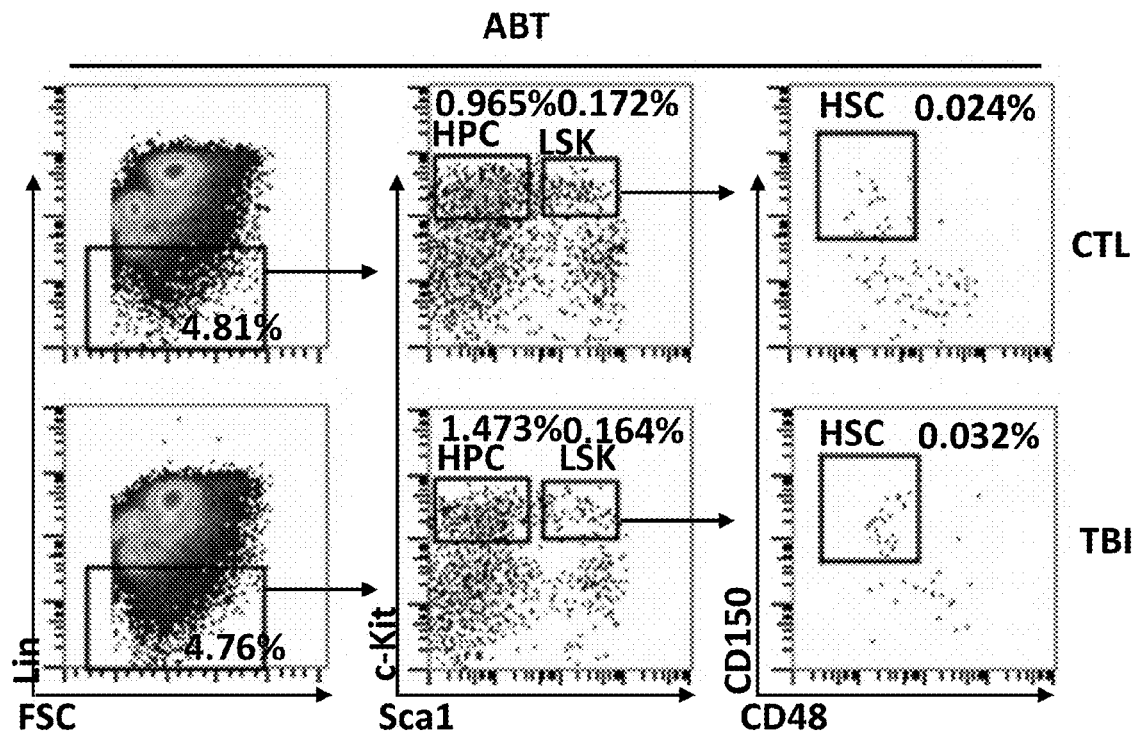
Figure 11C:
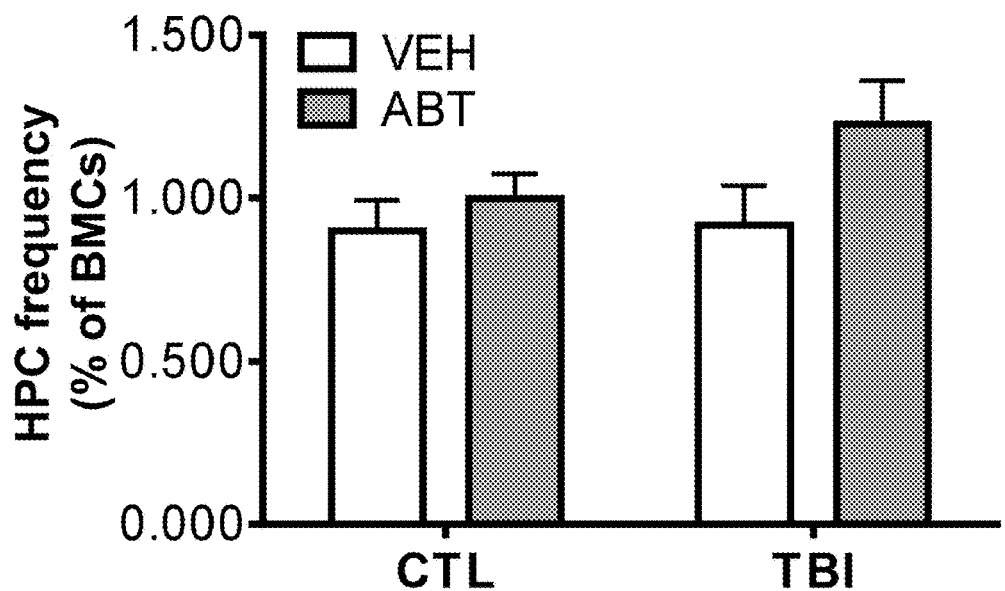
Figure 11D:
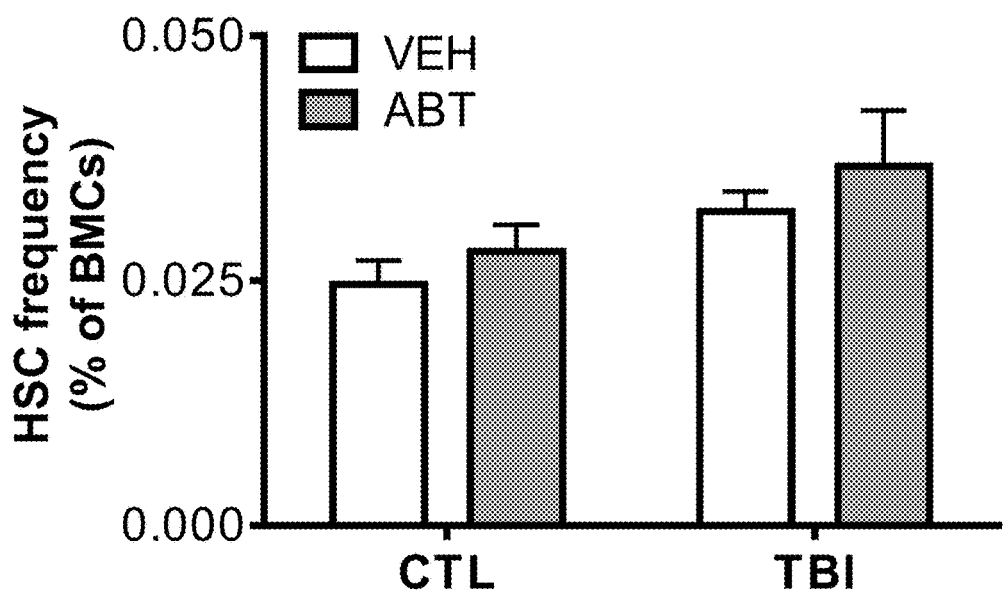
Figure 11E:
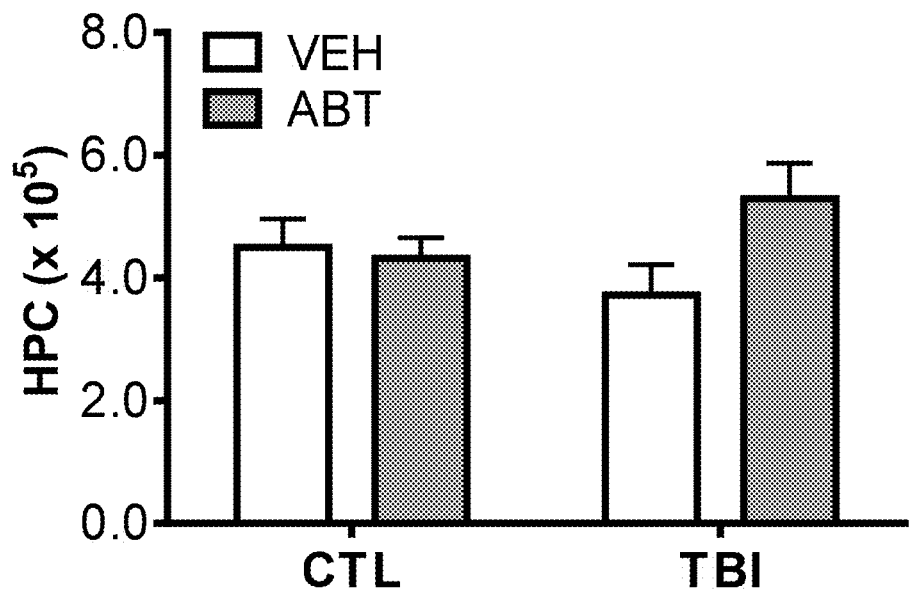
Figure 11F:
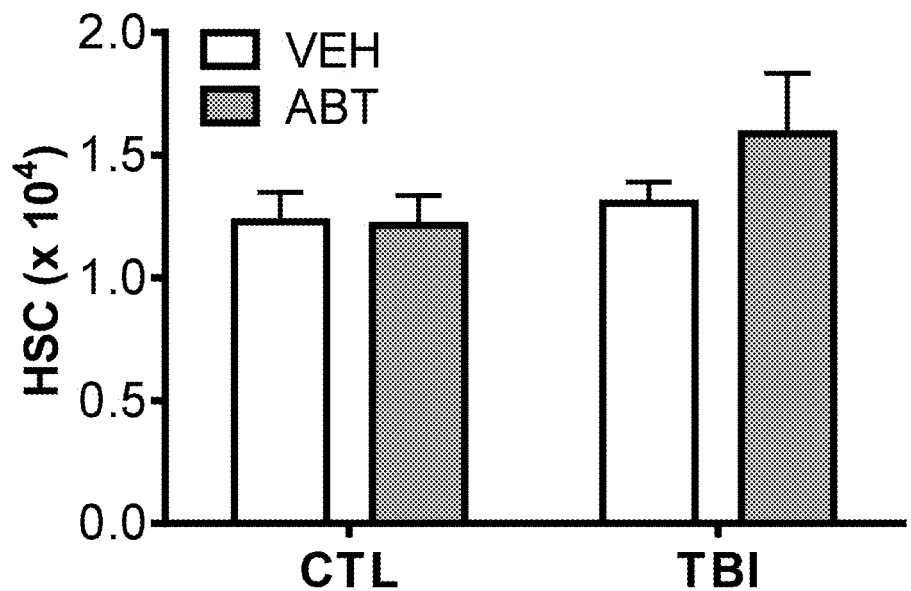
Figure 12A:
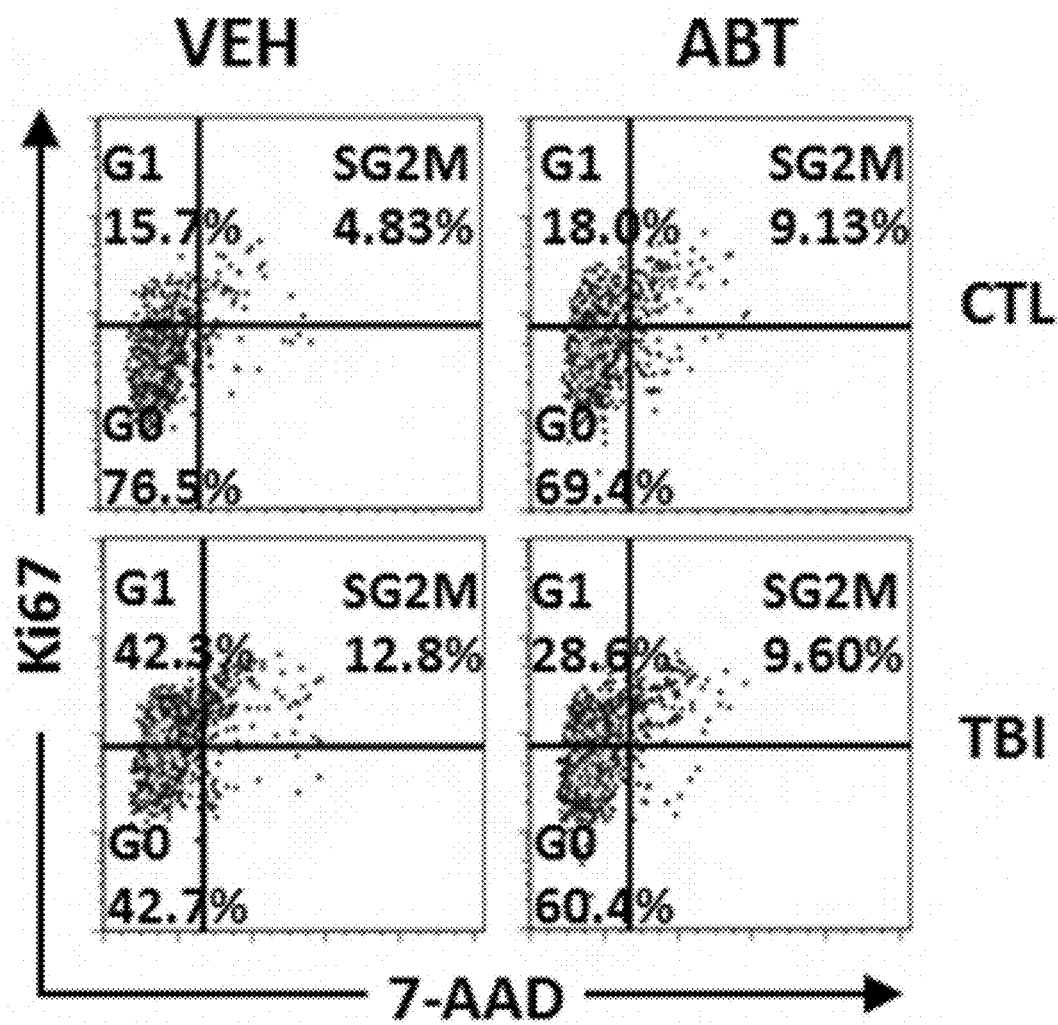
FIG. 12A, FIG. 12B, FIG. 12C and FIG. 12D depict flow cytometry analyses and graphs showing clearance of senescent HSC by ABT263 attenuates TBI-induced disruption of HSC quiescence and the presence of HSCs with persistent DNA damage.
Figure 12B:
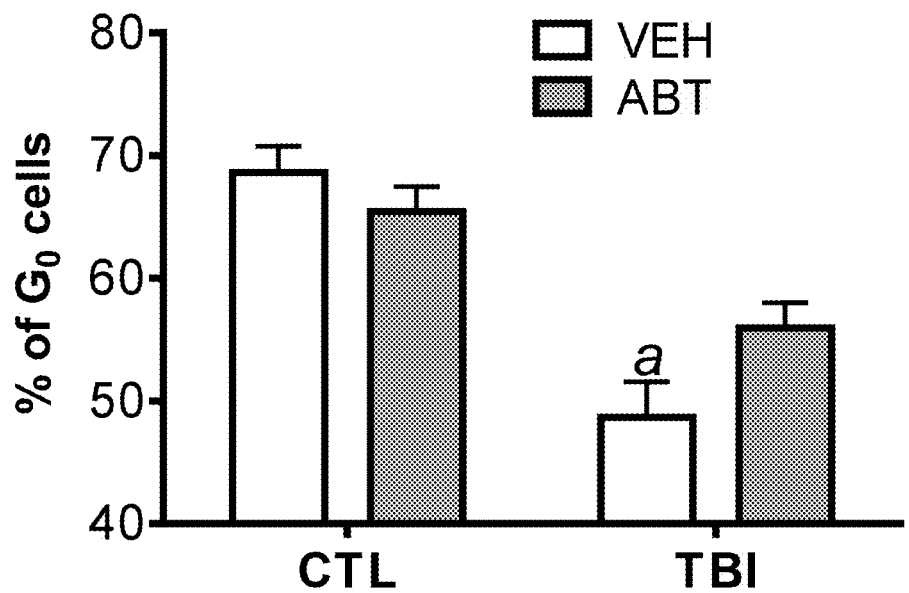
Figure 12C:
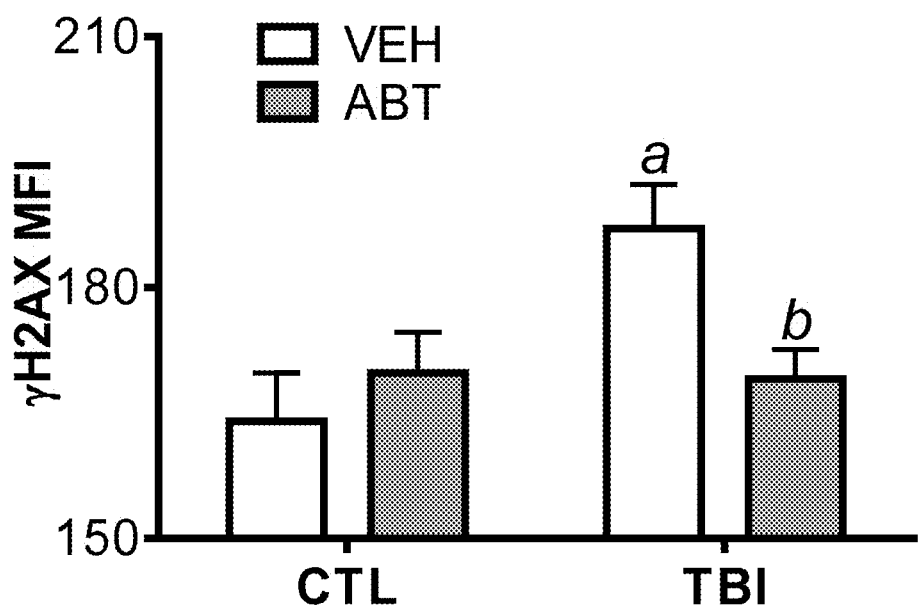
Figure 12D:
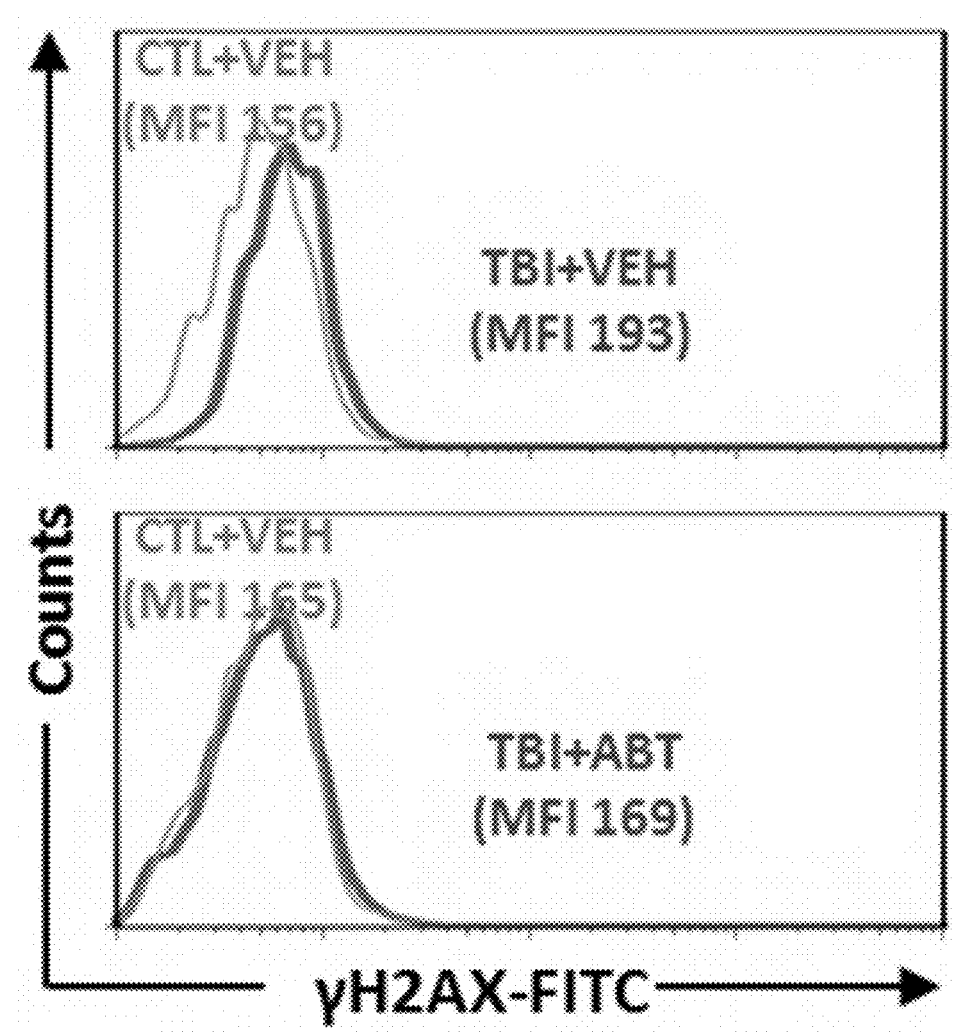
Figure 13A:
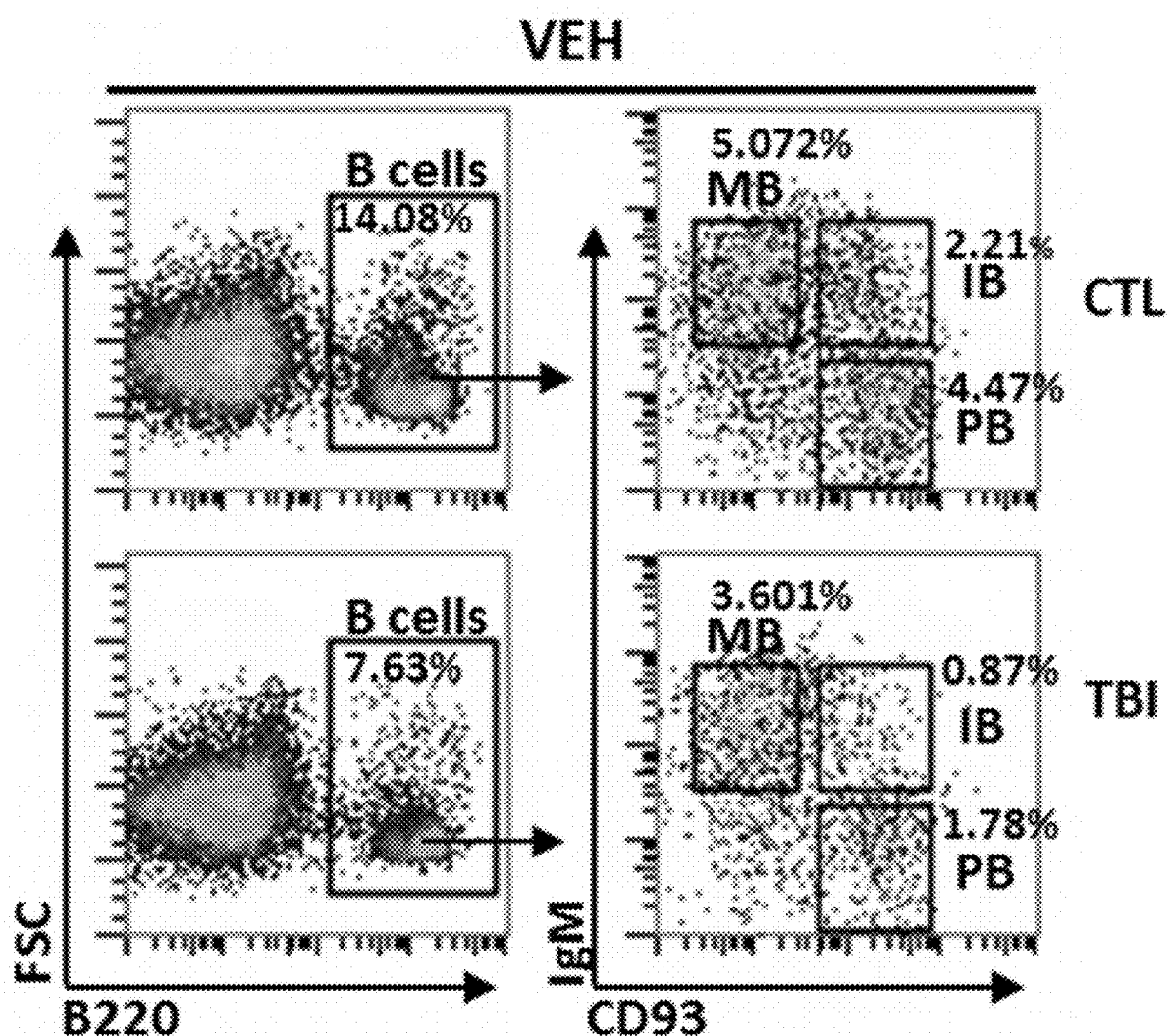
FIG. 13A, FIG. 13B, FIG. 13C, FIG. 13D, FIG. 13E and FIG. 13F depict flow cytometry analyses and graphs showing clearance of senescent HSC by ABT263 promotes B cell lymphopoiesis.
Figure 13B:
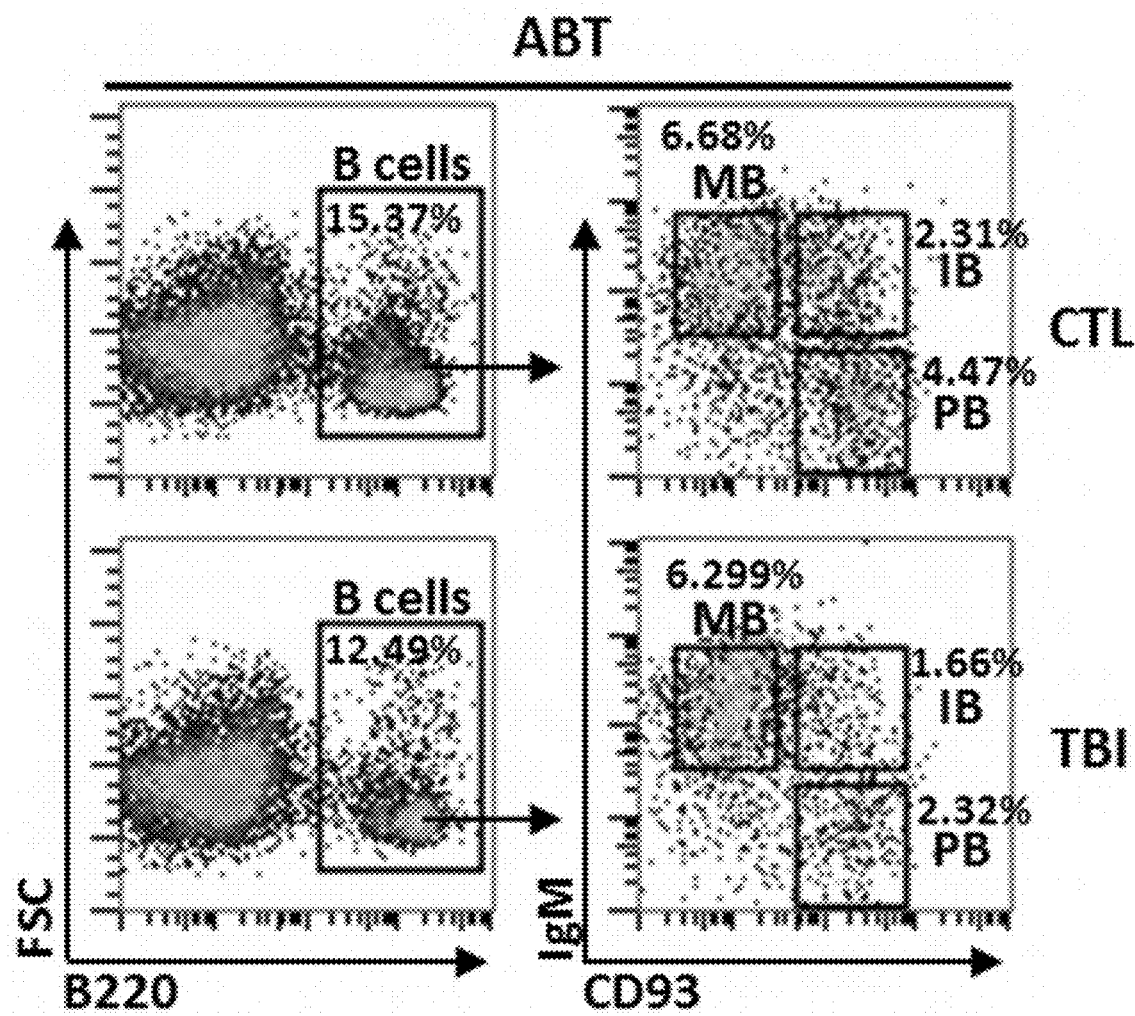
Figure 13C:
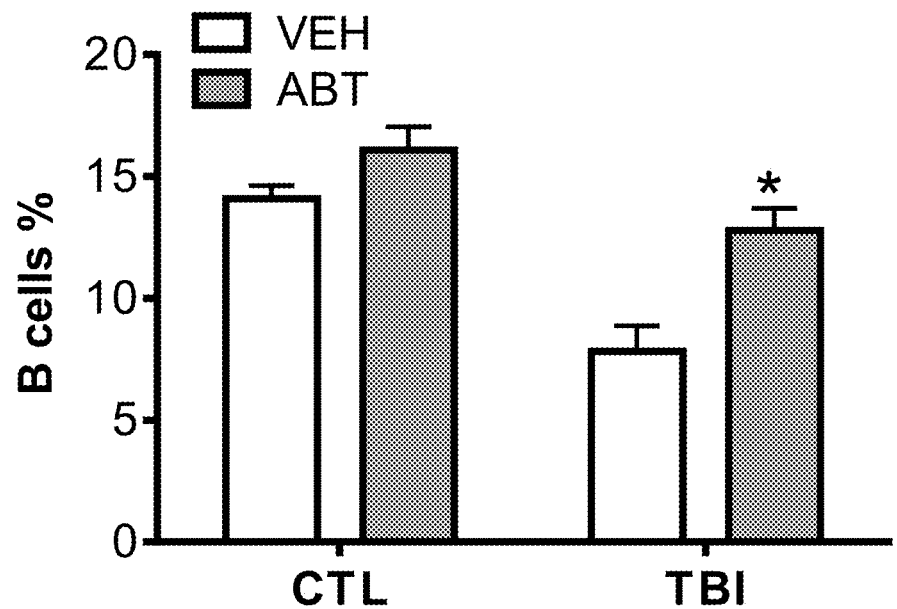
Figure 13D:
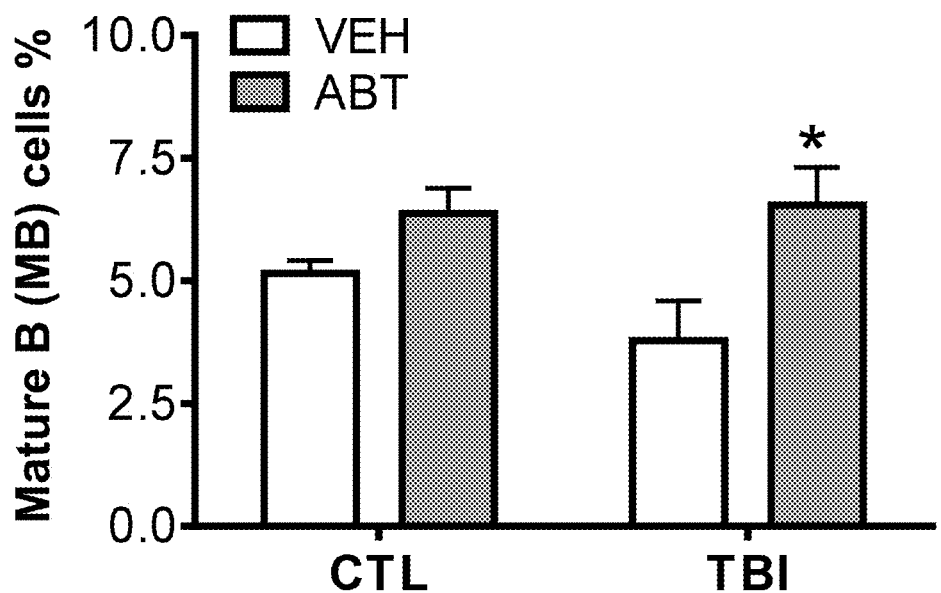
Figure 13E:
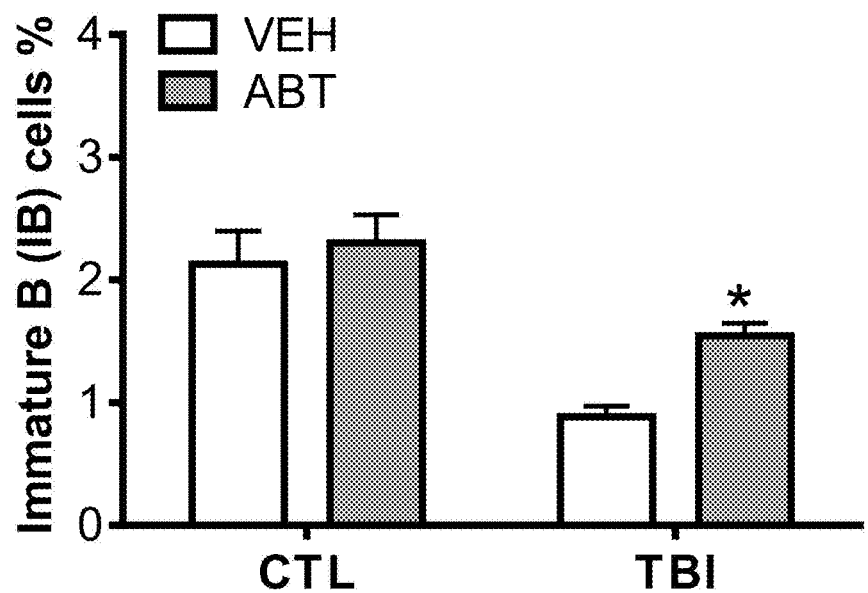
Figure 13F:
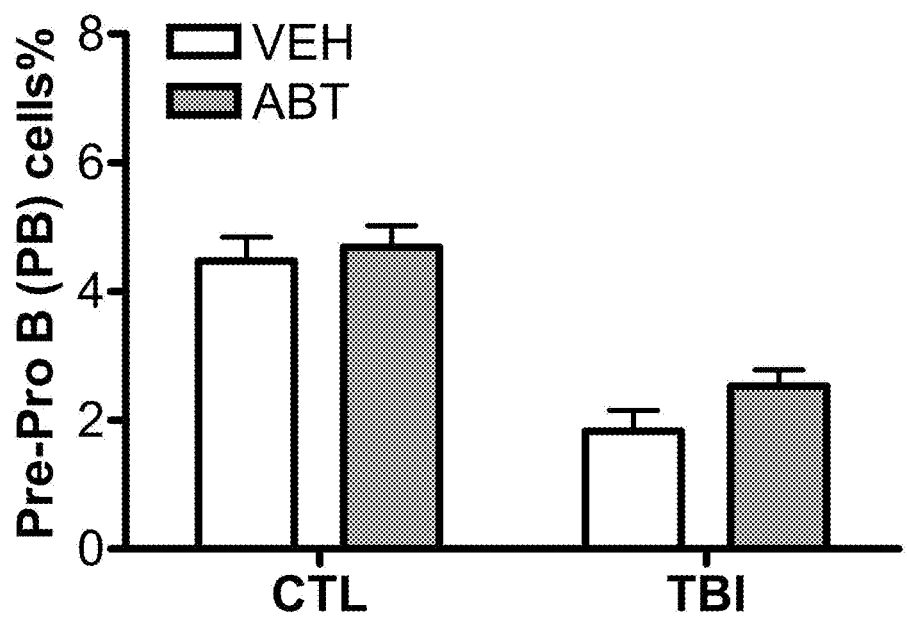

ABT263 Clears Senescent Cells and Inhibits the Senescence-Associated Secretory Phenotype (SASP) in TBI p16-3MR Mice as Effectively as Ganciclovir Because p16 is a widely-used SC biomarker and a modulator of stem cell aging[20-22], SC accumulation and clearance can be monitored in vivo by bioluminescence using p16-3MR transgenic mice, which carry the luciferase-containing trimodal reporter protein (3MR) under control of the p16 promoter (FIG. 9A)[23]. We exposed young (2 month old) p16-3MR mice to sublethal TBI (6 Gy). The irradiated mice showed a time-dependent increase in SCs in 6 months after TBI, as determined by luminescence (FIG. 9B-D), whereas non-irradiated p16-3MR mice show little luminescence up to 8 months of age[23]. These findings agree with observations that SCs are rare in normal mice before 40 weeks of age[20, 21], but rapidly accumulate after exposure to genotoxic insults that promote aging or tumorigenesis[20, 21]. Lungs showed the greatest increase in SCs after TBI, followed by skeletal muscle and brain; liver and heart showed minimal increases (FIG. 9E-F).

Figure 3A:
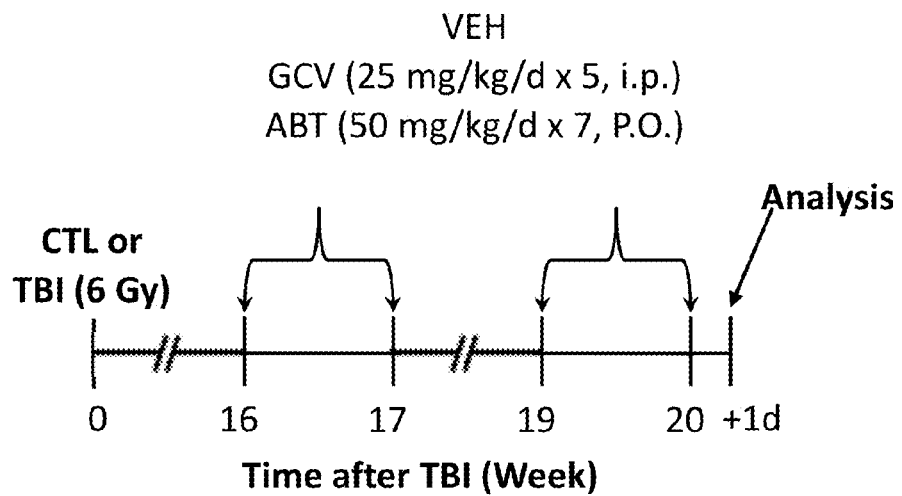
FIG. 3A, FIG. 3B, FIG. 3C, FIG. 3D, FIG. 3E, FIG. 3F, FIG. 3G, FIG. 3H, FIG. 3I and FIG. 3J depict a schematic, images and graphs showing that ABT263 clears senescent cells and inhibits the senescence-associated secretory phenotype (SASP) in TBI p16-3MR mice as effectively as ganciclovir.
Figure 3B:
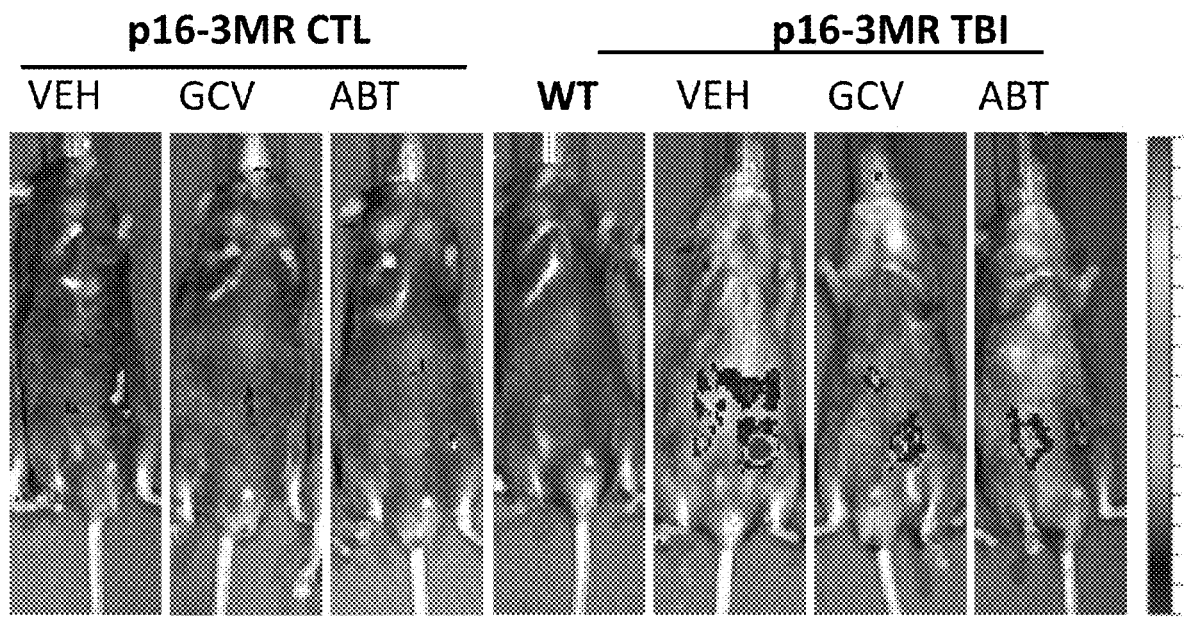
Figure 3C:
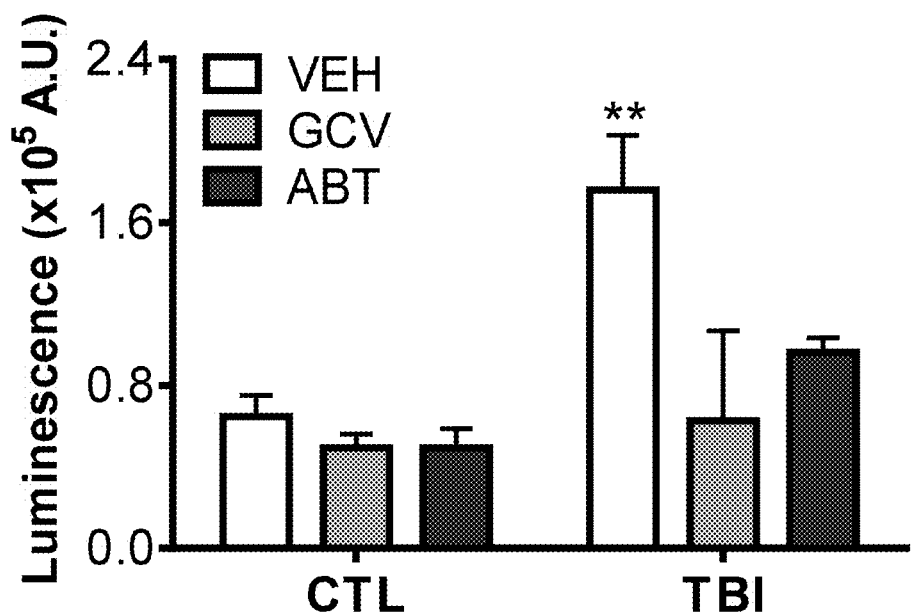
Figure 3D:
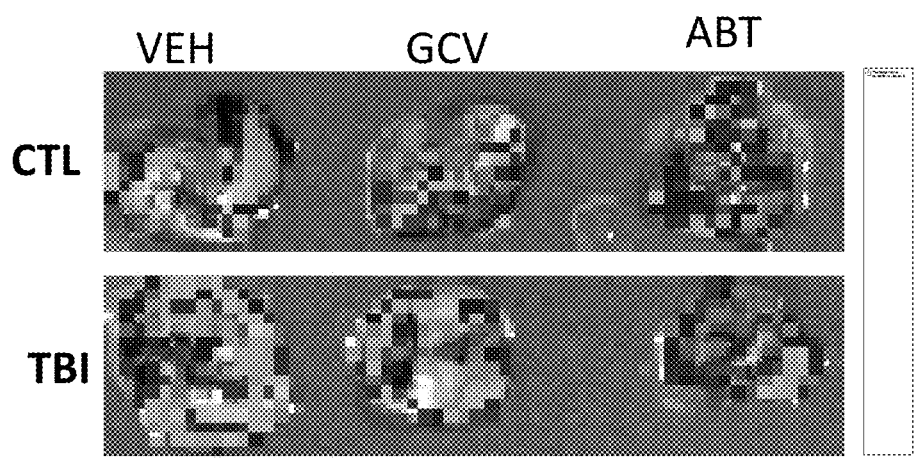
Figure 3E:
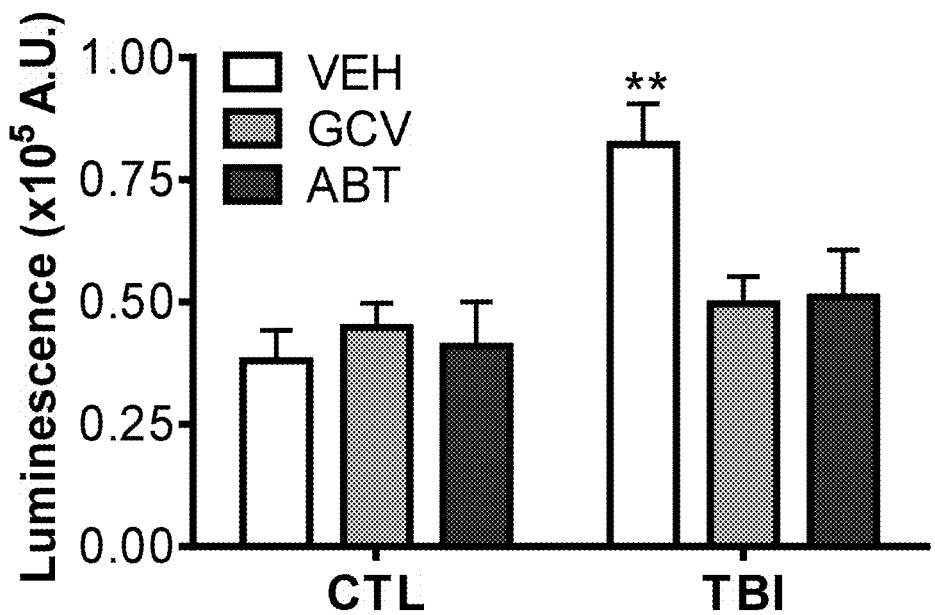
Figure 3F:
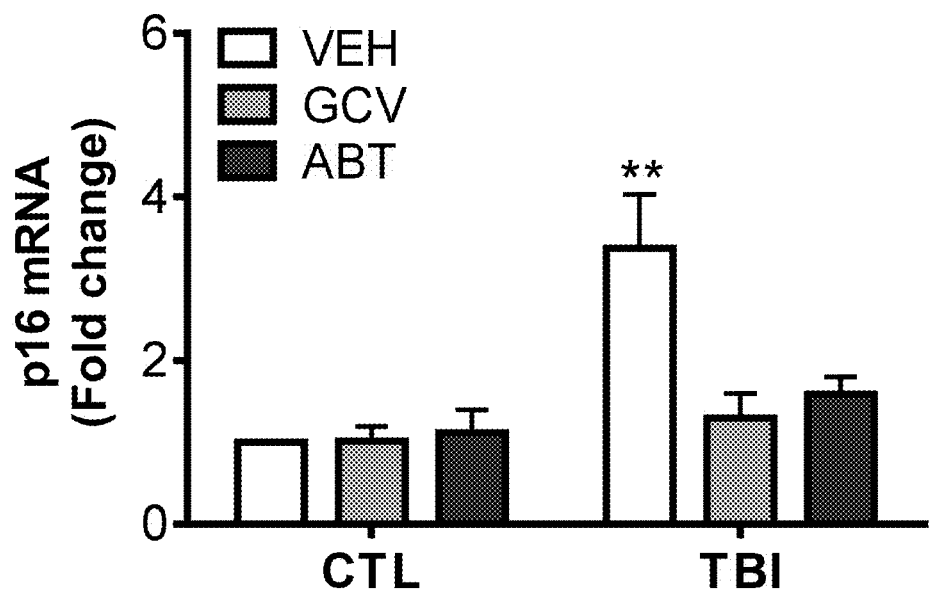
Figure 3G:
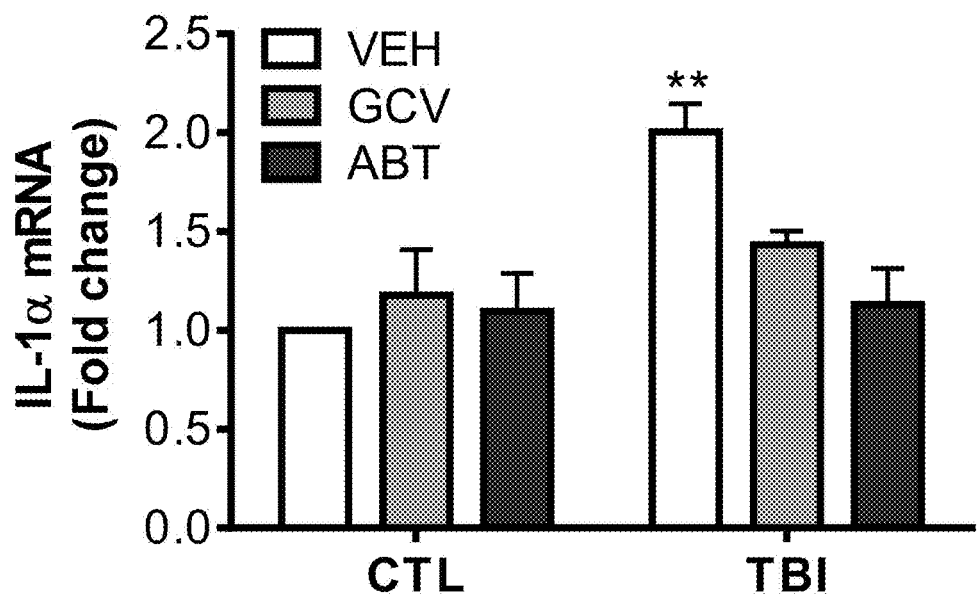
Figure 3H:
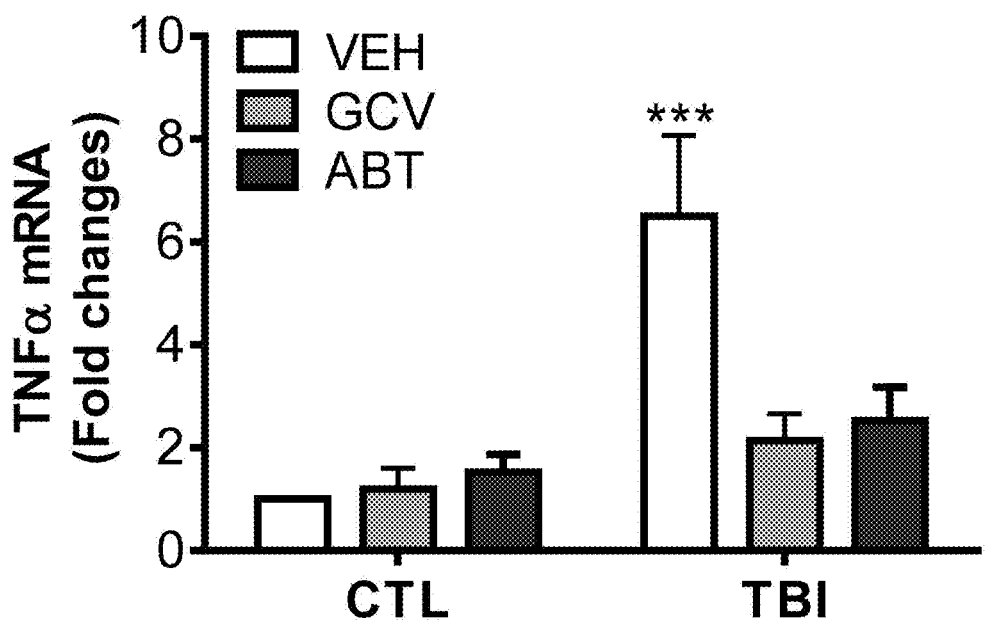
Figure 3I:
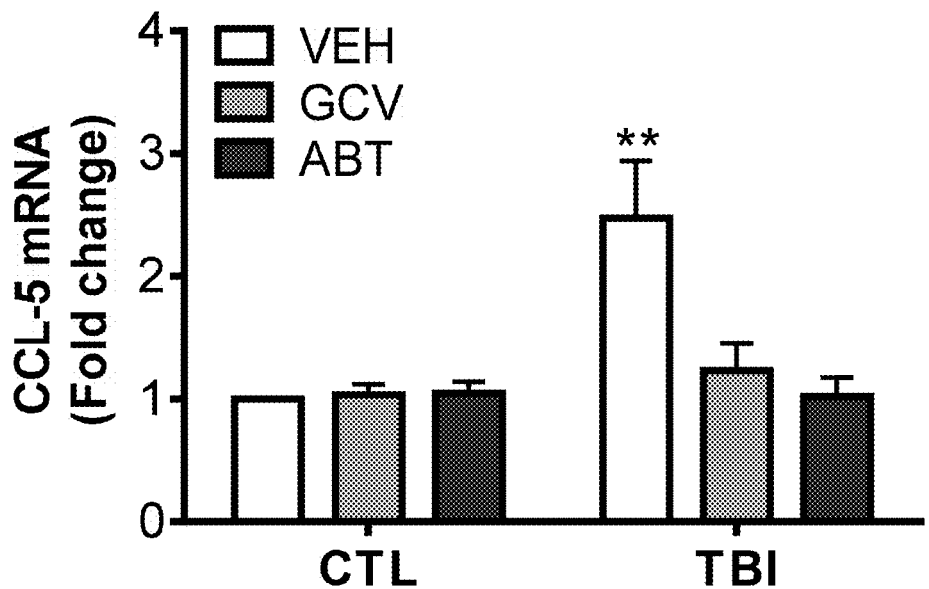
Figure 3J:
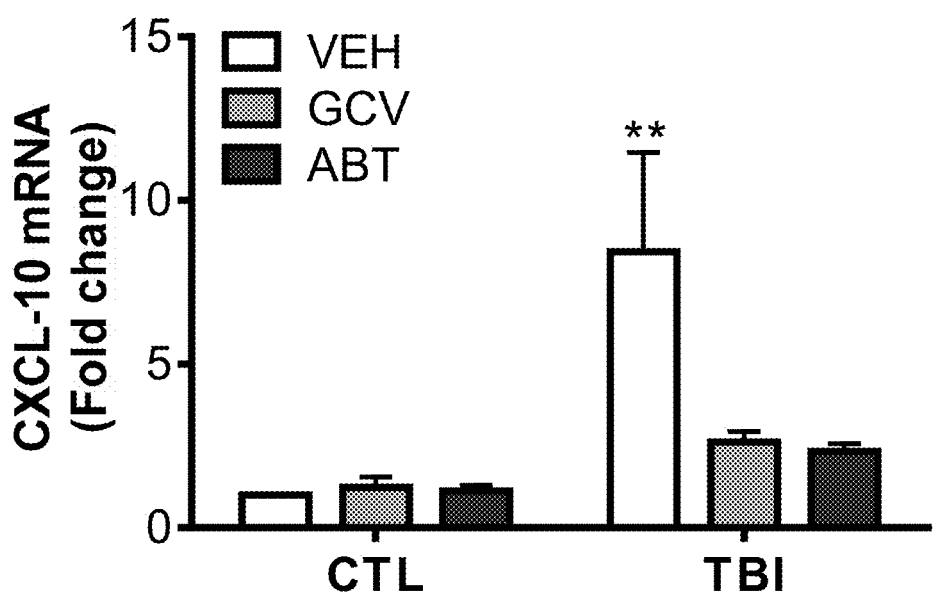

The p16-3MR transgene can selectively kill p16-positive SCs in vivo because 3MR also contains the herpes simplex virus thymidine kinase (HSV-TK), which phosphorylates ganciclovir (GCV), converting it into a toxic DNA chain terminator; we showed that phosphorylated GCV incorporates into mitochondrial DNA, causing apoptotic cell death[24], and, at the doses used, is non-toxic to wild-type or p16-3MR mice[23]. Two GCV treatment cycles effectively cleared SCs induced by IR in p16-3MR mice; strikingly, ABT263 acted similarly (FIG. 3A-C). SC clearance was confirmed by analyzing lungs. GCV and ABT263 not only reduced IR-induced SCs (FIG. 3D-F) but also suppressed the SASP induced by TBI[25] (FIG. 3G-J). Thus, ABT263 was as effective as GCV in clearing IR-induced SCs in irradiated p16-3MR mice.

Example 4

ABT263 can Clear Senescent HSCs In Vivo to Mitigate TBI-Induced Premature Hematopoietic Aging and LT-BM Injury HSC senescence is thought to be an underlying cause of IR-induced LT-BM injury[26]. Senescent HSCs induced by IR exhibit alterations similar to those seen in HSCs from aged animals, including decreased self-renewal, clonogenicity and long-term repopulating ability, and myeloid skewing[4, 26-29]. Therefore, IR-induced LT-BM injury is a model of premature hematopoietic system aging[4, 26-32]. In addition, LT-BM injury can promote hypoplastic anemia, myelodysplastic syndrome or leukemia over time or following additional hematopoietic stress in irradiated patients[33-35].

Figure 4A:
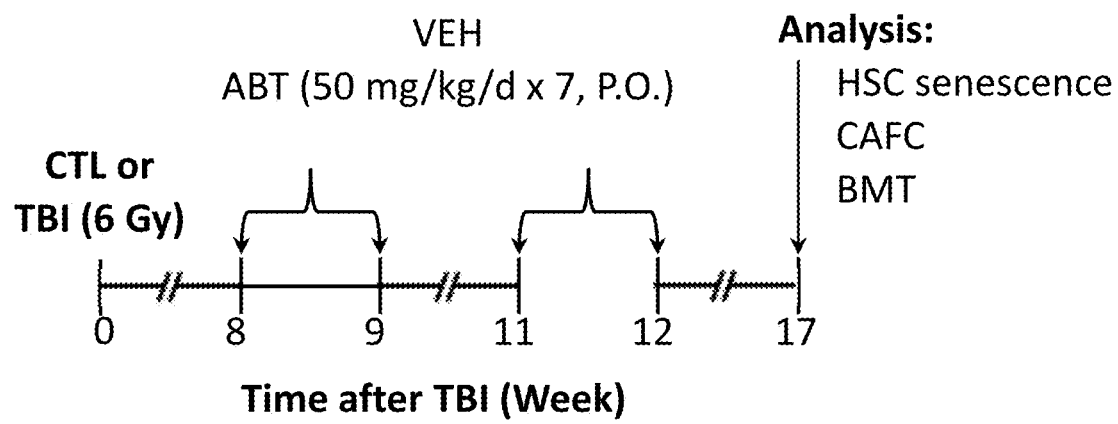
Figure 4B:
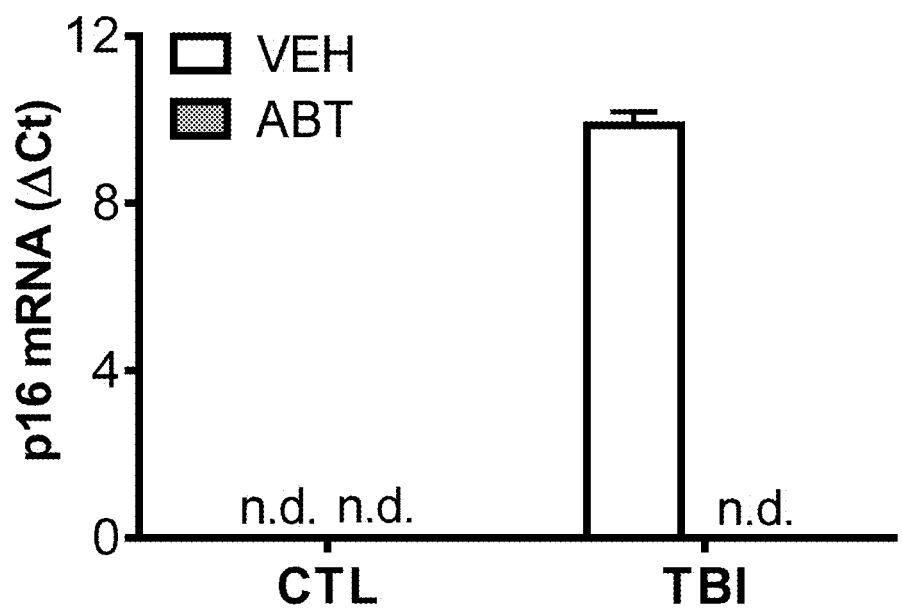
Figure 4C:
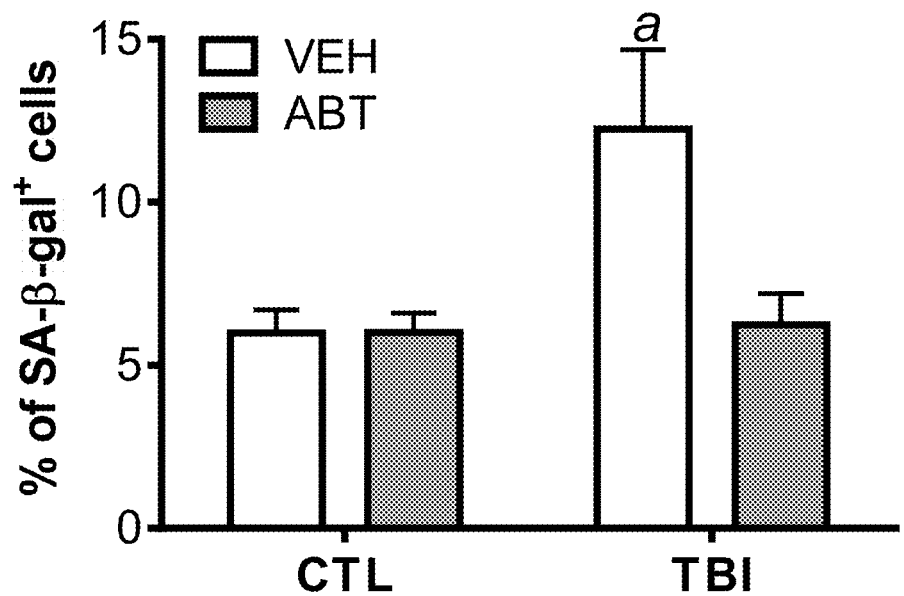
Figure 4D:
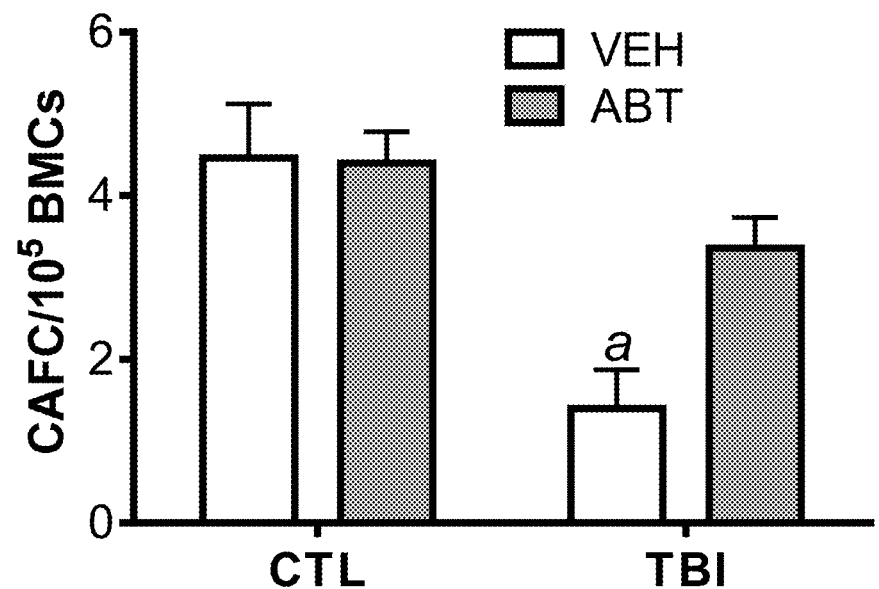
Figure 4E:
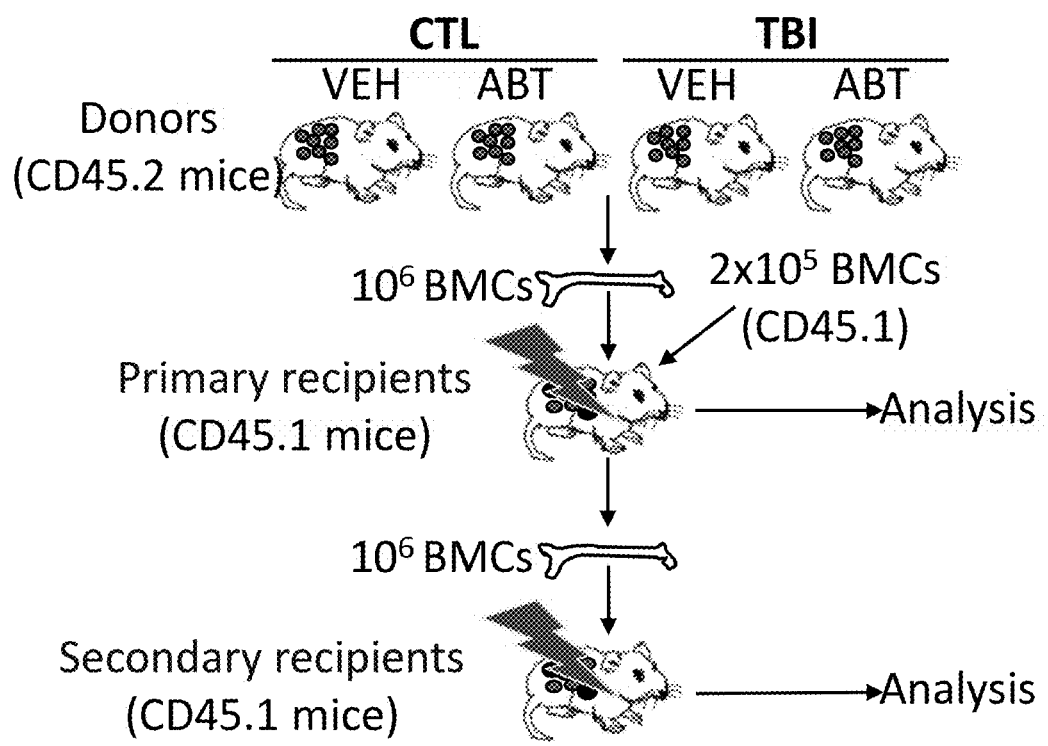
Figure 4H:
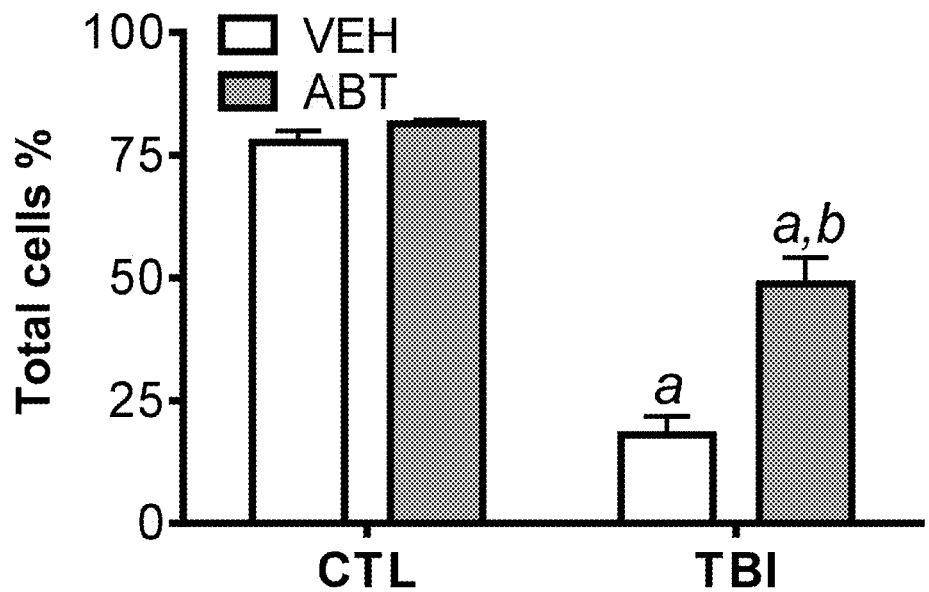
Figure 4I:
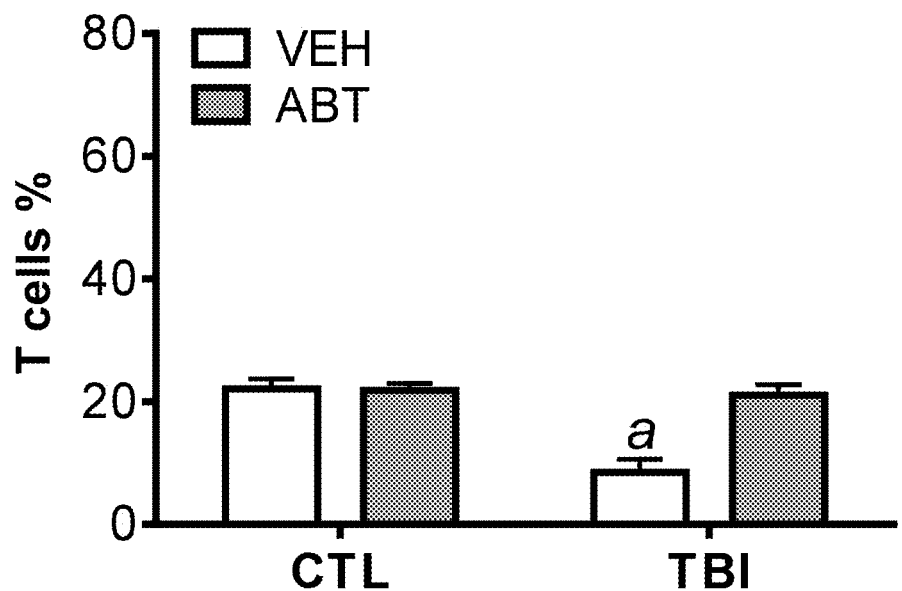
Figure 4J:
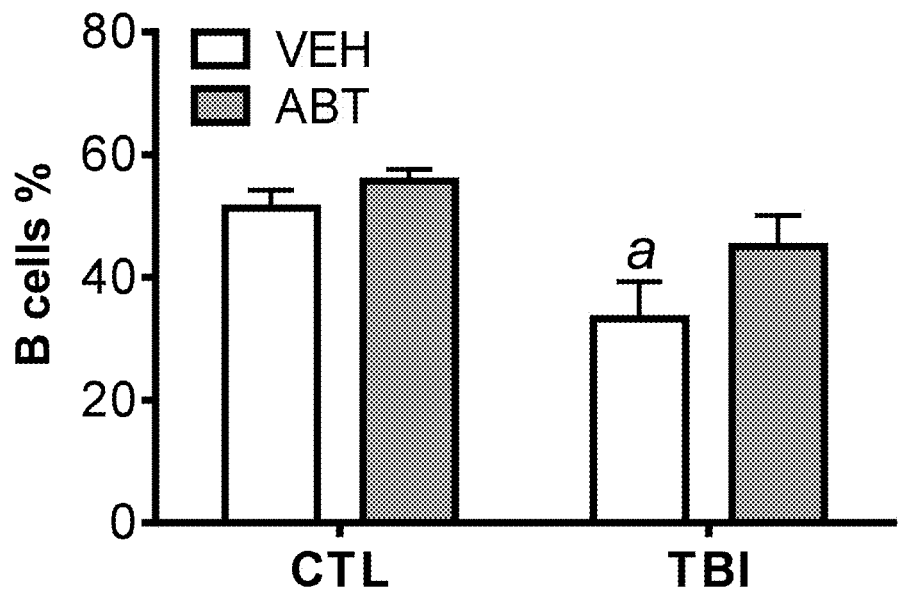
Figure 4K:
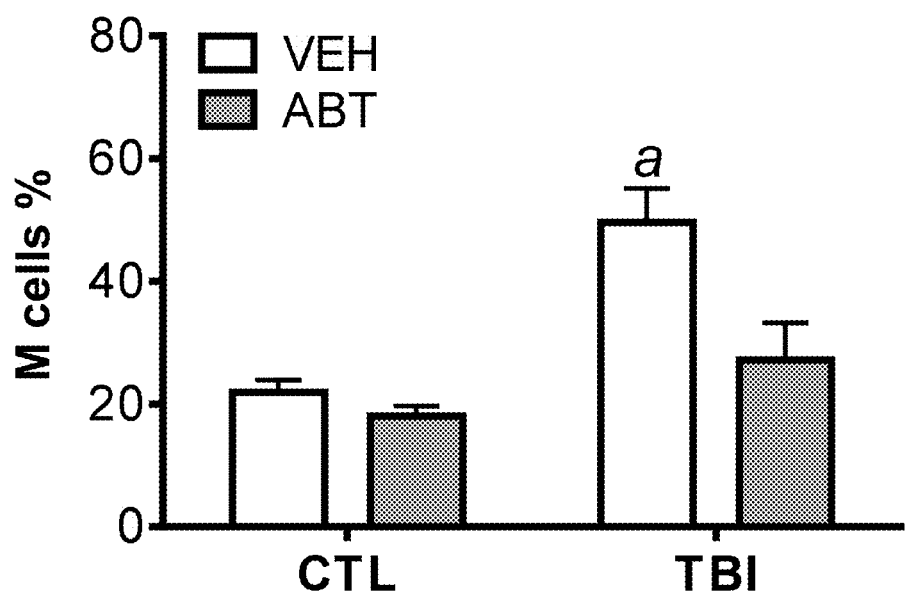
Figure 4L:
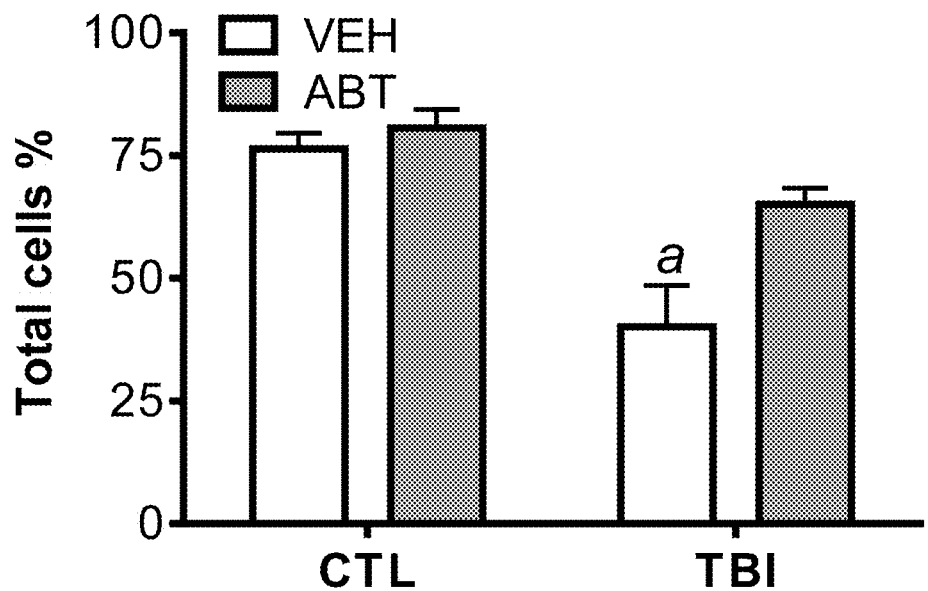
Figure 4M:
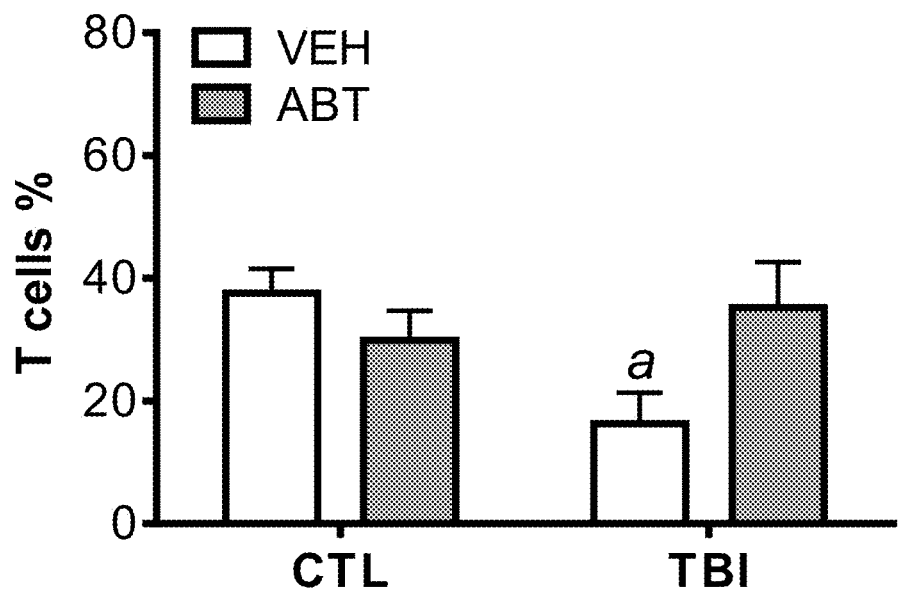
Figure 4N:
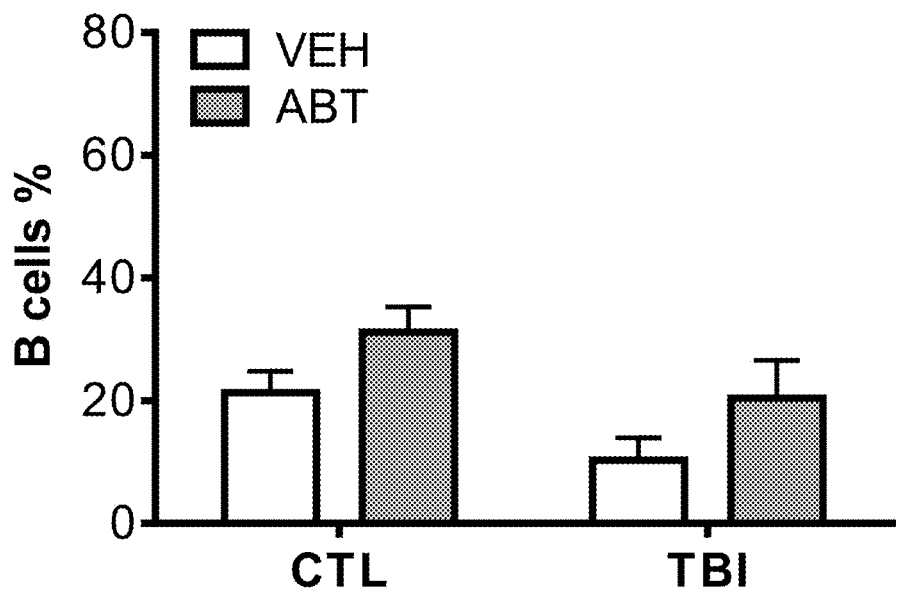
Figure 4O:
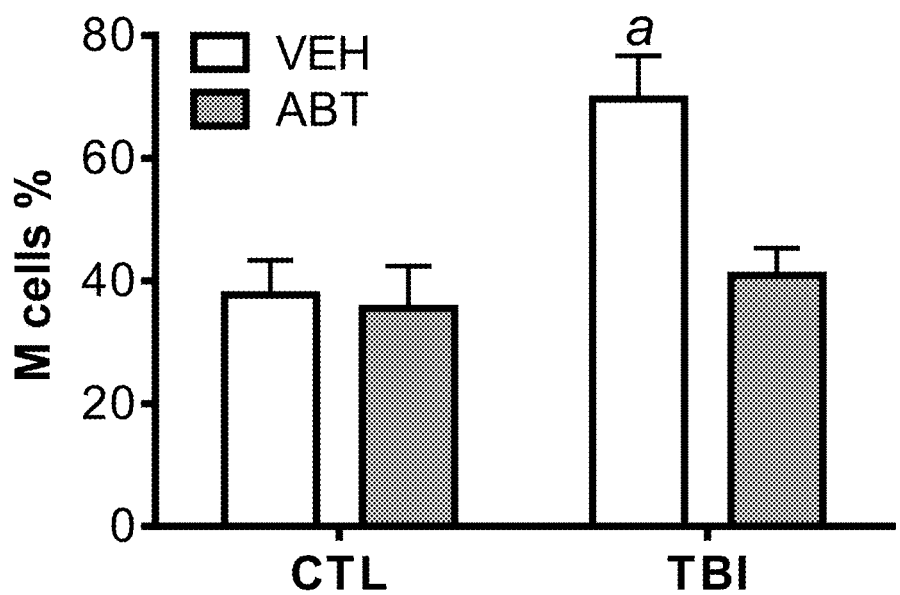

Using our sublethal TBI C57BL/6 mouse model[4], we asked whether ABT263 can effectively clear senescent HSCs induced by IR and whether the clearance mitigates IR-induced LT-BM injury or premature hematopoietic aging. BM HSCs from irradiated control (vehicle-treated) mice showed significant increases in p16 mRNA and SA-□-gal levels compared to HSCs from sham irradiated mice (FIG. 4A-C), indicating that sublethal TBI induces HSC senescence. By these markers, senescent HSCs were effectively cleared by ABT263 treatment. This effect is likely attributable to the selective depletion of senescent HSCs by ABT263, because in vitro ABT263 markedly reduced the clonogenicity of BM HSCs from irradiated mice but had little effect on the clonogenicity of BM HSCs from control unirradiated mice (FIG. 10). The clearance of senescent HSCs by ABT263 did not quantitatively reduce BM HSCs or hematopoietic progenitor cells (HPCs) (FIG. 11), probably due to an expansion of "normal" clones of HSCs that are spared or have repaired IR-induced damage. This suggestion is supported by the findings that ABT263 treatment significantly improved the clonogenicity and long-term engraftment ability of HSCs (FIG. 4D-O). In addition, ABT263 attenuated IR-induced HSC myeloid skewing and disruption of HSC quiescence, and reduced HSCs with persistent DNA damage (FIG. 4D-O; FIG. 12). The attenuation of myeloid skewing may be partly attributable to the increased lymphopoiesis (FIG. 13). These findings demonstrate that ABT263 can clear IR-induced senescent HSCs in vivo and this clearance can mitigate TBI-induced LT-BM injury or premature hematopoietic aging.

Our results provide the first proof of concept that selective clearance of SCs is pharmacologically achievable in vivo. ABT263 is the first senolytic drug, and also has potential as a novel radiation mitigator to reduce late IR effects associated with SCs. Because ABT263 has some toxic side effects[36], and adverse drug effects are hurdles for anti-aging therapies that require long treatment intervals[5, 37], it remains to be determined whether ABT263 can be used to delay aging or age-related diseases in normally aged animals and humans.

Materials and Methods for the Examples

Cells

Human WI-38 fibroblasts (WI38 cells, #CCL-75™), human IMR-90 fibroblasts (IMR90 cells, #CCL-186™), human renal epithelial cells (REC cells, #PCS-400-012™) were obtained from ACTT (Manassas, Va., USA). Mouse embryonic fibroblasts (MEF) were isolated from mouse embryos as described[1]. All cells were cultured in a complete medium (CM) (Dulbecco's Modified Eagle Medium supplemented with 10% fetal bovine serum [FBS], 100 U/ml penicillin, and 100 µg/ml streptomycin [all from Atlanta Biologicals, Norcross, Ga., and USA]) in a humidified incubator at 37° C. and 5% $CO_2$. Low passages of WI-38 cells (<25), IMR-90 (<25), REC cells (<25) and MEF (<3) were used as non-senescent controls or for induction of senescence to avoid replicative senescence. To induce replicative senescence, WI-38 cells were subcultivated until cell division ceased after about 38 passages or 60 population doublings (FIG. 5)[2]. To induce senescence by ionizing radiation (IR), cells at 70% confluence were exposed to 10 Gy of IR in a J. L. Shepherd Model Mark I 137Cesium γ-irradiator (J. L. Shepherd, Glendale, Calif., USA) with a rotating platform at a dose rate of 1.080 Gy/min. Cells were passaged once at 1:3 dilution 3 days later and became fully senescent 7 days after R as shown in FIG. 5. To induce senescence by expression of oncogenic Ras ($Ras^{V12}$), WI-38 cells were infected with the retroviruses pBabe-H-Ras or pBabe-puro (control) (Addgene, Cambridge, Mass., UAS)[2, 3]. Two days after infection, cells were selected in puromycin (2 µg/ml) (Invitrogen, Grand Island, N.Y., USA) for 5 days, after which they became senescent (FIG. 5). Senescent cells were maintained in culture for a few days, changing the culture medium every 3 days until use. For in vitro cell culture experiments, we usually repeated the experiments for at least three times to ensure the reproducibility of the data. In addition, the repeats of the experiments for three times will allow us to obtain 3 independent observations for statistical analysis.

Cell Viability Assays:

Three assays were used to measure cellular viability as described below:

Flow cytometry: Non-senescent and senescent cells were seeded into wells of 24- or 48-well at about 70% of confluence. After overnight incubation, non-senescent cells became quiescent after reaching confluence. Both quiescent non-senescent cells and permanently growth arrested senescent cells were treated with vehicle (0.1% DMSO or PBS) or increasing concentrations of the compounds listed in Table 1 for various durations. They were detached with 0.25% trypsin/1 mM EDTA and harvested in PBS with 2% of FBS. After incubated with propidium iodide (PI 100 ng/ml) in PBS at room temperature for 1 min, cells were centrifuged at 1200 rpm for 6 min and then resuspended in PBS with 2% of FBS for analysis by a BD LSR II flow cytometer (BD Biosciences, San Jose, Calif., USA). Viable cells ($PI^-$ cells) were numerated by flow cytometry at a constant flow rate and calculated as a percentage of control cells treated with vehicle using the formula: percentage of control=$(N_{drug}/N_C) \times 100$, where $N_{drug}$ and $N_C$ represent the absolute number of $PI^-$ viable cells of drug-treated and vehicle-treated cells, respectively.

MTT (3-[4,5-dimethylthiazol-2-yl]-2,5 diphenyl tetrazolium bromide) assay: Cells were harvested, washed and resuspended in CM and added to wells of 24- or 48-well plates as described above. After incubated with vehicle or increasing concentrations of ABT263 for 72 h, supernatants were removed from the culture, and 500 µl of MTT (5 mg/ml in PBS) were added into each well. After 4 h at 37° C., the formazan was solubilized by lysing the cells with 300 µl of DMSO. Absorbance of formazan was measured at 595 nm using a Microplate Reader (BioTek, Winooski, Vt., USA). Cell viability was calculated in the method as previously described[4].

Trypan blue exclusion assay: Cells were harvested, washed and resuspended in CM and added to wells of a 6-well plate as described above. After incubated with vehicle or increasing concentrations of ABT263 for 72 h, they were harvested by digestion with 0.25% trypsin/1 mM EDTA and then stained with 0.1% trypan blue (Sigma, St. Louis, Mo., UAS). Living cells stained negative for trypan blue and were counted under light microscopy.

Calculation of $LD_{50}$ Value:

Dose-response curves were generated for each compound and 50% lethal dose values ($LD_{50}$) were calculated by Probit Analysis. Briefly, Probit (set as y) was determined by looking up their correspondence to the % responded in Finney's table. The log of the compound concentrations was used as x. By fitting a line of regression, we produce the formula y=ax+b. The $LD_{50}$ value was determined by calculating the 'x' for a probit of 5.00 and then taking the inverse log of the concentration[5].

Senescence-Associated β-Galactosidase (SA-β-Gal) Staining:

SA-β-gal staining was determined using a commercial kit (Cat. #: 9860) (Cell Signaling Technology, Danvers, Mass., USA) according to the manufacturer's instructions. Briefly, cells were fixed in 2% (v/v) formaldehyde/0.2% glutaraldehyde for 10 min and then incubated in SA-β-gal staining solution (1 mg/ml 5-bromo-4-chloro-3-indolyl β-D-galactosidase, 40 mM citric acid, pH 6.0, 40 mM sodium phosphate, pH 6.0, 5 mM potassium ferrocyanide, 5 mM potassium ferricyanide, 150 mM sodium chloride, and 2 mM magnesium chloride) at 37° C. for 10 h. Senescent cells were identified as blue-stained cells under light microscopy. A total of 1000 cells were counted in 20 random fields on a slide to determine the percentage of SA-β-gal positive cells[2].

Flow SA-β-gal staining assay was performed by flow cytometry using an ImaGene Green™ $C_{12}FDG$ lacZ gene expression kit from Molecular Probes (Life Technologies, Carlsbad, Calif.), according to the manufacturer's instructions and protocols reported previously with the following modifications[6]. WI-38 cells were incubated with 150 μM chloroquine in DMEM culture medium supplemented with 10% FBS at 37° C. for 3 h. After washing twice with PBS to remove chloroquine, the cells were detached with 0.25% trypsin/1 mM EDTA, and incubated with pre-warmed $C_{12}FDG$ solution (32 μM C12FDG in DMEM culture medium supplemented with 10% FBS) for 2 h in a 37° C. water bath. The cells were washed again with PBS and analyzed immediately with a LSRII flow machine (BD Biosciences). Dead cells were excluded from the assay by PI staining.

BrdU Incorporation Assay:

BrdU incorporation assays were used to determine cell proliferation as previously described with minor modification[7]. Briefly, cells were incubated in CM containing 10 μM BrdU (Sigma, St. Louis, Mo., USA) for 6 h in a 4-well glass slide chamber (NalgeNunc Inc., Naperville, Ill., USA). They were washed twice with PBS and fixed in 70% ethanol at −20° C. for 30 min. After 3 washes with PBS, the cells were incubated in DNA denaturing solution (2N HCl/0.1% Triton X-100 in PBS) at room temperature for 1 h followed by 10 min incubation in 0.1 M sodium borate (pH 8.5) at room temperature. After washing with PBS and a 60 min incubation in PBS/1% bovine serum albumin, the cells were incubated overnight at 4° C. with 2 μg/ml mouse anti-BrdU monoclonal antibody (clone BU-33, from Sigma) and then with Texas Red-conjugated goat anti-mouse IgG (Jackson ImmunoResearch, West Grove, Pa., USA) with extensive washing between each step. Nuclear DNA was counterstained with Hoechst 33342 (Molecular Probes, Eugene, Oreg., USA). The cells were viewed and photographed using an Axioplan research microscope (Carl Zeiss Inc, Jena, Germany) equipped with a 100 W mercury light source. The images were captured with a Dage CCD100 integrating camera (Dage-MTI, Michigan, USA) and a Flashpoint 128 capture board (Integral Technologies, Indianapolis, Ind., USA). The captured images were processed using Image Pro Plus software (Media Cybernetics, Rockville, Md., USA) and displayed with Adobe Photoshop V6.0.

Apoptosis Analysis:

Cells were seeded into a 6-well plate at 4-6×10⁵ cells/well. After overnight incubation, the cells were treated with vehicle or 1.25 μM ABT263 with or without 20 μM Q-VD-OPh (APExBIO, Houston, Tex., USA). The cells were harvested 24 h after treatment and resuspended in 1× annexin V binding buffer (BD Biosciences) at 1×10⁶ cells/ml. An aliquot (100 μl) of the cell suspension was incubated with 5 μl of Annexin V-FITC (BD Biosciences) or PI (1 mg/ml) for 15 min at room temperature in the dark. After addition of 400 μl of 1× binding buffer, 10,000 cells per sample were analyzed by a BD LSR H flow cytometer (BD Biosciences).

Western Blot Analysis:

Cells (1×10⁶) were lysed in 100 μl lysis buffer (20 mM Tris-HCl, pH 7.4, 150 mM NaCl, 1 mM EDTA. 1 mM EGTA, 10% glycerol, 1.0% NP-40, 0.1 M NaF, 1 mM DTT, 1 mM PMSF, 1 mM NaVO4, 2 μg/ml leupeptin and aprotinin) for 30 min on ice, and cell extracts were sonicated 3 times (5 secs each time) on ice with a 25-sec interval in between using a Sonic Dismembrator Ultrasonic Convertor (Model F60, from Fisher, Pittsburgh, Pa., USA). The protein concentrations were quantified using the Bio-Rad Dc protein assay kit (Bio-Rad Laboratories, Hercules, Calif., USA). Equal amounts of protein (25-50 μg/lane) from each extract was resolved on 12% SDS-PAGE gels. Proteins were blotted to NOVEX NC membranes (Life Technologies, Carlsbad, Calif., USA). The membranes were blocked with TBS-T (5% nonfat milk in 25 mM Tris-HCl, pH 7.4. 3 mM KCl, 140 mM NaCl, and 0.05% Tween) and subsequently probed with primary antibodies at a predetermined optimal concentration as indicated in Supplementary Table 3 overnight at 4° C. or for 1 h at room temperature. After extensive washing with TBS-T, the membranes were incubated with an appropriate peroxidase-conjugated secondary antibody (Jackson ImmunoResearchEutope, Suffolk, CB8 1JX, UK) for 1 h at room temperature. After three washes with TBS-T, the blots were detected using the ECL Western Blotting Detection Reagents (Cat #WBKLS0100) (EMD MILLIPORE. Newmarket, Suffolk, UK) and recorded by exposure of the blots to X-ray film (Pierce Biotech, Rockford, Ill., USA). All the antibodies used in Western blot analysis are listed in Table 3.

TABLE 3

Antibodies for Western blot analyses

| Antibody | Clone | Antibody isotype | Catalog # | Concentration |
|---|---|---|---|---|
| Bcl-2[1] | 50E3 | Rabbit IgG Monoclonal | 2870S | 1:1000 |
| Bcl-xl[1] | — | Rabbit IgG Polyclonal | 2762S | 1:1000 |
| Bak[1] | D4E4 | Rabbit IgG Monoclonal | 12105S | 1:1000 |
| Bax[1] | — | Rabbit IgG Polyclonal | 2772S | 1:1000 |
| Mcl-1[1] | D35A5 | Rabbit IgG Monoclonal | 5453S | 1:1000 |
| Bim[1] | C34C5 | Rabbit IgG Monoclonal | 2933S | 1:500 |
| Caspase-3[1] | — | Rabbit IgG Polyclonal | 9662S | 1:1000 |
| Cleaved Caspase-3[1] | — | Rabbit IgG Polyclonal | 9661S | 1:1000 |
| Caspase-8[1] | 1C12 | Rabbit IgG Monoclonal | 9746S | 1:1000 |
| RIP[1] | D94C12 | Rabbit IgG Monoclonal | 3493S | 1:1000 |

TABLE 3-continued

Antibodies for Western blot analyses

| Antibody | Clone | Antibody isotype | Catalog # | Concentration |
|---|---|---|---|---|
| Bid[2] | — | Rabbit IgG Polyclonal | SC-11423 | 1:200 |
| β-actin[2] | — | Goat IgG Polyclonal | SC-1615 | 1:1000 |
| Bad[3] | 48/Bad | Mouse IgG2b Monoclonal | 610391 | 1:500 |
| Noxa[4] | 114C307 | Mouse IgG Monoclonal | OP180 | 1:500 |

Footnotes:
[1] Cell signaling, Danvers, MA, USA;
[2] Santa Cruz, Dallas, Texas, USA;
[3] BD Biosciences, San Jose, CA, USA;
[4] EMD Millipore Corporation, San Diego, CA, USA.

Lentivirus Production:

Lentivirus was produced after transient infection of human embryonic kidney (HEK) 293T cells with individual lentiviral vectors along with the packaging plasmids pCMV-VSV-G and psPAX2 (Addgene, Cambridge, Mass., USA) using FuGEN6-HD (Roche Diagnostics, Mannheim, Germany) according to the Roche protocol. Supernatants containing viral particles were collected 48 h later and filtered through 0.22 mm filter. Viral particles were concentrated using a PEG-itTM Virus Precipitation Solution kit from System Biosciences (Mountain View, Calif., UAS) according to the manufacturer's instructions Knockdown of Bcl-2 and/or Bcl-XL with Short Hairpin RNA (shRNA):

Control lentiviral pLKO.1 vectors and pLKO.1 vectors containing shRNAs for human Bcl-2 (RHS4533-EG596) and Bcl-XL (RHS4533-EG598) were obtained from Thermo Fisher Scientific, Inc. (Waltham, Mass., USA). Viral particles were produced as described above. To establish stable Bcl-2 and/or Bcl-XL knockdown WI-38 cells, cells were infected twice with viral particles under centrifugation (900×g) at 32° C. for 30 min. Stably transduced cells were selected with puromycin (2 mg/ml). Bcl-2 and/or Bcl-XL knockdown in WI-38/Bcl-2, WI-38/Bcl-XL, and WI-38/Bcl-2/Bcl-XL cells, respectively, were confirmed by Western blot before the cells were used.

Mice:

Male C57BL/6J (or CD45.2) mice and B6.SJL-Ptprc$^a$Pep3$^b$/BoyJ (or CD45.1) mice were purchased from Jackson Lab (Bar Harbor, Mass., USA). p16-3MR transgenic mice were kindly provided by Dr. Judith Campisi (Buck Institute for Research on Aging, Novato Calif.)[8]. Mice were randomly assigned to 4 to 5 mice per cage housed at University of Arkansas for Medical Sciences (UAMS) AAALAC-certified animal facility and then randomly assigned to a treatment group. For animal studies, sample sizes were estimated according to our previous experiences. They received food and water ad libitum. The Institutional Animal Care and Use Committees of UAMS approved all experimental procedures used in this study.

Total Body Irradiation (TBI) and ABT263 and Ganciclovir (GCV) Treatment:

C57BL/6J and p16-3MR transgenic mice at 2-3 months of age were exposed to sham irradiation as controls or a sublethal dose (6 Gy) of TBI in a J. L. Shepherd Model Mark I 137Cesium γ-irradiator (J. L. Shepherd, Glendale, Calif.) at a dose rate of 1.080 Gy/min. Eight or 16 wks after TBI, mice were treated with vehicle (PBS or ethanol/polyethylene glycol 400/Phosal 50 PG at 10:30:60), ABT263 (in ethanol/polyethylene glycol 400/Phosal 50 PG vehicle), or GCV (in PBS). ABT was given by gavage at 50 mg/kg/d for 7 d per cycle for 2 cycles with a 2-wk interval. GCV was given to the mice by ip injection at 25 mg/kg/d for 5 d per cycle for 2 cycles with a 2-wk interval. Luminescence imaging was performed on p16-3MR mice 1 day after the last treatment with vehicle, ABT263, or GCV as described below. The mice were euthanized the day after the imaging by $CO_2$ inhalation and followed by cervical dislocation. Tissues were harvested for immediate tissue luminescence imaging as described below or RNA extraction for analyses of p16, IL-1α, CCL-5, and CXCL-10 mRNA levels by qRT-PCR. C57BL/6 mice were euthanized 5 wks after vehicle or ABT263 treatment to harvest bone marrow cells (BMCs) for assays described below.

Bioluminescence Assay:

For in vivo luminescence, mice were injected i.p. with 250 μl of Xenolight RediJect Coelenterazine h (100 μg/mL, Calipers-PerkinElmer, Waltham, Mass., USA). The mice were anesthetized with 4% isoflurane gas at 1 L/minute oxygen flow 5 min after the injection. Luminescence images were acquired using a Xenogen IVIS-200 Optical In Vivo imaging System equipped with a Living Image Version 4.3.1 (Caliper Life Sciences, Hopkinton Mass., USA). Mice were oriented in a supine position in the scanner. Regions of interest were carefully placed around all bioluminescent signals while minimizing inclusion of scatter signals. All image scans were acquired with an E field of view at 15-20 min after the injection while the mice were kept under 1.5% isoflurane gas at 1 L/min oxygen flow.

For tissue luminescence imaging, after harvested from euthanized mice, tissues were immediately soaked in pre-warmed (37° C.) PBS with 2% FBS and 1:10 dilution of Xenolight RediJect Coelenterazine h for 10 min. They were transferred into a new 35-mm dish and luminescence images were taken 12-15 min after soaking in the substrate solution using a Xenogen IVIS-200 Optical In Vivo imaging System.

Isolation of Bone Marrow Mononuclear Cells (BM-MNCs), Lineage Negative Hematopoietic Cells (Lin$^-$ Cells) and HSCs:

The femora and tibiae were harvested from mice immediately after they were euthanized. BM cells were flushed from the bones into HBSS containing 2% FCS using a 21-gauge needle and syringe. Cells from 3-10 mice were pooled and centrifuged through Histopaque 1083 (Sigma, St. Louis, Mo., UAS) to isolate BM-MNCs. For isolation of Lin$^-$ cells, BM-MNCs were incubated with biotin-conjugated rat antibodies specific for murine CD5, Mac-1, CD45R/B220, Ter-119, and Gr-1. The labeled mature lymphoid and myeloid cells were depleted twice by incubation with goat anti-rat IgG paramagnetic beads (Dynal Inc, Lake Success, N.Y., USA) at a bead:cell ratio of approximately 4:1. Cells binding the paramagnetic beads were removed with a magnetic field. The negatively isolated Lin$^-$ cells were washed twice with 2% FCS/HBSS and resuspended in complete medium (RPMI1640 medium supplemented with 10% FCS, 2 mM L-glutamine, 10 μM HEPES buffer, and 100 U/ml penicillin and streptomycin) at 1×10$^6$/ml. HSCs (CD150$^+$CD48$^-$ LSK$^+$ cells) were sorted by a BD FACSAria II cell sorter (BD Biosciences, San Jose, Calif.) after Lin$^-$ cells were preincubated with anti-CD16/32 antibody to block the Fcγ receptors and then stained with anti-Sca1-PE, c-Kit-APC-Cy7, CD150-APC and CD48-Pacific blue antibodies. Dead cells were excluded by gating out the cells that stained positive with PI. Information for all antibodies used in the staining is provided in Table 4.

TABLE 4

Antibodies for flow cytometry and cell sorting

| Antibody | Clone | Antibody isotype | Conjugate | Concentration |
|---|---|---|---|---|
| CD45R/B220[1] | RA3-6B2 | IgG$_{2a}$ | purified | 1:200 |
| CD3e[1] | 145-2C11 | IgG$_1$ | purified | 1:200 |
| CD11b[1] | M1/70 | IgG$_{2b}$ | purified | 1:200 |
| Gr-1[1] | RB6-8C5 | IgG$_{2b}$ | purified | 1:200 |
| Ter-119[1] | Ter-119 | IgG$_{2b}$ | purified | 1:200 |
| CD45R/B220[1] | RA3-6B2 | IgG$_{2a}$ | biotin | 1:200 |
| CD3e[1] | 145-2C11 | IgG$_1$ | biotin | 1:200 |
| CD11b[1] | M1/70 | IgG$_{2b}$ | biotin | 1:200 |
| Gr-1[1] | RB6-8C5 | IgG$_{2b}$ | biotin | 1:200 |
| Ter-119[1] | Ter-119 | IgG$_{2b}$ | biotin | 1:200 |
| CD16/CD32[1] | 2.4G2 | IgG$_{2b}$ | Purified | 1:200 |
| CD45.2[1] | 104 | IgG$_{2a}$ | FITC | 1:100 |
| CD45R/B220[1] | RA3-6B2 | IgG$_{2a}$ | APC | 1:200 |
| CD45R/B220[1] | RA3-6B2 | IgG$_{2a}$ | PE | 1:200 |
| CD90.2[1] | 53-2.1 | IgG$_{2a}$ | APC | 1:200 |
| CD11b[1] | M1/70 | IgG$_{2a}$ | PE | 1:200 |
| Gr-1[1] | RB6-8C5 | IgG$_{2a}$ | PE | 1:200 |
| Streptavidin | Streptavidin |  | FITC | 1:200 |
| Sca-1[1] | E13-161.7 | IgG$_{2a}$ | PE | 1:100 |
| Sca-1[1] | E13-161.7 | IgG$_{2a}$ | PE-Cy™ 7 | 1:100 |
| CD135[1] | 4G8 | IgG$_1$ | PE | 1:100 |
| c-kit[2] | 2B8 | IgG$_{2b}$ | APC-H7 | 1:100 |
| c-kit[2] | 2B8 | IgG$_{2b}$ | APC-eFluor® 780 | 1:100 |
| CD150[2] | 9D1 | IgG$_{2a}$ | APC | 1:100 |
| CD34[2] | RAM34 | IgG$_{2a}$ | Alexa Fluor® 700 | 1:20 |
| Ki-67[2] | 20Raj1 | IgG$_1$ | FITC | 1:50 |
| Ki-67[2] | 20Raj1 | IgG$_1$ | Alexa Fluor® 700 | 1:50 |
| CD48[3] | HM481 | IgG$_{2a}$ | Pacific blue | 1:200 |
| γH2AX[3] | 2F3 | IgG$_1$ | FITC | 1:200 |
| CD93[2] | AA4.1 | IgG$_{2b}$ | PE-Cy7 | 1:100 |
| IgM[2] | II/41 | IgG$_{2a}$ | APC | 1:100 |

Footnotes:
[1]BD Biosciences, San Jose, CA;
[2]eBioscience, San Jose, CA;
[3]Biolegend, San Diego, CA.

B Cell Analysis:

BM-MNCs (1×10$^6$) from each mouse were incubated with FITC-labeled anti-CD93, APC-labeled 10, and PE-labeled B220 at 4° C. for 30 min and then washed with PBS containing 0.25 µg/ml PI. B cell populations were analyzed by a BD LSRII flow cytometer (BD Biosciences).

Single Cell/Culture:

Sixty single HSCs from irradiated and sham-irradiated mice were sorted directly into wells of round-bottom 96-well plates. They were cultured in RPMI 1640 culture medium supplemented with 10% FCS, 50 ng/ml SCF, Flt3, TPO, and GM-CSF, 20 ng/ml of IL-3, 5 U/ml EPO in the absence or presence of 1.25 µM ABT263. Freshly prepared medium was added every 3 days, Two weeks later, the numbers of cells produced by each HSC were counted.

Cobblestone Area Forming Cell (CAFC) Assay:

Feeder cell stromal layers were prepared by seeding 10$^3$/well FBMD-1 stromal cells in each well of flat-bottom 96-well plates (Falcon, Lincoln Park, N.J.). One week later, BM-MNCs resuspended in CAFC medium (Iscove's MDM supplemented with 20% horse serum, 10$^{-5}$ M hydrocortisone, 10$^{-5}$ M 2-mercaptoethanol, 100 U/ml penicillin, and 100 µg/ml streptomycin) after various treatments described above were overlaid on these stromal layers in 6 dilutions at 3-fold intervals. Twenty wells were plated for each dilution to allow limiting dilution analysis of the precursor cells forming hematopoietic cell clones under the stromal layer. Cultures were fed weekly by changing one-half of the media. The frequencies of CAFC were determined on days 14 and 35. Wells were scored positive if at least one phase-dark hematopoietic clone (containing 5 or more cells) was seen. The frequency of CAFC was then calculated by using Poisson statistics as described previously[9, 10].

Competitive Repopulation Assay (CRA):

BM cells from CD45.2 mice 17 wks after they were exposed to a sublethal TBI dose (6 Gy) or sham-irradiated with vehicle or ABT263 treatment were mixed with 2×10$^5$ competitive BM cells pooled from 3 CD45.1 mice and then transplanted into lethally irradiated (9.5 Gy TBI) CD45.1 recipients (6 recipients/group) via retro-orbital injection of the venous sinus, Donor cell engraftment in the recipients was analyzed at various times after transplantation as previously described[9, 10].

Cell Cycle and DNA Damage Analysis:

Lin$^-$ cells were first stained with antibodies against various cell-surface markers and fixed and permeabilized using the Fixation/Permeabilization Solution from BD-Pharmingen (San Diego, Calif.). Subsequently, they were stained with anti-Ki67-FITC antibody, anti-phospho-Histone-H2AX (γH2AX) (Ser139)-Alex 647 and 7-AAD and then analyzed by flow cytometer as previously described[9].

Quantitative PCR (qPCR):

Total cellular RNA was extracted from non-senescent and senescent WI-38 cells and various tissues using RNeasy Mini kit (QIAGEN, Gaithersburg, Md.). Reverse transcription was performed immediately using Applied Biosystems' High Capacity cDNA Reverse Transcription kits (Life Technologies, Grand Island, N.Y., USA) according to the manufacturer's instructions.

Total cellular RNA was extracted from about 5000 sorted HSCs using the Zymo research Quick-RNA Micro Prep kit (The Epigenetics Company, Irvine, Calif., USA) according to the manufacturer's instructions. Reverse transcription was performed immediately using Fluidigm protocol (Fluidigm, South San Francisco, Calif., USA): 1 µl RNA was added to individual wells of 96-well plates containing 2.5 µl Cells-Direct 2× reaction mix (Invitrogen, Grand Island, N.Y., USA), 0.15 µl nuclease free water, 0.1 µl Superscript III/Platinum Taq mix (Invitrogen), and 1.25 µl 0.2× TaqMan assay mix containing a pool of 1:100 diluted TaqMan assays for mouse p16 and p21 and HPRT mRNA (Invitrogen) as shown in Table 5.

To measure p16 mRNA expression in WI-38 cells and mouse tissues, qPCRs were run with TaqMan qPCR reagents and primers (Table 5) from Applied Biosystem. Human GAPDH and mouse HPRT were used as internal controls. Briefly, 1 µl cDNA was mixed with 10 µl TaqMan Universal Mastermix (Invitrogen) and 1 µl of Taqman primer. Samples were added with 8 µl of H$_2$O to give a total 20 µl, and qPCR was performed (50° C. for 2 min, 95° C. for 10 min, 40×(95° C. for 15 s and 60° C. for 1 min). All reactions were run in triplicate on an ABI StepOnePlus Real-Time PCR System (Applied Biosystems).

To measure p21 and GAPDH mRNA levels in WI-38 cells and IL-1α, TNFα, CCL-5, and CXCL-10 mRNA levels in mouse tissues, SYBR assay kit was used (Applied biosystems in life technologies). Briefly, 1 µl cDNA was mixed with 7.5 µl SYBR Green PCR Master Mix and 0.2 µl of primers (Table 5). Samples were then added with 6.30 µl of H2O to give a total 15 µl of mixture. qPCR conditions were as follows: 95° C. for 10 min, 40×(95° C. for 15 s and 60° C. for 1 min), 95° C. for 15 min, 60° C. for 60 min, 95° C. for 15 min. All reactions were run in triplicate on an ABI StepOnePlus Real-Time PCR System.

TABLE 5

Sequences of the primers used for qRT-PCR

| Gene | SEQ ID NO: | Forward sequences | SEQ ID NO: | Reverse sequences |
|---|---|---|---|---|
| Human p16[1] | 1 | 5-CCAACGCACCGAATAGTTACG-3 | 2 | 5-GCGCTGCCCATCATCATG-3 |
| Human p21[2] | 3 | 5-GACAGCAGAGGAAGACCATGTGGAC-3 | 4 | 5-GAGTGGTAGAAATCTGTCATGCTG-3 |
| Human GAPDH[1] | | Cat# 4331182 | | Cat# 4331182 |
| Mouse p16[1] | 5 | 5-CGGTCGTACCCCGATTCAG-3 | 6 | 5-GCACCGTAGTTGAGCAGAAGAG-3 |
| Mouse HPRT[1] | | Cat# 4351370 | | Cat# 4351370 |
| Mouse p21[2] | 7 | 5-AATCCTGGTGATGTCCGACC-3 | 8 | 5-AAAGTTCCACGGTTTCGG-3 |
| Mouse IL-1α[2] | 9 | 5-CCATAACCCATGATCTGGAAGAGAC-3 | 10 | 5-GTCCACATCCTGATATATAGTTTG-3 |
| Mouse TNFα[2] | 11 | 5-TGAACTTCGGGGTGATCGGTC-3 | 12 | 5-CACTTGGTGGTTTGCTACGACG-3 |
| Mouse CCL-5[2] | 13 | 5-CCCGCACCTGCCTCACCATATGG-3 | 14 | 5-CCTTCGAGTGACAAACACGACTG-3 |
| Mouse CXCL-10[2] | 15 | 5-GGTCTGAGTGGGACTCAAGGGATC-3 | 16 | 5-TCATCGTGGCAATGATCTCAACAC-3 |
| Mouse HPRT[2] | 17 | 5-AGCAGTACAGCCCCAAAATGGTTA-3 | 18 | 5-TCAAGGGCATATCCAACAAAC-3 |

Footnotes:
[1]Life technologies, Grand Island, NY, U.S.A.;
[2]Integrated DNA Technologies, Coralville, IA, U.S.A.

Statistical Analysis:

Data display normal variance. No statistical method was used to predetermine sample size. The experiments were not randomized except for the in vivo animal studies with mice as described in the section of mice. The investigators were not blinded to avocation during experiments and outcome assessment. The data were analyzed by analysis of variance (ANOVA) using GraphPad Prism from GraphPad Software (San Diego, Calif.). In the event that ANOVA justifies post-hoc comparisons between group means, these were conducted using Neuman-Keuls or Tukey's multiple comparisons test. $P<0.05$ was considered significant.

REFERENCES FOR THE EXAMPLES

1. Le, O. N. et al. Ionizing radiation-induced long-term expression of senescence markers in mice is independent of p53 and immune status. *Aging Cell* 9, 398-409 (2010).
2. Munoz-Espin, D. & Serrano, M. Cellular senescence: from physiology to pathology. *Nat Rev Mol Cell Biol* 15, 482-496 (2014).
3. Richardson, R. B. Ionizing radiation and aging: rejuvenating an old idea. *Aging* (Albany. N.Y.) 1, 887-902 (2009).
4. Shao, L. et al. Total body irradiation causes long-term mouse BM injury via induction of HSC premature senescence in an Ink4a- and Arf-independent manner. *Blood* 123, 3105-3115 (2014).
5. Tchkonia, T., Zhu, Y., van, D. J., Campisi, J., & Kirkland, J. L. Cellular senescence and the senescent secretory phenotype: therapeutic opportunities. *J Clin Invest* 123, 966-972 (2013).
6. van Deursen, J. M. The role of senescent cells in ageing. *Nature* 509, 439-446 (2014).
7. Baker, D. J. et al. Clearance of p16Ink4a-positive senescent cells delays ageing-associated disorders. *Nature* 479, 232-236 (2011).
8. Campisi, J. Aging, cellular senescence, and cancer. *Annu Rev Physiol* 75, 685-705 (2013).
9. Marcotte, R. & Wang, E. Replicative senescence revisited. *J Gerontol A Biol Sci Med Sci* 57, B257-B269 (2002).
10. Serrano, M. & Blasco, M. A. Putting the stress on senescence. *Curr Opin Cell Biol* 13, 748-753 (2001).
11. Citrin, D. E. et al. Role of type II pneumocyte senescence in radiation-induced lung fibrosis. *J Natl Cancer Inst* 105, 1474-1484 (2013).
12. Wang, Y., Schulte, B. A., LaRue, A. C., Ogawa, M., & Zhou, D. Total body irradiation selectively induces murine hematopoietic stem cell senescence. *Blood* 107, 358-366 (2006).
13. Tse, C. et al. ABT-263: a potent and orally bioavailable Bcl-2 family inhibitor. *Cancer Res* 68, 3421-3428 (2008).
14. Caserta, T. M., Smith, A. N., Gultice, A. D., Reedy, M. A., & Brown, T. L. Q-VD-OPh, a broad spectrum caspase inhibitor with potent antiapoptotic properties. *Apoptosis* 8, 345-352 (2003).
15. Cory, S. & Adams, J. M. The Bcl2 family: regulators of the cellular life-or-death switch. *Nat Rev Cancer* 2, 647-656 (2002).
16. Czabotar, P. E., Lessene, G., Strasser, A., & Adams, J. M. Control of apoptosis by the BCL-2 protein family: implications for physiology and therapy. *Nat Rev Mol Cell Biol* 15, 49-63 (2014).
17. Childs, B. G., Baker, D. J., Kirkland, J. L., Campisi, J., & van Deursen, J. M. Senescence and apoptosis: dueling or complementary cell fates? *EMBO Rep* 15, 1139-1153 (2014).
18. Souers, A. J. et al. ABT-199, a potent and selective BCL-2 inhibitor, achieves antitumor activity while sparing platelets. *Nat Med* 19, 202-208 (2013).
19. Lessene, G. et al. Structure-guided design of a selective BCL-X(L) inhibitor. *Nat Chem. Biol* 9, 390-397 (2013).
20. Burd, C. E. et al. Monitoring tumorigenesis and senescence in vivo with a p16(INK4a)-luciferase model. *Cell* 152, 340-351 (2013).
21. Sorrentino, J. A. et al. p16INK4a reporter mice reveal age-promoting effects of environmental toxicants. *J Clin Invest* 124, 169-173 (2014).
22. Janzen, V. et al. Stem-cell ageing modified by the cyclin-dependent kinase inhibitor p16INK4a. *Nature* 443, 421-426 (2006).
23. Demaria, M. et al. An Essential Role for Senescent Cells in Optimal Wound Healing through Secretion of PDGF-AA. *Dev Cell* 31, 722-733 (2014).
24. Laberge, R. M. et al. Mitochondrial DNA damage induces apoptosis in senescent cells. *Cell Death Dis* 4, e727 (2013).
25. Coppe, J. P., Desprez, P. Y., Krtolica, A., & Campisi, J. The senescence-associated secretory phenotype: the dark side of tumor suppression. *Annu Rev Pathol* 5, 99-118 (2010).
26. Shao, L., Luo, Y., & Zhou, D. Hematopoietic stem cell injury induced by ionizing radiation. *Antioxid. Redox Signal.* 20, 1447-1462 (2014).
27. Beerman, I., Maloney, W. J., Weissmann, I. L., & Rossi, D. J. Stem cells and the aging hematopoietic system. *Curr Opin Immunol* 22, 500-506 (2010).

28. Dykstra, B., Olthof, S., Schreuder, J., Ritsema, M., & de, H. G. Clonal analysis reveals multiple functional defects of aged murine hematopoietic stem cells. *J Exp Med* 208, 2691-2703 (2011).
29. Geiger, H., de, H. G., & Florian, M. C. The ageing haematopoietic stem cell compartment. *Nat Rev Immunol* 13, 376-389 (2013).
30. Fleenor, C. J., Marusyk, A., & DeGregori, J. Ionizing radiation and hematopoietic malignancies: altering the adaptive landscape. *Cell Cycle* 9, 3005-3011 (2010).
31. Geiger, H., Rennebeck, G., & Van, Z. G. Regulation of hematopoietic stem cell aging in vivo by a distinct genetic element. *Proc Natl Acad Sci USA* 102, 5102-5107 (2005).
32. Harfouche, G. & Martin, M. T. Response of normal stem cells to ionizing radiation: a balance between homeostasis and genomic stability. *Mutat. Res* 704, 167-174 (2010).
33. Testa, N. G., Hendry, J. H., & Molineux, G. Long-term bone marrow damage in experimental systems and in patients after radiation or chemotherapy. *Anticancer Res.* 5, 101-110 (1985).
34. Gale, R. P. Myelosuppressive effects of antineoplastic chemotherapy in *Hematopoiesis: Long-term effects of chemotherapy and radiation* (eds. Testa, N. G. & Gale, R. P.) 63-73 (Marcel Dekker, Inc, New York, 1988).
35. Lohrmann, H. P. E. & Schreml, W. Long-term hematopoietic damage after cytotoxic drug therapy for solid tumors in *Hematopoiesis: Long-term effects of chemotherapy and radiation* (eds. Testa, N. G. & Gale, R. P.) 325-337 (Marcel Dekker, Inc, New York, 1988).
36. Rudin, C. M. et al. Phase II study of single-agent navitoclax (ABT-263) and biomarker correlates in patients with relapsed small cell lung cancer. *Clin Cancer Res* 18, 3163-3169 (2012).
37. Le Couteur, D. G., McLachlan, A. J., Quinn, R. J., Simpson, S. J., & de, C. R. Aging biology and novel targets for drug discovery. *J Gerontol A Biol Sci Med Sci* 67, 168-174 (2012).

REFERENCES FOR THE MATERIALS AND METHODS

1. Jozefczuk, J., Drews, K., & Adjaye, J. Preparation of mouse embryonic fibroblast cells suitable for culturing human embryonic and induced pluripotent stem cells. *J Vis. Exp* (2012).
2. Wang, Y., Scheiber, M. N., Neumann, C., Calin, G. A., & Zhou, D. MicroRNA regulation of ionizing radiation-induced premature senescence. *Int J Radiat Oncol Biol Phys* 81, 839-848 (2011).
3. Serrano, M., Lin, A. W., McCurrach, M. E., Beach, D., & Lowe, S. W. Oncogenic ras provokes premature cell senescence associated with accumulation of p53 and p16INK4a. *Cell* 88, 593-602 (1997).
4. Meng, A. et al. Sphingomyelin synthase as a potential target for D609-induced apoptosis in U937 human monocytic leukemia cells. *Exp Cell Res* 292, 385-392 (2004).
5. Finney D J *Probit Analysis* (Cambridge University Press, England, 1952).
6. Debacq-Chainiaux, F., Erusalimsky, J. D., Campisi, J., & Toussaint, O. Protocols to detect senescence-associated beta-galactosidase (SA-betagal) activity, a biomarker of senescent cells in culture and in vivo. *Nat Protoc.* 4, 1798-1806 (2009).
7. Wang, Y., Meng, A., & Zhou, D. Inhibition of phosphatidylinositol 3-kinase uncouples H2O2-induced senescent phenotype and cell cycle arrest in normal human diploid fibroblasts. *Exp Cell Res* 298, 188-196 (2004).
8. Demaria, M. et al. An Essential Role for Senescent Cells in Optimal Wound Healing through Secretion of PDGF-AA. *Dev Cell* 31, 722-733 (2014).
9. Shao, L. et al. Total body irradiation causes long-term mouse BM injury via induction of HSC premature senescence in an Ink4a- and Arf-independent manner. *Blood* 123, 3105-3115 (2014).
10. Wang, Y., Schulte, B. A., LaRue, A. C., Ogawa, M., & Zhou, D. Total body irradiation selectively induces murine hematopoietic stem cell senescence. *Blood* 107, 358-366 (2006).

What is claimed is:

1. A method of treating bone marrow injury in a subject who has not been administered cancer therapy, the method comprising contacting cells in the subject's bone marrow with a therapeutically effective amount of a compound that inhibits the biological activity of Bcl-xL and Bcl-2 protein that is present in p16 positive senescent cells in the bone marrow, wherein the compound is selected from GX15-070 (obatoclax), gossypol (AT-101), apogossypolone, TW37, TM-1206, ABT-737, ABT-263 (navitoclax), WHEI539, and combinations thereof,
   whereby the compound selectively removes the senescent cells in comparison with non-senescent cells in the subject's bone marrow, thereby delaying progression of the injury.

2. The method of claim 1, wherein the $LD_{50}$ of the compound for non-senescent cells is greater than 10 times higher than the $LD_{50}$ for the senescent cells.

3. A method of treating bone marrow injury in a subject who does not have cancer, the method comprising contacting cells in the subject's bone marrow with a therapeutically effective amount of a compound,
   whereby the compound inhibits the biological activity of Bcl xL and Bcl-2 protein and selectively removes the senescent cells in comparison with non-senescent cells in the subject's bone marrow, thereby delaying progression of the injury, wherein the compound is selected from GX15-070 (obatoclax), gossypol (AT-101), apogossypolone, TW37, TM-1206, ABT-737, ABT-263 (navitoclax), WHEI539, and combinations thereof.

* * * * *

SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 1
ccaacgcacc gaatagttac g                                      21

<210> SEQ ID NO 2
<211> LENGTH: 18
<212> TYPE: DNA
<213> ORGANISM: Artificial Sequence
<220> FEATURE:
<223> OTHER INFORMATION: SYNTHESIZED

<400> SEQUENCE: 2
gcgctgccca tcatcatg                                          18

<210> SEQ ID NO 3
<211> LENGTH: 25

<212> TYPE: DNA
<213> ORGANISM: Artificial Sequence
<220> FEATURE:
<223> OTHER INFORMATION: SYNTHESIZED

<400> SEQUENCE: 3
gacagcagag gaagaccatg tggac                                    25

<210> SEQ ID NO 4
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 4
gagtggtaga aatctgtcat gctg                                     24

<210> SEQ ID NO 5
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 5
cggtcgtacc ccgattcag                                           19

<210> SEQ ID NO 6
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 6
gcaccgtagt tgagcagaag ag                                       22

<210> SEQ ID NO 7
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 7
aatcctggtg atgtccgacc                                          20

<210> SEQ ID NO 8
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 8
aaagttccac ggttctcgg                                           19

<210> SEQ ID NO 9
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 9
ccataaccca tgatctggaa gagac					25

<210> SEQ ID NO 10
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 10
gtccacatcc tgatatatag tttg					24

<210> SEQ ID NO 11
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 11
tgaacttcgg ggtgatcggt c						21

<210> SEQ ID NO 12
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 12
cacttggtgg tttgctacga cg					22

<210> SEQ ID NO 13
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 13
cccgcacctg cctcaccata tgg					23

<210> SEQ ID NO 14
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 14
ccttcgagtg acaaacacga ctg					23

<210> SEQ ID NO 15
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 15
ggtctgagtg ggactcaagg gatc					24

<210> SEQ ID NO 16
<211> LENGTH: 24
<212> TYPE: DNA
<213> ORGANISM: Artificial Sequence

```
<220> FEATURE:
<223> OTHER INFORMATION: SYNTHESIZED

<400> SEQUENCE: 16
tcatcgtggc aatgatctca acac                                         24

<210> SEQ ID NO 17
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 17
agcagtacag ccccaaaatg gtta                                         24

<210> SEQ ID NO 18
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 18
tcaagggcat atccaacaac aaac                                         24
```